United States Patent
Clark et al.

(10) Patent No.: US 6,656,428 B1
(45) Date of Patent: Dec. 2, 2003

(54) AUTOMATED POINT OF CARE DETECTION SYSTEM INCLUDING COMPLETE SAMPLE PROCESSING CAPABILITIES

(75) Inventors: David D. Clark, Longmont, CO (US); Jeffrey W. Steaffens, Lafayette, CO (US); John Dorson, Lafayette, CO (US); Ian Wells, Escondido, CA (US); Alan J. Fujii, Newport Beach, CA (US); James E. Maynard, Boulder, CO (US); James Baker, Dorchester, MA (US); John Zeis, San Marcos, CA (US); Charles Bickoff, Sharon, MA (US); Richard D. McEachern, Escondido, CA (US); Kunio Kohga, Fujisawa (JP); Andrew Ghusson, Northboro, MA (US); John C. Balsavich, Jr., Foxborough, MA (US)

(73) Assignee: Thermo Biostar, Inc., Louisville, CO (US)

( * ) Notice: Subject to any disclaimer, the term of this patent is extended or adjusted under 35 U.S.C. 154(b) by 300 days.

(21) Appl. No.: 09/632,343

(22) Filed: Aug. 3, 2000

Related U.S. Application Data

(60) Provisional application No. 60/147,681, filed on Aug. 6, 1999.

(51) Int. Cl.[7] .................... G01N 21/00; G01N 31/22; G01N 35/00; G01N 35/02

(52) U.S. Cl. .................... 422/58; 422/61; 422/62; 422/63; 422/64; 422/68.1; 422/56; 422/72; 422/100; 422/81; 422/101; 422/65; 422/99; 435/7.1; 436/43; 436/46; 436/47

(58) Field of Search .................... 422/58, 68.1, 61–64, 422/72, 100, 81, 101, 65, 56, 99; 435/7.1; 436/43, 46, 47

(56) References Cited

U.S. PATENT DOCUMENTS

| | | | |
|---|---|---|---|
| 4,199,543 A | 4/1980 | Phillips | 422/63 |
| 4,314,970 A | 2/1982 | Stein et al. | 422/72 |
| 4,338,279 A | 7/1982 | Orimo et al. | 422/64 |
| 4,455,280 A | 6/1984 | Shinohava et al. | 422/62 |

(List continued on next page.)

FOREIGN PATENT DOCUMENTS

| | | | | |
|---|---|---|---|---|
| WO | WO 97/14460 | 4/1997 | | A61M/2/25 |
| WO | WO 98/10866 | 3/1998 | | B01L/3/00 |
| WO | WO 98/13519 | 4/1998 | | C12Q/1/66 |
| WO | WO 98/19614 | 5/1998 | | A61B/17/36 |
| WO | WO 98/37416 | 8/1998 | | G01N/33/53 |

Primary Examiner—Jan Ludlow
Assistant Examiner—Brian Sines
(74) Attorney, Agent, or Firm—Foley & Lardner; Richard J. Warburg; Michael A. Whittaker

(57) ABSTRACT

The present invention relates to cost effective analytical instruments for determining the presence or amount of an analyte in a sample. The analytical instruments utilize an assay cartridge which has a sample receiving port and a rotatable carousel containing a plurality of reagent wells. Each reagent well includes a piston element for delivery of reagent to a test surface. The instrument is capable of indexing the assay cartridge to deliver sample and reagents to a test surface in a predetermined and flexibile manner, thus providing an assay protocol which is specific to the type of sample under analysis. The invention also relates to components, features, disposables, reagent delivery systems, accessories, and methods for using such instruments. Appropriate applications include infectious disease testing, cancer detection and monitoring, therapeutic drug level monitoring, allergy testing, environmental testing, food testing, diagnostic testing of human and veterinary samples, and off-line process testing.

38 Claims, 58 Drawing Sheets

U.S. PATENT DOCUMENTS

| | | | |
|---|---|---|---|
| 4,483,297 A | 11/1984 | Takekawa | 436/43 |
| 4,540,549 A | 9/1985 | Manabe | 422/64 |
| 4,689,204 A | 8/1987 | Buck et al. | 422/100 |
| 4,707,450 A | 11/1987 | Nason | 435/295 |
| 4,738,826 A | 4/1988 | Harris | 422/100 |
| 4,753,775 A | 6/1988 | Ebersole et al. | 422/81 |
| 4,769,333 A | 9/1988 | Dole et al. | 435/287 |
| 4,774,057 A | 9/1988 | Uffenheimer et al. | 422/100 |
| 4,775,629 A | 10/1988 | Kuhl et al. | 435/299 |
| 4,785,407 A | 11/1988 | Sakagami | 364/497 |
| 4,789,526 A | 12/1988 | Matkovich | 422/101 |
| 4,806,313 A | 2/1989 | Ebersole et al. | 422/61 |
| 4,837,159 A | 6/1989 | Yamada | 436/45 |
| 4,844,887 A | 7/1989 | Galle et al. | 422/65 |
| 4,859,603 A | 8/1989 | Dole et al. | 435/287 |
| 4,963,325 A | 10/1990 | Lennon et al. | 422/61 |
| 4,971,913 A | 11/1990 | Manabe et al. | 435/55 |
| 4,975,502 A | 12/1990 | Dole et al. | 422/58 |
| 5,006,309 A | 4/1991 | Khalil et al. | 422/56 |
| 5,031,797 A | 7/1991 | Boris et al. | 222/23 |
| 5,053,197 A | 10/1991 | Bowen | 422/58 |
| 5,084,245 A | 1/1992 | Berke et al. | 422/61 |
| 5,137,808 A | 8/1992 | Ullman et al. | 435/7.9 |
| 5,149,505 A | 9/1992 | English et al. | 422/99 |
| 5,162,237 A | 11/1992 | Messenger et al. | 436/523 |
| 5,167,922 A | 12/1992 | Long | 422/58 |
| 5,219,526 A | 6/1993 | Long | 422/64 |
| 5,264,182 A | 11/1993 | Sakagami | 422/63 |
| 5,272,093 A | 12/1993 | Silva et al. | 436/180 |
| 5,294,404 A | 3/1994 | Grandone et al. | 422/64 |
| 5,311,426 A | 5/1994 | Donohue et al. | 364/413.09 |
| 5,324,481 A | 6/1994 | Dunn et al. | 422/64 |
| 5,332,549 A | 7/1994 | McIndoe et al. | 422/63 |
| 5,358,691 A | 10/1994 | Clark et al. | 422/64 |
| 5,415,994 A | 5/1995 | Imrich et al. | 436/5 |
| 5,424,036 A | 6/1995 | Ushikubo | 422/64 |
| 5,482,861 A | 1/1996 | Clark et al. | 436/48 |
| 5,595,707 A | 1/1997 | Copeland et al. | 422/64 |
| 5,602,037 A | 2/1997 | Ostagaard et al. | 436/69 |
| 5,610,074 A | 3/1997 | Beritashvili et al. | 46/177 |
| 5,627,041 A | 5/1997 | Shartle | 435/7.24 |
| 5,645,114 A | 7/1997 | Bogen et al. | 414/145 |
| 5,700,695 A | 12/1997 | Yassinzadeh et al. | 436/180 |
| 5,737,499 A | 4/1998 | Berstein et al. | 395/82 |
| 5,744,096 A | 4/1998 | Jones et al. | 422/58 |
| 5,769,110 A | 6/1998 | Ohmi et al. | 137/269 |
| 5,773,662 A | 6/1998 | Imai et al. | 436/50 |
| 5,786,182 A | 7/1998 | Catazariti et al. | 435/91.1 |
| 5,817,522 A | 10/1998 | Godman et al. | 436/165 |
| 5,856,193 A | 1/1999 | Fanning et al. | 436/48 |
| 6,042,786 A * | 3/2000 | Oonuma et al. | 422/64 |
| 6,287,783 B1 * | 9/2001 | Maynard et al. | 435/7.1 |
| 6,369,893 B1 * | 4/2002 | Christel et al. | 356/417 |

* cited by examiner

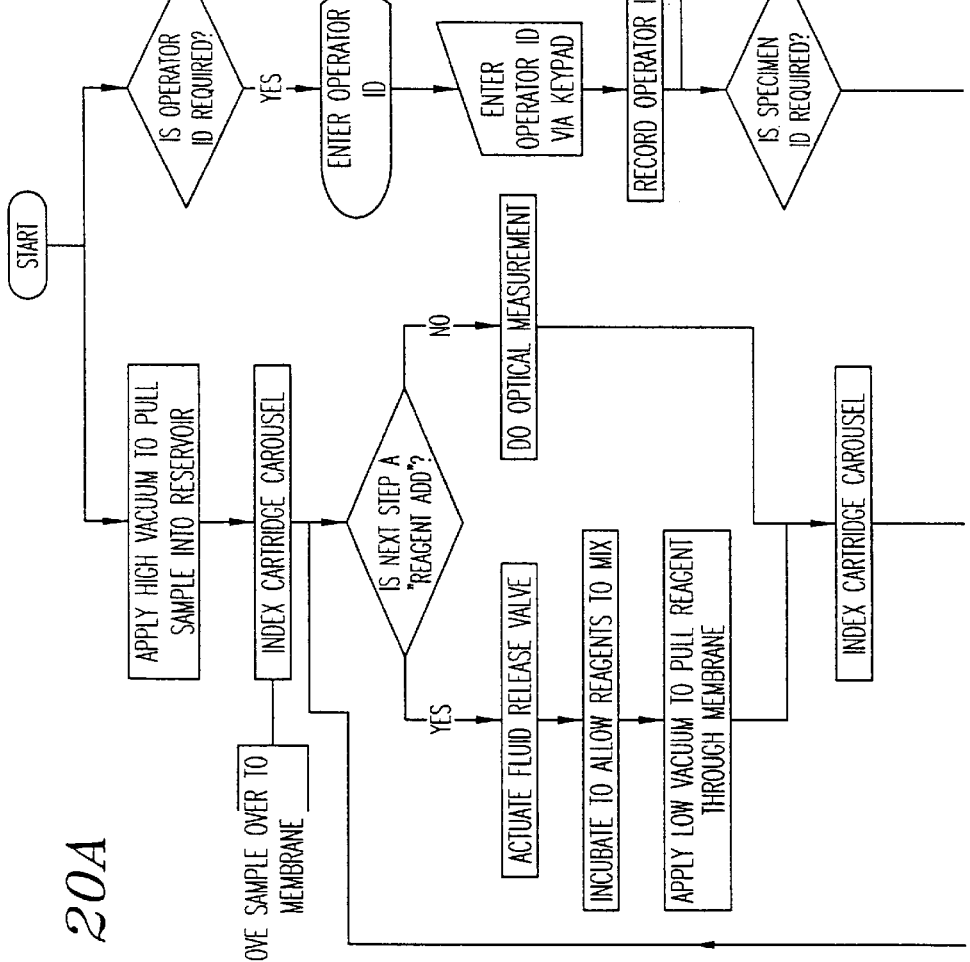

OPERATOR ID REQ'D

SPECIMEN ID REQ'D

REPORT HEADER

NUMBER OF REPORTS

GRADED RESULTS

SET VACUUM TO WEAK LEVEL

SET VACUUM TO STRONG LEVEL

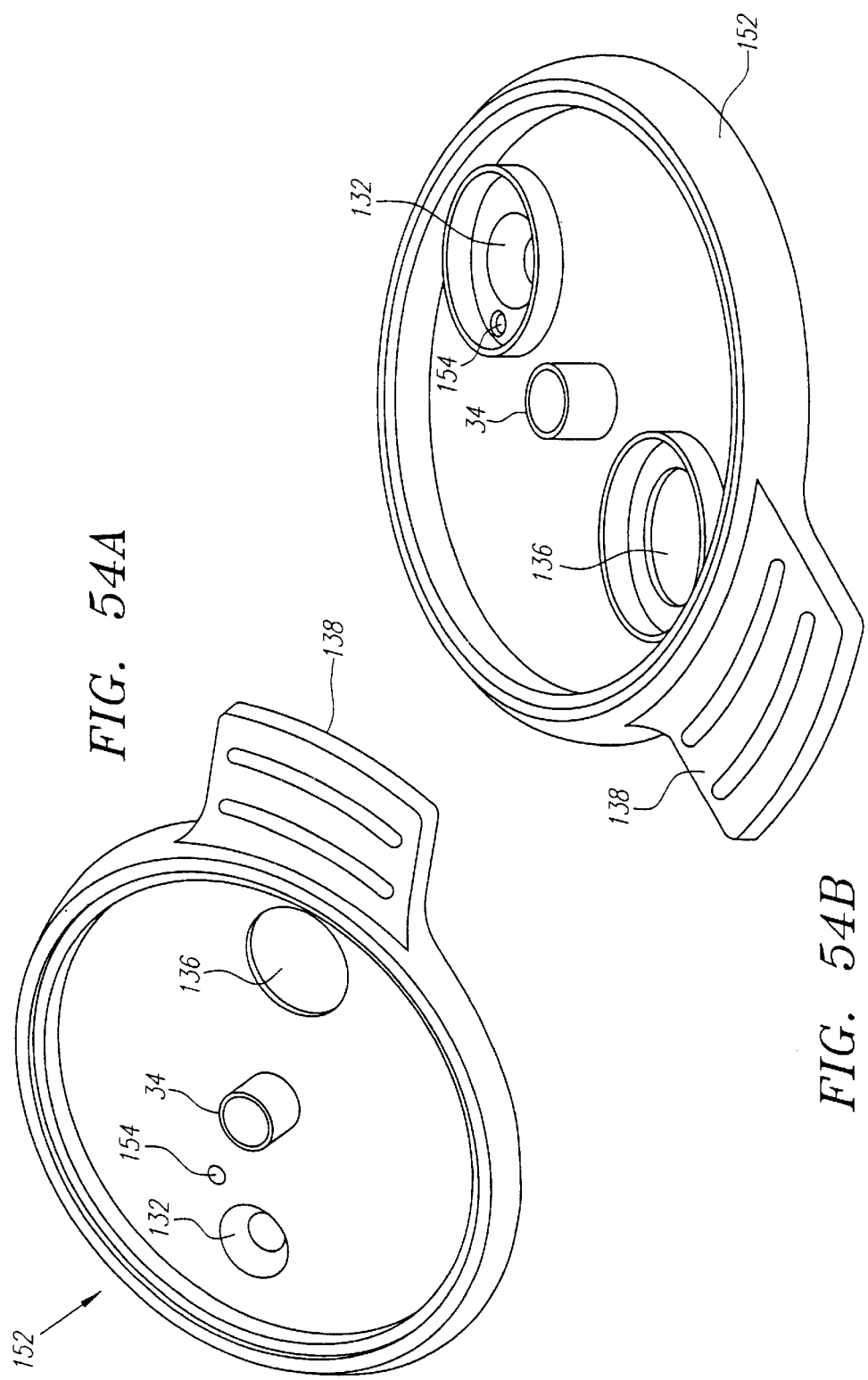

AUTOMATED POINT OF CARE DETECTION SYSTEM INCLUDING COMPLETE SAMPLE PROCESSING CAPABILITIES

This application is related to and claims priority from U.S. provisional patent application No. 60/147,681, filed on Aug. 6, 1999, which is hereby incorporated by reference in its entirety, including all claims, figures, and tables.

INTRODUCTION

The invention relates in part to analytical instruments providing cost effective, automated testing for low to medium sample volume applications. The invention also relates in part to components, features, disposables, reagent delivery systems, accessories, and methods for using such instruments. The analytical instruments of the invention may be used for analytical testing, and in particular, for automated medical diagnostic testing. The invention describes a completely self-contained test surface and reagent delivery device that is used in conjunction with the instrument of the invention to perform an automated sample analysis. The instrument and cartridge system are well suited to the medical point of care testing environment or other analytical testing environments.

BACKGROUND OF THE INVENTION

The following description of the background of the invention is provided simply as an aid in understanding the invention and is not admitted to describe or constitute prior art to the invention.

Conventional automated clinical and chemical analyzers tend to be large, complex, multi-module instruments. For example, U.S. Pat. No. 5,902,548 describes an analyzer for high-throughput analysis. Such analyzers can be expensive, difficult to maintain, and require a significant amount of floor or bench space. Sample-processing is generally handled independent of the analyzer and requires manual placement of the processed sample into the sampling position of the analyzer. Such analyzers are not cost effective for the analysis of low sample volumes nor for providing single test results.

Most conventional analyzers use a modular approach to the various assay functions required to complete an assay procedure. For instance, one module may deliver a test device to a section of the analyzer for sample application. The next module would be used to introduce one or more reagents. Another module may be required to incubate the test device and another one may be required to wash the test device prior to the next cycle of reagent additions. A final module would be used to analyze the result generated within or on the test device. Some devices, such as that disclosed in U.S. Pat. No. 6,042,786 integrate a keyboard as an on-board instrument component. As discussed in U.S. Pat. No. 5,332,549, separate module may be required to remove the spent test device from the analyzer. Such designs require precise placement of the test device to insure proper operation within the analyzer. At the same time, the analyzer conveyance system must allow the test device to be placed and removed without binding within the carrier position. U.S. Pat. Nos. 5,167,922 and 5,219,526 describe an arrangement of test device and carrier features within an analyzer that serve to lock the test device into a carrier. With these types of analyzers the entire test device must be rotated or conveyed to different processing stations.

Many automated analyzers use some form of aspirator in combination with a probe or pipet tip device to automatically draw and dispense a sample or reagent from one container to a test container. For example, U.S. Pat. No. 5,983,734 discloses an analyzer with an aspiration-type sample delivery device. Similarly, U.S. Pat. No. 6,063,340 discloses an analyzer with aspiration and dispensing probes for sample and reagent delivery. To avoid contamination, the tips often must be disposed of after each reagent addition or washed prior to contact with the next solution. Disposing of tips after each use adds a high disposable cost to the instrument. Continuous washing of a reagent delivery system means there is generation of a high volume of liquid biohazardous/toxic waste that must be routinely disposed of. Multiple samplings of a single reagent container increases the possibility that the reagent will become contaminated. If the tip contacts the solution, the sides of the tip or probe may be covered with solution (sample or reagent). The residual solution may then be inappropriately dispensed to the test container or to another reagent container. The contamination of the next reagent may lead to improper assay results not only in the first test being conducted but in all subsequent tests using that reagent container. The use of an aspiration type device means that the reagent containers are exposed to the open environment leading to evaporation issues and potential contamination. Fluctuations in the aspiration system can lead to significant contamination of the entire reagent delivery mechanism and to variable fluid volumes being dispensed. Most systems use multiple sample reagent containers and dispense a unit of reagent with the initiation of each new assay and contain a separate module that contains the actual test device or surface.

Many automated analyzers use centrifugal force for the movement and volume control of reagents. Use of centrifugal force requires a radial array of reagents and precise fluid path constructions. Centrifugal force is used to drive fluid over a barrier and into the next reagent or reaction chamber until a detection member is encountered. High precision molding requirements make individual rotary test devices extremely expensive. Multiple fluid paths and reaction chambers within the fluid path to introduce new reagents and allow incubation time make the design of test devices even more difficult. Subjecting the test device to multiple bursts of centrifugal force can introduce errors in the flow of fluids along the desired pathway. U.S. Pat. No. 5,912,134 discloses an assay cartridge using channels, capillaries, reservoirs, and stop junctions to control reagent delivery, and sample dilution within the cartridge as a function of capillary, gravitational, and centrifugal forces.

A few assay systems have used discrete reagent containers, such as ampules or capsules or bags. The reagents are released by a breaking or piercing mechanism. Reagent delivery is then based on a passive gravity feed and thus can not ensure that the complete volume of the required reagent is dispensed. The breaking or piercing mechanism may also interfere with reagent delivery. If the breaking or piercing mechanism is in contact with more than one reagent container it is possible that it can carryover a reagent that affects the next reagent delivered to the test surface. In some cases, once the piercing member has penetrated the reagent container the fluid flows through a channel within the piercing member to be delivered to the test surface by capillary action or gravity feed. For example, U.S. Pat. No. 5,968,453 describes a reagent cartridge that is open to a sampling device for removal of reagent. Conversely, U.S. Pat. No. 6,043,097 describes a complex reagent container consisting of a sealed lid, and a valve that controls opening and closing of one or more chambers in the container. The reagent chamber holds a glass ampule that is crushed to release reagent, and a filter element.

Other cartridges use a pierceable member to exclude sample from the test cartridge until the member is pierced and then deliver a specific amount of sample by capillary action to the test cartridge. U.S. Pat. Nos. 5,888,826 or 5,602,037 describes a device where downward displacement of a vacuum chuck is used to press down on one section of the test cartridge. Lowering the sample cup of the test cartridge lowers a piercing member into the pierceable member. When vacuum is applied an amount of sample may be aspirated into the sample cup.

U.S. Pat. No. 4,689,204 describes a reagent delivery system that utilizes a series of plunger-like cylinders of varying heights for reagent delivery. As an upper plate-like actuator is depressed onto the various cylinders a sample or reagent is delivered to a reaction tube. The reagent delivery sequence is controlled by the height of the cylinders. The shorter the cylinder the later in the sequence the reagent is delivered. The reaction tube contains a coarse filter between sample addition to the reaction tube and the final reagent delivery to the reaction tube. At the end of the reaction tube is a fine filter to retain the analyte of interest, particularly bacteria. A lens is included in the reaction tube pathway for visualization of the fine filter.

In another embodiment of U.S. Pat. No. 4,689,204, the individual reagent chambers may consist of a piston-like member that when pushed into the reagent chamber drives the reagent past a pressure sensitive seal into a delivery tube. An actuating member pushes the piston-like member that also pierces the seal at the exit port to initiate fluid flow.

In both embodiments of U.S. Pat. No. 4,689,204, sample and reagent flow through the reaction tube is capillary or gravity flow and the actuation of each reagent is based on the linear progression of the actuating member as it passes each piston-like member. Each fluid has only the time between contact of the actuator with it's specific piston-like member to the contact of the actuator with the next piston-like member to flow through the coarse filter and then the fine filter. The design of the coarse filter has a large open or dead volume or head space located above the coarse filter where premature mixing and interaction of the different fluids may occur. In addition this dead volume will retain a significant amount of fluid causing incomplete sample and reagent introduction to the fine filter.

U.S. Pat. No. 5,922,591 discloses an analytical device capable of collecting and analyzing a number of samples in a single unit. A pneumatic system is used to apply differential pressure for fluid movement.

Single use disposal diagnostic devices have been developed for a large number of applications, in particular for medical diagnostic applications. These tests provide timely single test results but require user intervention to produce the test results.

U.S. Pat. No. 5,006,309 describes a disposable device for use in an automated assay system. The device contains two wells. One well is used to process the sample and add reagents. The second well is used to read the assay result. The processed sample is transferred from one well to the other using jets of fluid. The processed sample consists of analyte and microparticles specifically reactive with the analyte. The processed sample is moved between wells without contacting a pipette or other transfer device. The sample well and the read well are connected by a fluid passage and processed sample is moved through the passage by a high velocity wash solution. The wash solution is introduced by a series of nozzles. The read well will retain a specific volume of the processed sample. The read well contains a fibrous matrix that will retain the processed sample. The flow of fluid through the fibrous matrix may be enhanced by the use of a vacuum or absorbent material under the matrix. The microparticle is used to specifically capture and retain the analyte. The fibrous matrix is selected to immobilize the microparticles within the fibrous matrix. Once the particles are immobilized a signal generating material is added to the matrix and the signal produced. The fibrous material must remain porous and support easy fluid flow once the microparticles are immobilized. Sample and reagents are added to the sample well through the use of pipettes and/or transfer devices that rely on aspiration mechanisms and are external to the disposable. Control of the wash solution speed is critical to effective functioning of the device.

Most assay devices or systems do not provide for on board processing of a sample collection device and even fewer systems can process more than one type of sample collection device or process more than one type of sample. U.S. Pat. No. 5,415,994 describes a manual assay device where the sample collection device is a swab. The specimen-containing swab is placed in a well within the assay device. Extraction reagents are added to the well containing the swab and allowed to flow past the swab extracting the analyte from the specimen on the swab. The solution continues to flow through the device to a test surface for analysis. The sample receiving position is joined to a bowl structure. The sample receiving position has a stop feature to properly position the swab above the bowl. The extraction chamber is in fluid contact with a sample receiving zone through an exit port. The matrix of the sample receiving zone defines the flow path from the extraction chamber. The extraction chamber is formed as an integral part of the solid device.

U.S. Pat. No. 5,084,245 describes a similar sample-processing device. The device is designed with a sample detection element in the base. The top of the device covers the sample detection element and contains an elongated feature positioned close to the sample detection element. This elongated feature is used to retain a swab carrying a sample. A number of extensions are contained within the elongated feature and used to squeeze or express fluid from the swab as it is pushed into the elongated feature. The expressed fluid then contacts the sample detection element. The top of the device must be removed to visualize the sample detection element. The extensions from the elongated passageway also serve to direct fluid flow to the surface of the sample detection element. In this invention the swab containing sample is not placed into the sample-processing device until it has been incubated in an extraction reagent and the extraction reagent has been allowed to saturate the fibers of the swab. The swab is inserted in the elongated feature until the tip is in fluid contact with the detection element.

U.S. Pat. No. 5,994,150 discloses an SPR-based detection system for optically analyzing a number of specific regions on a rotating platform.

Each of the foregoing U.S. Patents describing the background of the invention is hereby incorporated by reference in its entirety, including all tables, figures, and claims.

The present invention provides cost effective analytical instruments for determining the presence or amount of an analyte in a sample. The invention provides devices, instruments and methods useful to provide automated test results for single or low to medium sample volume applications, using an instrument that requires only a limited amount of laboratory space. The invention also addresses the technical limitations found in current automated analyzers by providing the analyzer with a test cartridge that contains all of the elements to conduct one or more assays or tests and provide results. The skilled artisan will readily appreciate that the test cartridge design of the invention is such that a number of different optical or electronic methods may be used to detect the analyte or provide a test result. The test cartridge of the invention is also designed to flexibly provide one or more analytical result.

SUMMARY OF THE INVENTION

The analytical, or medical point of care assay instrument and component aspects of the present invention provide self-contained sample processing and reagent capabilities for low to medium volume testing requirements. Representative testing applications include, but are not limited to, infectious disease testing, cancer detection and monitoring, genetic testing, therapeutic drug level monitoring, allergy testing, environmental testing, food testing, diagnostic and/or prognostic testing of human and veterinary samples, off-line process testing, etc. Preferably, the instrument uses an optical detection method based on a fixed polarizer ellipsometric method and a test surface designed for analysis of thin films. Particularly preferred embodiments of such methods and test surfaces are described in U.S. Pat. Nos. 5,494,829 and 5,631,171, which are hereby incorporated by reference in their entirety, including all figures. In certain of these embodiments, the test devices use a combination of thin films to modify the reflection of light from the surface of the test device. Alternatively, the instruments use a detection system, for example a spectrophotometric, chemilluminscent, fluorescent, or electrical potential detection method, that is consistent with the test surface, supporting reagents contained within an assay cartridge, and the signal produced from the test surface.

Assay cartridges are preferably single-use disposable elements designed to conduct a specific type of analysis. Such cartridges contain features that allow for multiple reagents to be stored separately within the cartridge unit. The cartridge also typically contains features that, in conjunction with instrument elements, can result in the delivery of those reagents in the proper sequence to the test surface. In these embodiments, the cartridge is capable of receiving a sample and, in conjunction with instrument elements, processing the sample for application to the test surface. A sample processing element of the cartridge includes the ability to receive and retain a sample collection device, e.g., a swab or a sample reservoir. In preferred embodiments, the sample processing element can retain the sample collection device in a stable configuration as the cartridge, or an element thereof, is indexed or moved to various analysis positions.

The sample processing element can be a separate component that is inserted into the cartridge during manufacturing, or attached by the user immediately prior to use. Alternatively, the sample processing element can be an integral part of the cartridge. Thus, while only a single cartridge design is required, the sample-processing element can be uniquely tailored to accept a wide range of sample collection devices or sample types. The selection of the sample processing element to be inserted into, or otherwise associated with, the cartridge is a function of the specific analysis the cartridge is designed to conduct. The sample processing element can be designed to accommodate a specific sample type, or may be designed to accommodate multiple sample types. In preferred embodiments, the sample processing element comprises a hinged extension designed to support the shaft of a swab-type sample collection device. When used, the hinged extension can prevent the swab shaft from being inadvertently dislodged, and can act as a signal to the instrument that a swab is in use. In other preferred embodiments, a filtration membrane is positioned below a small opening in the sample processing element through which a sample fluid must flow.

Assay cartridges of the invention are also designed to deliver the sample and the assay reagents to a test surface within the cartridge. The assay cartridge, in conjunction with the instrument, may be indexed in a specific sequence to allow the proper addition of reagents to the test surface or other regions of the cartridge. The instrument preferably indexes the cartridge such that the test surface is available for analysis at one or more stages in the assay process. The detection system included in the instrument is designed to be compatible with the type of test surface and reagents contained in the cartridge. For example, when the test surface is a membrane coated with an analyte-specific binding reagent and one of the reagents is an anti-analyte antibody derivatized with a fluorescent label, then the instrument can contain a fluorimeter for analysis. If the test surface is a series of micro-electrodes and the reagents are redox type reagents, the instrument can contain a detection system which provides a potentiometric result. In preferred embodiments, the assay cartridge is capable of generating a signal without addition of external signal-related reagents. For ease of presentation only, the test surface primarily discussed is an optically active test surface. However, those skilled in the art will recognize the flexibility and capabilities of test cartridge design and how to match those properties to a specific detection method within an automated instrument system of the invention.

Thus, in preferred embodiments this invention concerns assay cartridges that preferably comprise a bottom member and a top member, the bottom member comprising an optical reading well and a test surface, and the top member comprising a rotatable reagent carousel. The reagent carousel comprises a sample receiving port and a plurality of reagent wells. The reagent carousel has an opening that is aligned with the optical reading well containing the test surface when an analysis of the surface is to be performed. One or more reagent wells comprise a reagent and a reagent well piston for delivery of one or more reagents to the test surface and/or the sample receiving port. The top member attaches to the bottom member such that the reagent carousel may be rotated relative to the bottom member.

In another aspect, the invention concerns methods for producing an assay cartridge for a specific analysis and sample type. The assay cartridge can be fabricated using manufacturing techniques which are well known in the art. Preferably, the assay cartridge is fabricated by attaching the bottom member to the top member such that the rotatable reagent carousel may be rotated relative to the bottom member. Particularly preferred methods of fabricating the assay cartridges of the invention are described herein.

Yet another aspect of the invention concerns test kits for use with an analytical assay instrument, the test kit preferably comprising a number of assay cartridges specific to the analyte(s) the kit is designed to detect, and instructions for their use. Preferably, the kit includes one or more external kit control elements for additional quality control of the test procedure and equipment. Most preferably, such kits include appropriate sample collection device(s) (e.g., swabs, liquid sampling cups, etc.) which are consistent with the sample requirements for the types of analytes to be detected using the assay cartridges of the kit.

In particularly preferred embodiments, the assay cartridge comprises one or more of the following: (i) a test surface comprising an analyte-specific binding layer for immobilizing an analyte on the test surface; (ii) a test surface that nonspecifically immobilizes an analyte thereon; (iii) a test surface that is an optically active test surface; (iv) an optically active test surface that is adapted to generate an interference, ellipsometric, or polarization signal; (v) a rotatable carousel that further comprises a sample processing element; (vi) a sample processing element comprising a filtration surface; (vii) a sample receiving port adapted to receive a swab type sample collection device; (viii) a bottom portion of each reagent well sealed by a breakable seal material, and a top portion of each reagent well sealed by the reagent well piston in combination with a breakable seal material; (ix) reagent well piston(s) comprising a piercing element to break the breakable seal material sealing the bottom of the reagent well; (x) a bottom member comprising extender tabs or other mechanism adapted to ensure proper registration of the assay cartridge with an analytical instrument; and (xi) reagent well piston(s) comprising a hex boss element.

The assay cartridge is preferably made from a plastic material, such as polystyrene, which provides mechanical strength and stability. The skilled artisan will recognize that such assay cartridges, or components thereof, may be made from a number of thermoplastics which are suitable for injection molding. In preferred embodiments, the bottom member of the assay cartridge is made from a single piece of a plastic material. Most preferably, the bottom member of the assay cartridge comprises an upper and a lower section which are mated together. The top element comprising a reagent carousel can be made from any suitable material, preferably polyethylene that is stiffened with talc, to facilitate handling characteristics during manufacture. The reagent carousel is attached to the top member of the assay cartridge in a manner which allows for rotation of the reagent carousel relative to the bottom member.

The term "sample" as used herein refers to any specimen suitable for analysis within an assay cartridge according to the invention. Preferred sample types include, but are not limited to, a material, including biological material, collected on swabs (e.g., throat, vaginal, endocervical, rectal, urethral, nasal, or nasopharyngeal swabs), fluids, water, urine, blood, sputum, serum, plasma, fecal material, aspirates, washes, tissue homogenates or samples, process fluids, etc.

The term "sample collection device" as used herein refers to any support used for transfer of a sample into the device. Suitable sample collection devices are well known to those skilled in the art. Preferably, a sample collection device can be a swab, a wooden spatula, bibulous materials such as a cotton ball, filter, or gauze pad, an absorbent-tipped applicator, capillery tube, and a pipet.

A vacuum element can be used to express the sample from the sample collection device and to deliver the sample, or a portion thereof, to the optically active test surface. In preferred embodiments, the same vacuum source can be used to secure the cartridge to the instrument's cartridge platform and/or to promote sample and reagent flow through or over or around the optically active test surface. Alternatively, cartridge locking and positioning can also be accomplished by a mechanical element, such as locking mechanisms, or set pins. One or more different vacuum elements may also be used in order to separate the various vacuum functions that may be required to complete a particular assay.

A sample may be processed prior to moving from the sample processing element of the cartridge to the optically active test surface. To process the sample, one or more reagents are added to the sample collection device within the sample processing element. These reagents serve to extract, or free, analyte from the sample collection device and from the sample matrix or from an organism contained on the sample collection device. The reagents may assist in eliminating sample matrix effects such as inhibition or non-specific binding. The sample-processing element may also include a filter feature to remove particulates from a sample prior to introduction to the test surface.

In other preferred embodiments, the sample is processed, for example by filtration with or without subsequent extraction, prior to introducing the sample to the optically active surface. When a fluid such as urine or a suspension contains the analyte, the analyte may be retained on a sample processing element that contains a filtration surface. The sample is added to the sample receiving/processing assembly when the reagent carousel is rotated above an absorbent material located in the base of the cartridge. The absorbent material serves as a self-contained waste reservoir and does not expose other cartridge elements to the waste material. The sample fluid is drawn through the filtration surface by application of vacuum or other pressure differential. Once the sample fluid is filtered, extraction reagents can be applied to the filtration surface. The analyte is then solubilized within the extraction reagent prior to introduction to the optically active test surface. The sample-processing element is indexed to the test surface position and sample delivered. Assay processing proceeds as described herein.

The term "analyte" as used herein refers to any material that is a specific indicator of a disease, infection, drug level, analytical condition, environmental condition, process condition, medical condition, or any other condition that can be diagnosed or assessed by rapid, sensitive detection of the presence or amount of the analyte. Preferably, an analyte is an antigen, antibody, nucleic acid, metal, receptor, enzyme, enzyme substrate, enzyme inhibitor, ligand, chelator, hapten, drug, or analog, or any fragment of these materials.

In further particularly preferred embodiments, the assay cartridge comprises: (i) a sample receiving port capable of receiving a volume of fluid sample onto a concentrating element that is unique to the sample collection device or sample type; (ii) a sample receiving port comprising a retaining mechanism (e.g., molded fingers) to hold a swab type sample collection device in the proper position in the reagent carousel for subsequent processing; (iii) an optically active test surface positioned in the base of the cartridge, consisting of a low porosity material having one or more optical layers positioned thereon to create a surface with the proper optical characteristics for the detection method built into the instrument; and (iv) a reagent carousel in a plastic housing comprising one or more reagents.

The term "sample receiving port" as used herein refers to an opening in the assay cartridge which provides access to the interior of the cartridge. A suitable sample receiving port can be readily determined by one skilled in the art, based on the type of sample and/or sample collection device.

As discussed above, the sample processing element can be a separate component that is inserted into the cartridge during manufacturing or attached by the user, or can be an integral part of the cartridge. The sample processing element is preferably designed to accommodate a specific sample type for a specific test method and analyte. In preferred embodiments, a sample delivery port is fully integrated into a reagent carousel section of the cartridge, and contains an appropriate reagent delivery configuration. In other preferred embodiments, the reagent delivery configuration allows an extraction reagent to flow into a groove or channel at the top of the sample receiving port for extraction of an analyte from the sample collection element.

Preferably, a swab is used as a sample collection device, and the sample processing element comprises a swab holder or a swab processing insert. The swab holder or swab processing insert can be tapered or angled to allow a single sample processing element to accommodate all types of swabs by allowing swabs with different amounts of fiber, or that are wound to different levels of tightness, to be held securely within the holder or insert. Most preferably, the swab holder or swab processing insert securely holds the swab to provide stability during reagent cartridge indexing, and to provide a vacuum seal to assist in fluid flow around and through the swab.

The term "test surface" as used herein refers to a surface within the assay cartridge which is adapted to provide a detectable signal corresponding to the presence or amount of an analyte in a sample. Most preferred are optically active test surfaces, as defined herein. The test surface can be made available to the detector element of the instrument through an optical reading well in the upper section of the assay cartridge. The term "optical reading" well as used herein refers to an aperture or opening in the assay cartridge through which the test surface can be optically read or analyzed by a detector appropriate for the type of signal generated at or by the test surface.

When designing and constructing a test surface according to the invention, it is preferred that such a surface be adapted to specifically bind an analyte of interest, unless an analyte which is nonspecifically immobilized on the test surface can be specifically detected. Therefore, the test surface preferably comprises an analyte-specific binding layer to immobilize one or more analytes of interest on the test surface. The analyte-specific binding layer may be any material that will specifically interact with an analyte in a test matrix and retain that analyte throughout the assay procedure, or until a signal is detected from the test surface. Most preferably, an analyte-specific binding layer can comprise an antibody, antigen, a nucleic acid, enzyme, enzyme substrate, enzyme inhibitor, receptor, ligand, metal, chelator, complexing agent, hapten, or analog, or a fragment of any of these materials. In construction of an optically active test surface, it may be advantageous to add a layer of material to provide long term stability of the analyte-specific binding reagent. This layer is removed during the assay procedure or does not interfere with the assay procedure.

The analyte-specific binding layer may be applied to a test surface, preferably an optically active surface, by a number of different processes. The skilled artisan will recognize that such processes will depend on the nature of the molecules to be employed to specifically bind the analyte(s). In preferred embodiments, the analyte-specific binding layer is coated to the entire surface by submersion in a liquid coating solution, or applied by micro-spotting, ink jetting, or other printing type processes. The analyte-specific binding layer may be applied as a single spot of a specific diameter determined by the volume and viscosity of the coating solution and the wettability of the surface. The analyte-specific binding layer may be applied as a line or other symbol using commercially available processing equipment.

In other particularly preferred embodiments, test surfaces of the invention comprise a plurality of analyte-specific binding layers, each comprising one or more binding reagents specific for a different analyte. Preferably, binding reagents are applied to the test surface in a plurality of zones, thus allowing for the detection of multiple analytes from a single sample in a single analysis. Thus, the analyte-specific binding layer can preferably be applied as a series of stripes, dots, or other symbols in any desired array. The size of the array placed on the test surface is limited by the available test surface area, the spatial resolution required to uniquely identify each position within the array, the detectors spatial resolution capabilities, and the spatial resolution of applying the analyte-specific binding layers. In addition to the analyte-specific binding layer, various analysis controls, e.g., positive and/or negative control zones, can also be applied to the test surface for use in quality control of the test result.

To improve the sensitivity of the testing method, once an analyte is associated with its analyte-specific binding reagent on the test surface, a secondary reagent that includes an analyte-specific binding reagent may be used. This additional analyte-specific reagent may include additional reagents specifically associated with it to amplify the binding of analyte to the optically active test surface or when other surface constructions are used to provide for signal generation. Preferably, these additional reagents are selected from the group consisting of enzymes, film forming particles, catalytic reagents producing an insoluble product, self-assembling molecules, or other materials that will increase the optical thickness of the analyte layer. When the test surface construction does not include optically functional layers, the amplifying reagents are solely responsible for signal generation. If an analyte-specific binding reagent is not used on the test surface, the analyte may be retained by nonspecific interaction with the test surface. Specificity for this type of assay is obtained with a secondary analyte-specific reagent.

The term "optically active test surface" as used herein refers to a test surface which is adapted to alter incident light. Incident light refers to any electromagentic radiation which impinges on the surface. Preferably, incident light is unpolarized light, polarized light, eliptically polarized light, linearly polarized light, monochromatic light, polychromatic light, visible light, ultraviolet light, and infrared light. Methods for preparing an optically active test surface are known to those skilled in the art. Preferred methods for preparing an optically active test surface are described in PCT International Publication Number WO 94/03774 and U.S. patent application Ser. No. 08/950,963, filed Oct. 15, 1997 each of which is hereby incorporated by reference in its entirety, including all figures, or according to similar optical principles. Preferably, the optically active surface is sealed into a position in the base of the cartridge such it is not distorted by the application of the vacuum source. Particularly preferred sealing processes are heat sealing, pressure sensitive adhesives, adhesives, sonic welding, or ultrasonics, and similar processes.

The term "optically functional layer" as used herein refers to a layer (or layers) that can produce a signal upon binding of an analyte to the receptive material. The layer may have one or more coatings, including a base layer with or without an antireflective (AR) layer, designed to modify the optical properties of the support material so that the desired degree of reflectivity, transmittance, and/or absorbance suited to the final assay configuration is obtained. The optically functional layer may attenuate one or more, or a range of wavelengths of light so that a result is observable in an instrumented analysis in the final device upon analyte binding. The attenuation of light may involve the extinction or enhancement of specific wavelengths of light as in an AR coated assay device for a visually observable color change. Or the intensity of a specific wavelength of light may be modified upon reflection or transmittance from the final assay device. The generation of an AR effect is not required for the instrumented detection of the thin film effect. In all cases the optically functional layer serves to attenuate the light incident on the optically active test surface through the interaction of the light with the thin films on the optically active test surface. The optically functional layer may also modify the optical parameters of the device to allow a change in the state or degree of polarization in the incident light. Optically functional layers include amorphous silicon, silicon nitride, diamond like carbon, titanium, titanium dioxide, silicon dioxide, silicon carbide, silicon oxynitride, silicon monoxide, and other related materials or composites of these materials. A preferred construction of optically functional layers is a layer of amorphous silicon coated onto a polycarbonate membrane and then coated with a layer of diamond like carbon. Another preferred construction of the optically functional layers is a layer of amorphous silicon coated onto a polycarbonate membrane then coated with a layer of silicon nitride and a thin layer of diamond-like carbon. Optically functional materials may be applied to the support material by sputtering, ion beam deposition, vapor deposition, spin coating, direct current plasma, chemical vapor deposition, or other methods known to those skilled in the art.

The base optical layer serves to provide the optical characteristics required for creating the appropriate reflectance, adsorption, or transmission properties. It must be sufficiently dense to eliminate stray light leakage or back scattering from the backside of the support. As the thickness of the base layer increases so will the percent reflectance of the modified support. The desired percent reflectivity will depend on the optical system incorporated into the instrument. Appropriate base layer material includes amorphous silicon, polycrystalline silicon, lead telluride, titanium, germanium, chromium, cobalt, gallium, tellurium, or iron oxide. The final optical properties of the optically active test surface are optimized to consider the optical contribution of all layers of the final test surface. Thus, the base optical layer may be adjusted based on empirical testing or thin film reflection theory modeling to account for the attachment layer or the analyte-specific binding layer or any other layer that will be present in the final optically active test surface.

The optically functional layer may serve to provide the desired optical properties and may also serve as an attachment layer. An additional layer may be applied in the construction of the optically active test surface that serves the sole purpose of an attachment layer.

In particularly preferred embodiments, the optically active surface: (i) has an analyte-specific binding reagent immobilized on the surface; (ii) is able to non-specifically capture the analyte to be detected; (iii) is reflective and capable of generating an interference signal upon addition of a specific analyte or target to the optically active surface during performance of the assay steps; (iv) is reflective and capable of generating an ellipsometric signal upon addition of a specific analyte or target to the optically active surface during performance of the assay steps; (v) is reflective and capable of generating a polarization signal upon addition of a specific analyte or target to the optically active surface during performance of the assay steps; and (vi) the interference, ellipsometric, or polarization signal is related to the presence or amount of the specific analyte or target.

An additional attachment layer may be applied to the optical materials to improve their binding and retention of the analyte-specific binding layer or to other types of test surfaces as well. An attachment layer is any material or combination of materials that promote or increase the binding of the receptive material to the optically functional layer. Also, the attachment layer should retain the receptive material with sufficient avidity for all subsequent processing and assay steps. Preferably, the attachment layer should not reduce the stability of the receptive material and should insulate the receptive material from the optically functional layer or layers thereby improving the stability of the receptive material. When no receptive layer is utilized, the attachment layer may be used to non-specifically bind the analyte of interest. Attachment layers can be constructed of silanes, siloxanes, polymeric materials, nickel, diamond-like carbon, and the like. The attachment layer may be applied by vapor phase deposition, solution coating, spin coating, spray coating, a printing-type process, or other methods known in the art. A list of appropriate attachment layers and ways to identify attachments layers is described in U.S. Pat. No. 5,468,606 incorporated herein by reference in its entirety.

The attachment layer should also assist in the stabilization of the analyte-specific binding layer. When an attachment layer is employed, the material can be applied by exposure of the test surface to a vapor of the material under vacuum. Or the layer may be created by solution coating, by spin coating, by ink jetting, by printing processes, or other methods for application of a thin layer of the desired material. Once the material is applied to the test surface, a curing step may be employed to ensure permanent adhesion of the layer to the test surface. Curing is generally accomplished by exposure of the test surface to an elevated temperature for a period of time. The thickness of the attachment layer preferably provides sufficient density to the analyte-specific binding layer and separates the binding layer from the test surface, particularly when an optically active test surface is used. The attachment layer is then applied to the optical materials. The attachment layer may be used in some applications for the nonspecific capture of the analyte of interest. Construction of test surfaces other than optically active test surfaces may not require the use of an attachment layer.

The terms "film" and "thin film" as used herein refer to a one or more layers of sample material deposited on a substrate surface. A film can be about 1 Å in thickness, about 5 Å in thickness, about 10 Å in thickness, about 25 Å in thickness, about 50 Å in thickness, about 100 Å in thickness, about 200 Å in thickness, about 350 Å in thickness, about 500 Å in thickness, about 750 Å in thickness, about 1000 Å in thickness, and about 2000 Å in thickness. Particularly preferred are films from about 5 Å to about 1000 Å in thickness; most preferred are films from about 5 Å to about 750 Å in thickness.

In other particularly preferred embodiments, the reagent carousel: (i) can be freely rotated on the bottom member through about 90°, 120°, 150°, 180°, 210°, 240°, 270°, 300°, 330°, and most preferably 360°, without binding or catching on any other portion of the instrument when the sample collection device is inserted in the sample receiving port; (ii) is mated to the upper surface of the bottom section of the assay cartridge, where the bottom section is formed of two molded plastic articles that may be sealed to create the bottom section of the overall assay cartridge; (iii) the upper surface of the bottom section includes one or more elements such as extender tabs or set pins; and (iv) the bottom surface of the bottom section contains one or more elements such as indentations for ensuring that the cartridge is in the proper position and orientation to conduct the assay method as well as improve the users' grip on the test cartridge when loading on the instrument.

The term "extender tabs" as used herein refers to elements which extend from the assay cartridge and assist in orienting the cartridge within the instrument. Extender tabs are in the raised position in the final assembled assay cartridge and serve to lock the reagent carousel into place. When the cartridge is in proper registration within the instrument, the tabs are pushed down and the reagent carousel is free to rotate. The cartridge may be held in place in the instrument by a variety of mechanisms well known in the art. Preferred means of providing alignment and stability of the cartridge can be application of vacuum, by means of force applied by a presser foot, release arms and/or by a lock and key type matching of the cartridge bottom to the instrument cartridge slot, or simple matching of set pins of sufficient height to stabilize and retain the cartridge.

In other particularly preferred embodiments: (i) reagents are sealed within the reagent carousel by a thin layer of a breakable vapor seal material at the bottom of a reagent well; (ii) reagents are sealed within the reagent carousel by a thin layer of impermeable, vapor seal material at the upper opening of the reagent well; (iii) the upper reagent well seal is in contact with a reagent well piston; (iv) the reagent well piston is a rigid (e.g., plastic) element designed with a receiving element for a plunger element for driving the piston (e.g., a hex boss) in the uppermost segment of the piston, such that the uppermost segment of the piston extends above the upper surface of the reagent carousel section of the cartridge; (v) the hex boss is designed to mate with a push rod of the plunger element in the instrument housing; (vi) the push rod mates with the hex boss, or other receiving element of the piston, and a vertical drive element pushes the piston through the lower impermeable vapor seal to release reagent onto the optically active surface; (vi) the plunger element draws the piston back into the upper position to allow proper motion of the cartridge to the next assay position; and (viii) the plunger element includes an optional presser foot to improve registration of the reagent carousel and the membrane holder within the cartridge.

In another particularly preferred embodiment, the reagent well piston is pushed down with a plunger element, but is not equipped with a receiving element for said plunger. Instead, the plunger pushes the piston by contacting the uppermost surface of the piston without mating to a element such as a hex boss. As the plunger does not mate with the piston, it does not draw the piston back into the upper position, but allows it to stay in the depressed position.

The term "vapor seal material" as used herein refers to a breakable sealing material which provides a liquid- and vapor-impermeable barrier at the top and/or bottom of each reagent well. The vapor seal material is intended to be broken by application of force by a reagent well piston at an appropriate point in the assay procedure, in order to provide flow of reagent. Suitable vapor seal materials are well known to those skilled in the art. Particularly preferred vapor seal materials are mylar and low density polyethylene. In preferred embodiments, the vapor seal material is affixed to the reagent well by an adhesive. The vapor seal material may also comprise additional layers of material such as foils, papers, additional plastics, and the like. Preferably, the vapor seal material comprises a layer of 15 pound polyethylene, a layer of aluminum foil, a layer of 7.2 pound polyethylene, and a layer of 25 pound ClF coated paper (Genesis Converting Corporation). Those skilled in the art will recognize that other materials of similar composition may substitute in the vapor seal material.

The term "reagent well" as used herein refers to a chamber in the carousel that contains a reagent for use in an assay procedure. A reagent may be any suitable reagent, including but not limited to a wash reagent, a buffer reagent, an extraction reagent, a neutralizing reagent, an amplifying reagent, or a signal generating reagent, as defined herein.

The term "reagent well piston" as used herein refers to an element that provides positive pressure to the reagent well for delivery of a reagent. A preferred material for the reagent piston is polycarbonate. The reagent well piston is pushed by a plunger mechanism of the instrument, creating sufficient force to break the lower seal of the reagent well and deliver fluid from the reagent well. The reagent well piston may contain an element to ensure positive engagement by the plunger mechanism. In a preferred embodiment, the element that ensures positive engagement is a hex boss. The reagent well piston may comprise a piercing element to assist in breaking the lower reagent well seal. The reagent well piston may or may not need to be retracted back into the reagent well once it is used to pierce the reagent seal, depending on the carousel design and whether the piston will prevent reagent carousel rotation. A piston design that need not be retracted may not require the hex boss element, as it need not seat with the push rod mechanism. The reagent well piston can also serve to assist in sealing the upper portion of the reagent well.

The piston design, the rate that the plunger mechanism displaces the piston in the reagent well, and/or the aperture size for the reagent well can allow for control of the reagent flow to the test surface. Piston design and displacement can also be used to control the amount of reagent delivered to the test surface. The piston may be designed with grooves of various shapes and sizes and numbers. The contour and number of grooves in the piston will modify the fluid flow rate through interactions such as surface tension and retention of the fluid contact with piston material as the piston is displaced. The piston design and the rate of displacement, as well as the materials in the lower vapor seal, determine the aperture size for the dispensing of the reagents. The quality of the aperture is also important in determining fluid flow rate. The quality of the aperture generated means the size of the opening, the structure of the opening, the cleanliness of the opening, etc. The piston design and the lower vapor seal as well as the displacement rate of the piston must be evaluated together to optimization reagent dispensing.

The term "hex boss" as used herein refers to a raised element at the top of the reagent well piston comprising a hexagonally-shaped recess. In preferred embodiments, the plunger mechanism mates with the hexagonal recess to ensure positive engagement of the reagent well piston by the plunger. Those skilled in the art will recognize that the recess need not be hexagonally shaped, but rather can be any shape which is capable of mating with the plunger mechanism. The plunger mechanism can also be designed with spring-loaded mechanisms to control the push rod. Release of tension on the spring mechanism allows the push rod to displace the piston. If different pressures are required to break the reagent seals concentric push rods can be designed with different spring tensions to deliver varying displacement capabilities.

In another aspect, the invention concerns analytical instruments that comprise or utilize assay cartridges according to the invention, a mechanism, element or subassembly for receiving the assay cartridge, one or more rotation elements or subassembly to rotate and index the reagent carousel, a plunger element or subassembly for engaging the reagent well pistons to deliver reagent from the reagent wells to the sample receiving port and/or the test surface, a vacuum element or subassembly for directing sample and/or reagent to the test surface, and a detector for detecting a signal from the test surface. Preferably, a control processor controls the rotating, plunger, and vacuum elements according to an assay algorithm, and a signal processor for relating the generated signal to the presence or amount of an analyte.

In particularly preferred embodiments, the analytical instruments of the invention comprise one or more of the following: (i) a presser foot for stabilizing the assay cartridge; (ii) an optical control element for determining cartridge orientation; (iii) a rotation element comprising a mechanical arm and motor; (iv) a plunger element comprising a push rod attached to a vertical drive element; (v) a push rod adapted to seat in a hex boss element on the reagent well piston; (vi) a push rod that returns the reagent well piston to about its original position in the reagent well following delivery of the reagent; (vii) a detector selected from the group consisting of a color sensor, a color detector, an image detector, a spectrophotometer, a luminometer, a fluorometer, a potentiometer, an interferometer, a polarimeter, and an ellipsometet; (viii) a detector that is a fixed polarizer ellipsometer; (ix) a control processor and a signal processor consisting of a single general purpose computer programmed to perform instrument control and data processing algorithms; (x) an assay cartridge comprising an identifying element which identifies the analyte and/or the sample to the analytical instrument; (xi) an assay cartridge comprising an identifying element that is a bar code, and a bar code reader configured to read the bar code; and (xii) a sample receiving port adapted to receive a swab type sample collection device.

The analytic instruments preferably comprise an element for detecting a signal from the test surface. Depending upon the type of assay to be performed, the detector can be a color sensor, a color detector, an image detector, a spectrophotometer, a luminometer, a fluorometer, a potentiometer, an interferometer, a polarimeter, and an ellipsometer. One skilled in the art can readily match a suitable detection element to the assay being performed. Most preferably, the detection element is a fixed angle ellipsometer.

The term "interference signal" as used herein refers to a change in the wavelength ("color") of light reflected by an optically active surface, due to changes in the optical thickness of the sample material adsorbed or specifically bound to the surface. Interference may be measured and related to the presence or amount of the specific analyte or target by techniques that are well known in the art.

The term "ellipsometric signal" as used herein refers to a change in the elliptical polarization of light reflected by an optically active surface, due to changes in optical thickness of the sample material adsorbed or specifically bound to the surface. An ellips6metric signal may be measured and related to the presence or amount of the specific analyte or target by techniques that are well known in the art.

The term "polarization signal" as used herein refers to a change in the linear polarization of light reflected by an optically active surface, due to changes in optical thickness of the sample material adsorbed or specifically bound to the surface. A polarization signal may be measured and related to the presence or amount of the specific analyte or target by techniques that are well known in the art.

In particularly preferred embodiments, the analytical instrument: (i) comprises a user interface element; (ii) comprises a control processor; (iii) comprises a signal processor; (iv) comprises an algorithm for signal processing and data classification; (v) comprises an algorithm for determining an assay sequence; (vi) receives one or more assay cartridge(s) and completes the assay protocol independent of the user; (vii) mechanically indexes the assay cartridge so that the optically active surface of the cartridge is available for analysis at one or more stages in the analysis process; (viii) comprises a carousel rotation element consisting of a mechanical arm and a motor which indexes the reagent carousel to different positions for delivery of reagents to the optically active surface of the cartridge in the appropriate sequence; and (ix) comprises one or more optical control elements, such as optical encoders or bar code readers, for reagent carousel indexing, cartridge positioning, and determining cartridge orientation, and establishing the analytical method to be used and type of result to be reported.

The term "user interface" as used herein refers to an element of the instrument which allows the user to provide information and/or instructions to the device, and/or for the device to provide information and/or instructions to the operator. Those skilled in the art will recognize appropriate user interfaces. For example, a user interface can be one or more of the following: a bar code reader, a keyboard, a computer "mouse," a light pen, a computer screen, and a computer printer.

The term "algorithm" as used herein refers to a sequence of steps to be followed to perform an assay and/or analyze data obtained from an assay. In preferred embodiments, an algorithm is stored on a control processor which controls the operation of the analytical instrument, and/or a signal processor which processes a signal generated from the test surface into a meaningful assay result. Preferably, the control and signal processors are one or more general purpose computer elements or computer chips which are programmed with the appropriate algorithm.

The term "daemon" as used herein refers to a process that occurs in the background and is invisible to the user. Preferably, daemons run continuously throughout the assay procedure. A daemon may also be referred to as a background procedure or a background thread of execution.

The term "index" as used herein refers to positioning of an assay cartridge in specific orientations. A cartridge can be indexed so that discrete locations on the cartridge, for example a reagent well and the test surface, precisely align with one another for properly timed and/or positioned reagent delivery. Preferably, analytical instruments of the invention use a mechanical mechanism or subassembly for cartridge indexing.

The term "optical control elements" as used herein refers to a optical sensor mechanism which determines the orientation of a cartridge element. Appropriate optical control elements are well known in the art.

Preferably, one or more parameters required for proper sample processing can be provided by the user through the user interface of the instrument. For example, a user may indicate the sample type, the type of sample collection device, and/or the assay protocol. Most preferably, however, the assay cartridge is configured during manufacture such that each combination of assay type, sample collection device, etc., is represented by a distinct assay cartridge which can be recognized by the instrument and distinguished from other cartridges. The distinct assay cartridge can provide the appropriate reagent carousel for the assay, as well as the sample retention and extraction mechanism required by a given sample collection device. For example, for swab-type sample collection devices, a sample retention mechanism must also serve to direct extraction fluid into the swab fibers and not just around the swab fiber. Assay sequence, incubation times, and other parameters can be pre-set for each cartridge design. Cartridge lot information may also prompt the instrument to select the proper assay parameters and sequence as well as data analysis method. Alternatively, data processing may occur manually by the user.

In other particularly preferred embodiments, the vacuum element of the analytical instrument: (i) comprises a single vacuum source having one or more vacuum ports; (ii) uses vacuum for cartridge retention and stability, reagent flow through, sample extraction, and test surface drying; (iii) uses vacuum to direct fluid to flow through or over or around the optically active surface and into a waste adsorbent material or reservoir within the cartridge; and (iv) incubates a sample, or a component thereof, on the surface of the optically active surface for a period of time under normal gravity conditions prior to reagent transfer through or around the optically active surface by vacuum.

Preferably, the vacuum source maintains a weak (about 20 mm Hg to about 40 mm Hg; preferably about 30 mm Hg) vacuum when the test surface is positioned for reading through the optical reading well. In other preferred embodiments, the vacuum source is disengaged during incubations on the test surface and/or when the reagent carousel is indexed. The vacuum level can preferably be raised to between about 120 mm Hg and about 180 mm Hg, most preferably about 150 mm Hg, in order to dry the test surface prior to reading, to draw extraction reagent from a swab, or to draw a fluid through a concentrating membrane prior to extraction. One skilled in the art will recognize that the vacuum required for reagent flow can vary, depending on the composition of the reagent and the composition and porosity of a membrane, filter, or test surface. A feedback loop to vary the vacuum level dependent upon sample or test conditions may be incorporated to automatically adjust the vacuum in the device to accommodate a number of parameters affecting reagent flow.

In further embodiments, a series of pneumatic valves may be added under the cartridge receiving stage of the instrument. These pneumatic valves allow the introduction of air into or over various parts of the cartridge or instrument. The air flow may be directed onto the optically active test surface to assist the vacuum system in drying the test surface. Or the air flow may be used to assist in fluid movement.

In other particularly preferred embodiments: (i) the instrument uses fixed angle ellipsometry as the optical analysis feature; (ii) the instrument comprises an LED light source; (iii) the LED light source emits light at 525 nm; (iv) the LED light source is positioned at a 20° angle of incidence relative to a line normal to the plane of the optically active test surface; (v) a photodiode detector is positioned at a 20° angle of detection relative to a line normal to the plane of the optically active test surface; (vi) polarizing and analyzing polarizers are positioned at 90° relative to one another; and (vii) the instrument allows for synchronous detection to eliminate stray light as a source of noise.

The term "light source" as used herein refers to any source of electromagnetic radiation. Electromagnetic radiation can also be referred to as "light." Such electromagnetic radiation may include wavelengths from about $10^{-6}$ μm to about $10^8$ μm; preferred is electromagnetic radiation from the ultraviolet to infrared wavelengths; particularly preferred electromagnetic radiation is visible light. Suitable light sources are well known to those skilled in the art, and can include any source of monochromatic or polychromatic radiation. The use of monochromatic radiation is preferred. The terms "monochromatic radiation" or "monochromatic" light as used herein refer to electromagnetic radiation having a bandwidth that is sufficiently narrow to function as a single wavelength for design purposes. Preferred light sources are lasers, laser diodes, and light emitting diodes (LEDs). In preferred embodiments, an aperture, preferably a bar-shaped aperture, is placed in the optical path, oriented parallel to a stripe-shaped capture zone on the test surface. The aperture can provide a larger interrogation area of the test surface, rendering the detector less susceptible to surface variations in the test surface and providing a larger area over which signal is averaged.

As used herein, the term "detector" refers to any device for detecting electromagnetic radiation by the production of electrical or optical signals, and includes color sensors, color detectors, image detectors, spectrophotometers, luminometers, fluorometers, potentiometers, interferometers, polarimeters, and ellipsometers, whether these detectors are driven to provide analog or digital signals, as well as any other light detection device. Preferred detectors detect electromagnetic radiation, particularly visible light, with the resulting production of electrical or optical signals. A signal processing element can process these signals to yield this information, for example by the use of standard curves, to associate the signals with an optical film thickness. In especially preferred embodiments, the optical film thickness is interpreted as a binding assay result, e.g., the result of a test showing either a positive, negative, or inconclusive result in a test for a specific analyte.

Preferably, the light source and detector of the instrument are positioned at an angle of incidence of between about 10° and about 40° relative to a line normal to the plane of the optically active test surface. Most preferably, the angle of incidence is about 10°, 20°, 30°, and 40°.

The term "polarizer" as used herein refers to a device that receives incoming electromagnetic radiation, and produces therefrom radiation which is polarized. Suitable polarizers, such as polarizing filters and analyzers, are well known to those skilled in the art. As described herein, polarizers can be positioned to polarize incoming light from the light source prior to contact with the sample under study, as well as light reflected from the sample under study. A polarizer can be fixed within an optical pathway. Alternatively, one or more of the polarizers can include a mechanism for varying s- and p- components of polarized light with time by rotating the polarization element, or a component thereof, on its optical axis. Preferably, this mechanism rotates a polarizing filter that is located in the position of a polarizer or analyzer in a conventional ellipsometer. Rotation of a polarizing filter provides a corresponding quasi-sinusoidal intensity in the electromagnetic radiation that is reflected from the sample under study.

The terms "polarizing polarizer" and "analyzing polarizer" as used herein refer to polarizers which interact with incident light prior to and following light impinging on the optically active test surface. In preferred embodiments, the polarizing and analyzing polarizers are set at about 70° to about 110° relative to one another. Most preferably, the polarizing and analyzing polarizers are set at about 70°, 80°, 90°, 100°, and 110° relative to one another.

The term "linear polarization" as used herein refers to a polarization state that is essentially all s-polarization or all p-polarization. Electromagnetic radiation is linearly polarized if, in either linear state, there is not enough of the other polarization state to affect the outcome of the measurement. Preferably, a linear polarizing filter may be rotated up to about 20° rotation off of its optical axis without introducing appreciable measurement errors.

In another aspect, the invention concerns methods of determining the presence or amount of an analyte in a sample. The method comprises providing an assay cartridge and an analytical instrument as defined herein, placing the sample into the sample receiving port of the assay cartridge, placing the assay cartridge into the receiving mechanism of the analytical instrument, performing an assay using the analytical instrument according to an assay algorithm, and using the signal processor to determine the presence or amount of the analyte in the sample.

In particularly preferred embodiments, a sample is selected from the group consisting of a throat swab, a vaginal swab, an endocervical swab, a rectal swab, a urethral swab, a nasal swab, a nasopharyngeal swab, a fluid, water, urine, blood, sputum, serum, plasma, an aspirate, a wash, a tissue homogenate, and a process fluid.

The preferred methods of using the instrument and cartridge include methods for analyzing the data and reporting a result. Preferred methods of use will be described in terms of a reagent or assay cartridge that is designed to detect an analyte on an optically active test surface where the optical detection system is based on a fixed polarizer ellipsometer. Those skilled in the art will recognize that methods for use of the instrument and the reagent cartridge will be similar for any other combination of analyte, test surface, and detection system.

In using the system, a user selects the reagent cartridge designed for the analyte of interest, for example a reagent cartridge designed to detect a particular microorganism. In particularly preferred embodiments, a microorganism is a bacterium, a virus, or a fungus, and most preferably a pathogenic bacterium, virus, or fungus. The user provides a specimen from the patient to be tested for the analyte of interest, collected, for example, using a throat swab. The user enters or scans (e.g., by bar code) the specimen identification number and the reagent cartridge lot information. Alternatively, the instrument may read the bar code on the top, side, or bottom of the cartridge when it is placed in the instrument. A bar code, or other identifying element of the cartridge, can provide information to a "Dallas" chip which provides the instrument with assay a quality control parameters, a lot number, a sample type, etc. The user places the throat swab in the sample receiving port in the reagent cartridge and loads the cartridge into the instrument. The instrument may close a door behind the reagent cartridge for orientation and stability or it may pull the cartridge into the appropriate slot with a cassette player type mechanism. The cartridge may be placed or set on alignment or set pins formed on and above the cartridge receiving stage. The set pins assure that the cartridge is properly oreinted. The rotation element may serve as one of the set pins. Preferably, the instrument receives the cartridge in proper registration and alignment so that the cartridge may be mechanically indexed through the appropriate sequence of reagent additions and incubation steps. The user may then enter a "start analysis" command via the user interface of the instrument, or the optical sensor that detects the presence of a cartridge may cause the initiation of the assay protocol.

The instrument then rotates the reagent carousel into a position so that the optically active surface may be scanned to provide a baseline reading. The optical scanning procedure may be conducted on one or more fixed points within the optical reading well or may be a linear segment of the optically active test surface or may analyze the complete test surface. The optical detection system does not move but the cartridge may be linearly displaced to expose a new section of the optically active test surface at each reading point.

A possible reading scheme occurs as follows. The collected data is stored for use in the final data analysis routine. For the baseline scan the cartridge is rotated to the optical read window. The cartridge is moved along the instruments positive y-axis so that the beam spot is positioned on the outer edge of the read area's periphery. The cartridge is moved along the negative y-axis and readings are taken every 12.7 microns. The sample size is dependent on the beam size and configuration and the number of samples per unit area needed to provide the accuracy desired in the final result. The raw data is stored in a file. The first column of raw data is the position of the read area on the optically active test surface. The second column is the corresponding reflected signal in millivolts for the baseline scan. The same process is repeated at appropriate assay steps. The multiple reads provide QC checks of the test cartridge and can stop a test if the readings at a specific stage fall out of a pre-set range. The multiple reads per assay allow for a test generating high noise to be rejected earlier in the analysis process.

The data analysis software can then align multiple scans of the same surface by selecting an edge feature to align each scan relative to the other scans, and thus provide for proper data comparisons. The edge features can be eliminated from the data analysis routine. The readings can be taken at any index distance desired and the degree of overlap selected to provide the most accurate level of result. It should, however, be set at the minimal acceptable value as the number of measurements made will also affect the time to result. The final method of data analysis can be tailored to the type of test method used, the required accuracy and precision, and other parameters determined by the intended use of the test result. Acceptable data analysis routines are known to those skilled in the art but could include peak to peak comparisons, peak smoothing, or other methods for normalizing the collected data or methods for data reduction. Another option might be to do image processing of the surface. In this case, each scan taken will visualize the entire test surface. Images would be compared between scans and appropriate data selected to provide the final test result. One or more of the detection scans described in the previous procedure may not be required for all detection methods and detection surfaces. However, one or more scan is required to provide sufficient information for data normalization.

Once the baseline scan is complete, the instrument activates the extraction reagent well and causes an extraction reagent to flow into the sample receiving port. The reagent carousel will be indexed by rotation to align the sample receiving port over the optically active test surface. Following a pre-set extraction period, the vacuum system can draw the sample fluid from the sample collection device through a filter to remove particulates, and onto the optically active test surface. Vacuum must be applied to the sample processing element such that sample fluid or processed sample fluid is drawn through the filter of the sample-processing element and onto the optically active test surface without being drawn through the optically active test surface. This is achieved by placement of a vacuum port between the sample-processing element and the optically active test surface so that the fluid will only flow to the optically active test surface and not through, over, or around it.

Following sample addition and a pre-set incubation, the reagent carousel rotates to align the proper reagent well with the optically active test surface. The sample may be added in the presence of a neutralizing agent that is added to the test surface prior to the addition of sample from an appropriate reagent well. The plunger mechanism of the instrument forces the piston to break the reagent seal and deliver the fluid to the optically active test surface. By using the piston and plunger mechanism, the flow rate of reagent delivered to the test surface can be controlled. Fluid is positively displaced by the piston and delivered to the optically active test surface under gravity and positive displacement. In this case positive displacement does not include any aspiration or introduction of air but is a mechanical method for positive displacement. The reagent will combine with the test sample on the surface of the optically active test surface. Following a pre-set, static incubation period, the fluid will be drawn through or over or around the optically active test surface by activation of the vacuum system and all liquid waste is retained within the assay cartridge. When analyte is present in the neutralized sample, analyte will bind in one or more positions to the analyte-specific binding layer on the optically active test surface. After specific reagent additions, the test surface may be washed with a solution from one or more reagent wells to remove any unreacted reagents. After wash steps the test surface may be dried by a combination of vacuum and air flow, by vacuum alone, or by air flow alone.

Next, a new reagent well aligns over the optically active test surface and a wash solution is delivered. All reagent additions occur with the vacuum system in the disengaged position. Once the reagent is delivered and the pre-set period is past, the vacuum system is engaged to draw the fluid through or around or over the optically active test surface. Reagent removal is controlled by application of the vacuum. The static incubation improves assay performance while the flow through process simplifies assay processing. The test surface may be rinsed with one or more wash reagents from one or more reagent well. Once the optically active test surface is rinsed, the reagent carousel is rotated to the optical reading well and the optically active test surface is scanned again to look for non-specific binding and debris from the sample and to qualify the optically active test surface integrity. A scan following the addition of sample is required to assist in normalizing the data. An amplifying or signal-generating may also be added to the test surface together with the analyte when appropriate for the type of test surface employed.

Upon completion of the second optical scan, an amplifying reagent, or signal generating reagent (depending on the test surface) can be applied to the optically active test surface by rotation of the appropriate reagent well over the test surface. The amplifying reagent is allowed to react for a period of time and then the vacuum system is engaged to draw the unreacted reagent through or around or over the optically active test surface. The reagent carousel is again rotated to align a reagent well over the test surface and a wash solution applied. The reagent seal is pierced as with the original reagent delivery and the vacuum is engaged at the appropriate time. The vacuum will serve to dry the optically active test surface. A small air-flow device may be included to improve the speed of the surface drying. When a test surface is not optically active then this final drying step may not be required.

Once the optically active test surface is washed and dried then a final optical scan is conducted. The optical reading well of the reagent carousel is rotated over the test surface and the scan conducted. The optical scans may occur with the vacuum system engaged if no distortion of the test surface occurs under vacuum. Positive report of analyte binding is provided only when sufficient signal intensity is observed and the proper sequence of elements on the test surface are identified.

The instrument component list preferably includes an optical detection element preferably contained in a single common unit that may be attached to the instrument support structure; a plunger assembly that again is a single unit with all of the required functionalities built in; a cartridge carriage unit that provides for orientation, retention, and positioning of the cartridge within the final assembled instrument; a support structure designed to position and stabilize all of the functional units of the instrument and which may assist in placement and movement functions of the instrument; a vacuum system; one or more motors to drive the positioning of the plunger and the cartridge, etc; and electronic components to control, monitor, and report on the various functions and measurements made by the instrument.

Most preferably, the assay cartridge can be manufactured as follows. The cartridge consists of the following molded pieces: the carousel, the pistons (one or more designs), the test surface holder (top), the waste reservoir holder (bottom), the sample receiving port, and an attachable hinged swab retention element (when required). The test surface holder has an opening and the optically active test surface is heat sealed to the bottom of the opening so that the optical surface is exposed through the opening. The optically active test surface is created by applying the optical coatings and other layers required for proper optical function and then coated with the appropriate analyte specific capture reagents before it is ready to attach to the test surface holder. The waste reservoir has positions for one or more adsorbent pads of highly adsorbent material to be placed within the wells in the floor of the part. These two pieces may be heat sealed, glued, or snapped together to provide the platform piece of the final assembled cartridge. The reagent carousel has the upper vapor seal applied by heat sealing the polyethylene layer of the vapor seal to the plastic carousel at a number of points, e.g., around each reagent well and at the edges of the carousel. The plastic pistons are loaded onto the reagent well and then the reagent well is filled with reagent. Then the lower vapor seal is then applied to the cartridge. The lower vapor seal has an opening that corresponds to the sample receiving port and a cutout that corresponds to the reading well. At the under side of the carousel and where the vapor seal has an opening one or more membranes (gradient membranes, single-pore size membranes, Memtex® membranes, etc.) are heat sealed to the under surface of the sample receiving port and then an adhesive, plastic gasket is applied over the membranes to assist in the establishing of vacuum during use. If the sample receiving feature is not an integral part of the mold then the element can feature a snap fit into position within the carousel. The carousel is then attached to the lower platform element of the cartridge. The entire cartridge may be wrapped in a vapor proof bag or may be placed in a kit as individual unwrapped units.

BRIEF DESCRIPTION OF THE DRAWINGS

FIGS. 54a–54d depicts one possible bottom configuration of the test cartridge.

DETAILED DESCRIPTION OF THE PREFERRED EMBODIMENTS

The Assay Cartridge

Figure 1:
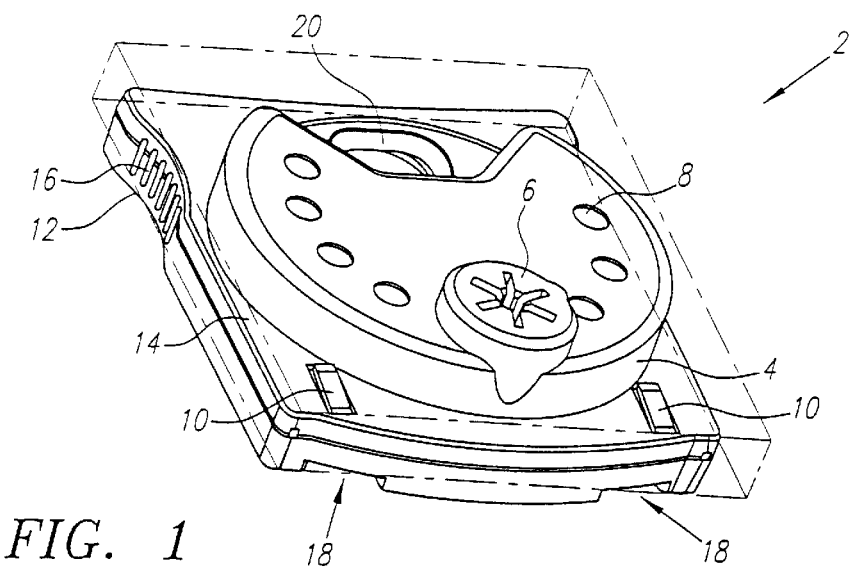
FIG. 1 depicts a top on view of a representative assay cartridge.

FIG. 1 depicts an assembled test cartridge for use with the instrument of this invention. The assembled cartridge 2 includes an optical reading well 20, a sample-processing element 6, a reagent carousel 4, and reagent wells 8. In the depicted embodiment, the test cartridge also includes optional finger grips 16, cartridge locking features 10, and cartridge/instrument registration features 18. Also in the depicted embodiment, the bottom member of the test cartridge is made of two separate molded pieces. Bottom section 12 is the bottom-most piece of the cartridge assembly, and is designed to accept and retain an absorbent material for the isolation of waste sample and reagents during the assay process. The upper section 14 of the bottom of the test cartridge contains the optical reading well and an aperture at the bottom of the optical reading well to allow the optically active test surface to be fused or otherwise attached to the bottom of the aperture. Preferred methods for attaching the test surface are heat sealing, heat staking, or an adhesive process. The complete test cartridge consists of a top member reagent carousel 4, a sample-handling or processing element 6, and the two pieces of the bottom section 12 and 14. Optional finger grips 16 are extended ribs from the surface of parts 12 and 14 at the indented portion of the cartridge side walls. The indentation and the finger grips 16 are included to facilitate cartridge loading and handling by the user. When the optional carousel locking extender tabs 10 are in the up position, a locking mechanism engages the cartridge so that the cartridge is not free to rotate. When the cartridge 2 is in proper registration with the instrument, the tabs 10 are depressed and the carousel 4 is released and can be rotated. Rotation of the reagent carousel 4 allows the reagent wells 8 to be aligned in the proper sequence over the optical reading well 20 and the optically active test surface at the bottom of well 20. Rotation of the reagent carousel 4 also allows the sample-processing device 6 to be aligned over the optical reading well 20 and thus the optically active surface at the proper time.

The Reagent Carousel

Figure 2A:
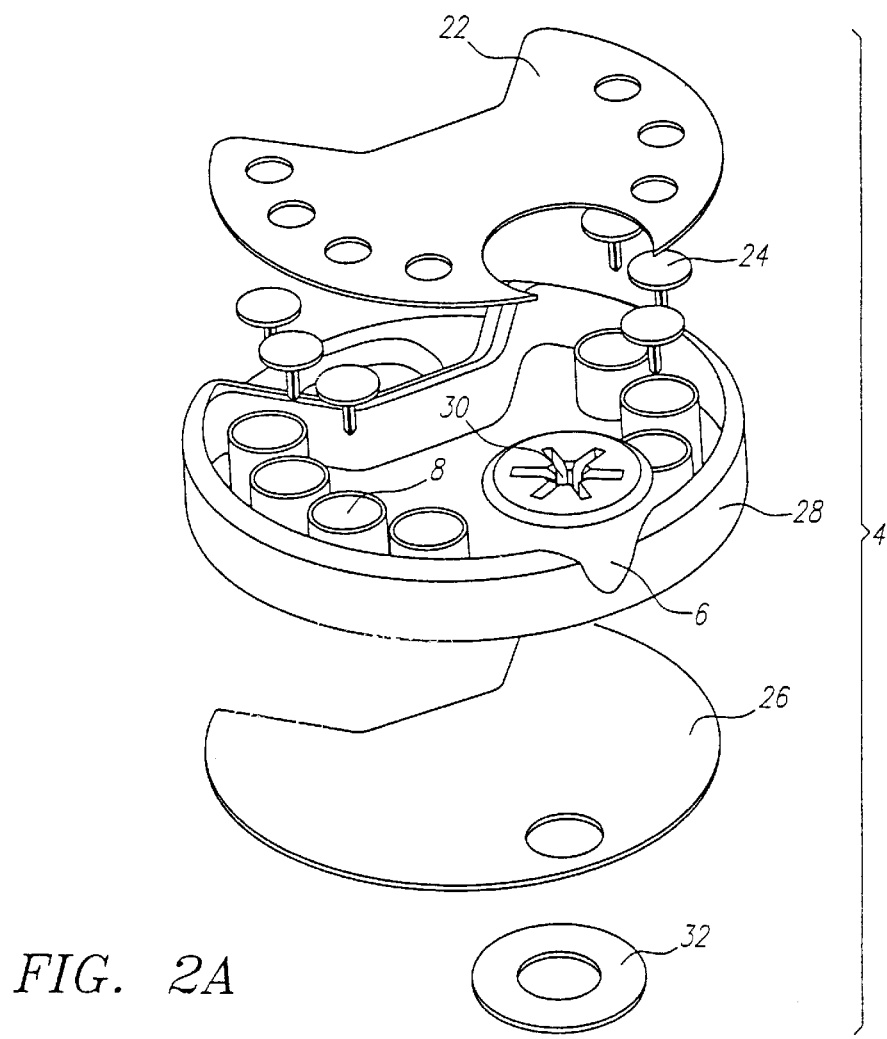
FIG. 2a depicts the various components and their alignment for the reagent carousel portion of the assay cartridge from a top view.

FIG. 2a depicts an exploded view of the reagent carousel 2. An optional cartridge label 22 is designed to carry all of the assay specific information and identification and the lower surface is an adhesive surface that assists in the sealing of reagent wells 8. A hard plastic (e.g., polystyrene) piston 24 is placed in each reagent well 8 during the filling and construction of the reagent carousel 4. The piston 24 is preferably designed to assist in the sealing of the upper opening of the reagent well 8 and in the delivery of reagent to the optically active test surface. In the depicted embodiment, piston 24 has a flat surface that is sealed to label 22 while label 22 also seals to the walls of the reagent wells 8. The skilled artisan will recognize that other methods of sealing the reagent wells may also be employed. For example, an individual seal or moisture barrier may be used to seal the upper opening of each reagent well. In FIG. 2, the sample handling or processing device 6 consists of a series of fingers 30 designed to secure a swab of specific dimensions or fiber bundle size. The sample-processing device 6 is complementary to the type of device (e.g., a swab) on which a sample is to be introduced into the cartridge 2 and/or for the analytical test to be performed by the cartridge 2 in the instrumented assay system. In preferred embodiments, the sample processing device 6 is secured within the reagent carousel 4 by pressure, or physical interference, or a snap fit mechanism, or is molded as part of the reagent carousel. A bottom reagent seal 26 is used to seal the bottom of the reagent well. Preferably, the reagent seal 26 is a mylar type film that is adhered to the molded plastic part 28 prior to the introduction of a liquid reagent to the reagent wells 8 when the reagent well is filled from the top. If the reagent well is filled from the bottom, the label 22 is applied first and label 26 is applied after filling. Preferably, the reagent wells 8 can contain between about 100 to about 600 $\mu$l of reagent, however, the volume of the reagent wells are to be determined by the artisan, based on the intended application. The reagent wells 8 can be configured within the molded part 28 to be of varying internal diameter to accommodate the varying volume of a specific reagent. Those skilled in the art will recognized that other c configurations of the reagent well may be employed. For example, the molded plastic part 28 may be formed such that the reagent well 8 protrudes downward from a flat upper top. The protrusion of the well downward wherein the bottom of the well does not extend below the bottom of the molded plastic part 28. A configuration such as this allows the piston 24 to be pushed down into the reagent well 8 without the need for returning it to an upper position due to exposure and drag in the instrument. The piston size 24 and the volume of air that it displaces in the reagent well 8 can also be used to control the fill volume in the reagent well 8. The filling process will dispense a pre-set volume of each reagent to the appropriate well 8. The reagent seal 26 contains an opening that is positioned under the sample-processing device 6 to allow for flow of the processed sample to the optically active test surface. A vacuum gasket 32 is optionally sealed by adhesive to the reagent seal 26 below the sample-processing aperture. This is to improve the registration of the reagent carousel 4 with the cartridge 2 when the sample processing device 6 is aligned with optical reading well 20 and vacuum is applied from below the optically active test surface. In certain embodiments, processed sample is delivered to the optically active test surface when vacuum is applied to the cartridge 2. In these embodiments, vacuum is used to provide flow when the processed sample would not readily flow into contact with the optically active test surface. Preferably, part numbers 6 and 28 of reagent carousel 4 (see FIG. 2) are made of polypropylene or polyethylene, and part numbers 12 and 14 of the cartridge are made of polystyrene. However, one skilled in the art will recognize that other materials can provide similar structural characteristics.

Figure 2B:
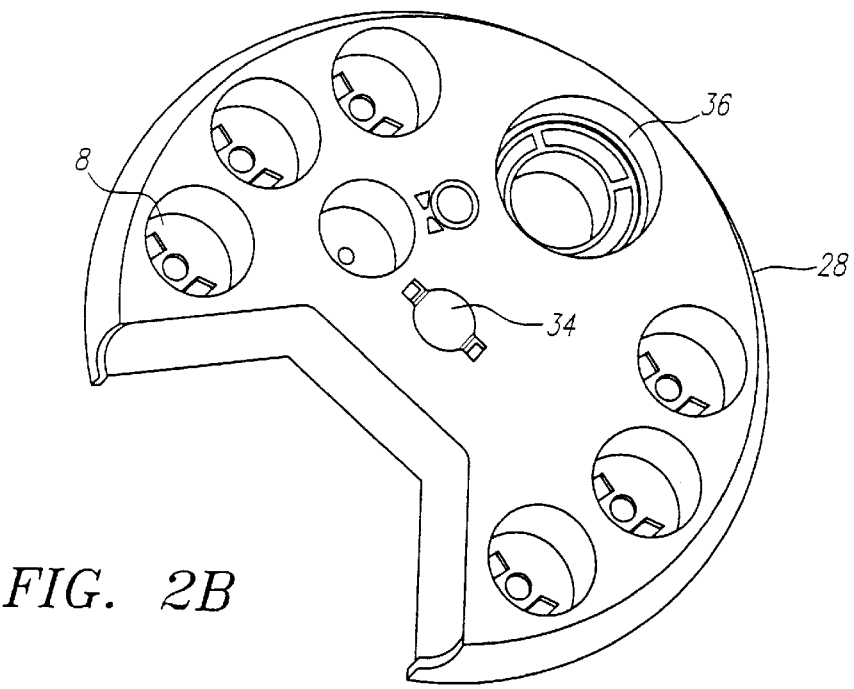
FIG. 2b depicts a top view of the base of the reagent carousel.

FIG. 2b depicts the base 28 of the depicted embodiment of the reagent carousel 4. Also visible are reagent wells 8. The opening 34 allows the cartridge rotation element 96 to seat in the reagent carousel 4 for proper registration and rotation of the reagent carousel during the assay procedure. Opening 36 is designed to accept a variety of sample-processing modules 6. Preferably, the reagent seal 26 is applied to the reagent wells 8 by a heat staking process.

Figure 3:
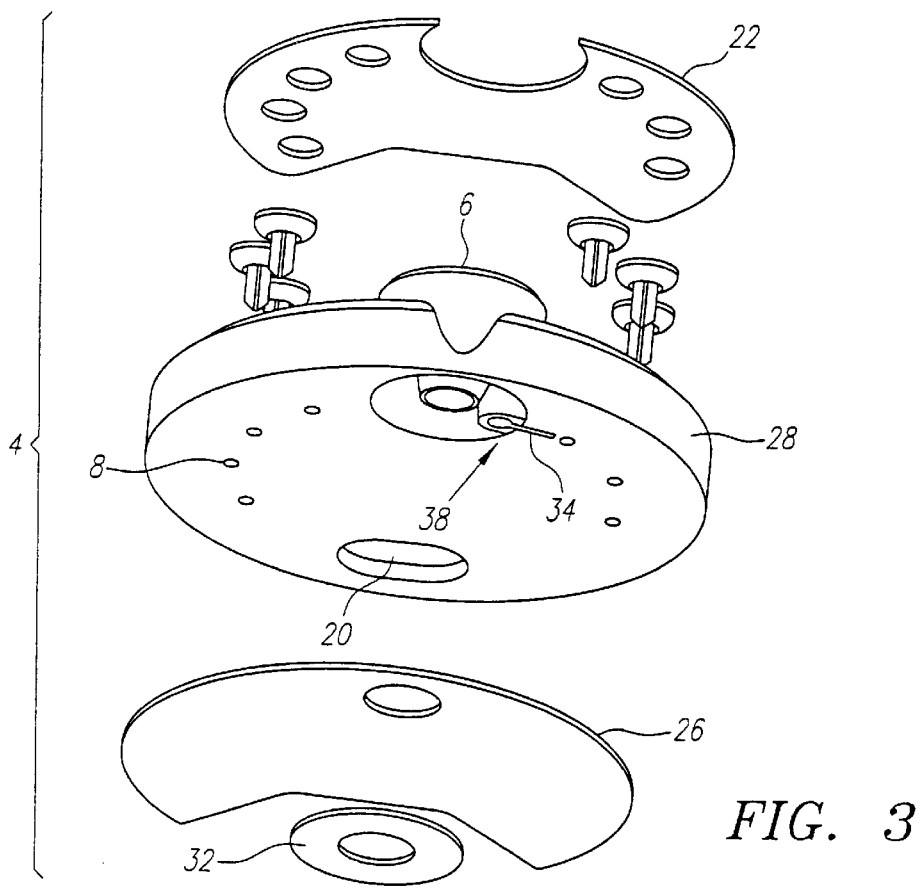
FIG. 3 depicts the various components and their alignment for the carousel portion of the assay cartridge from a bottom view.

FIG. 3 depicts a bottom view of the depicted embodiment of the reagent carousel 4. The features visible from this view include an extraction reagent flow channel 38 and a differential seal 34 designed to control the flow of extraction reagent(s) into the sample-processing device 6. In certain embodiments, a flat piston (not pictured) applies pressure to break the weak reagent seal 34 and allow flow to occur within reagent channel 38. As the piston is displaced downward the extraction reagent is driven through the channel 38 and up the continuation of channel 38 to a well contained within the sample-processing feature 6. In these embodiments, the positive displacement of the piston generates sufficient pressure to move the extraction reagent up and into the sample-processing feature. Thus the extraction reagent or diluent flows into the sample-processing device and contacts the sample collection device or added sample. In embodiments which utilize vacuum to facilitate sample flow, application of vacuum releases the analyte of interest from the sample collection device to the test surface.

Figure 4:
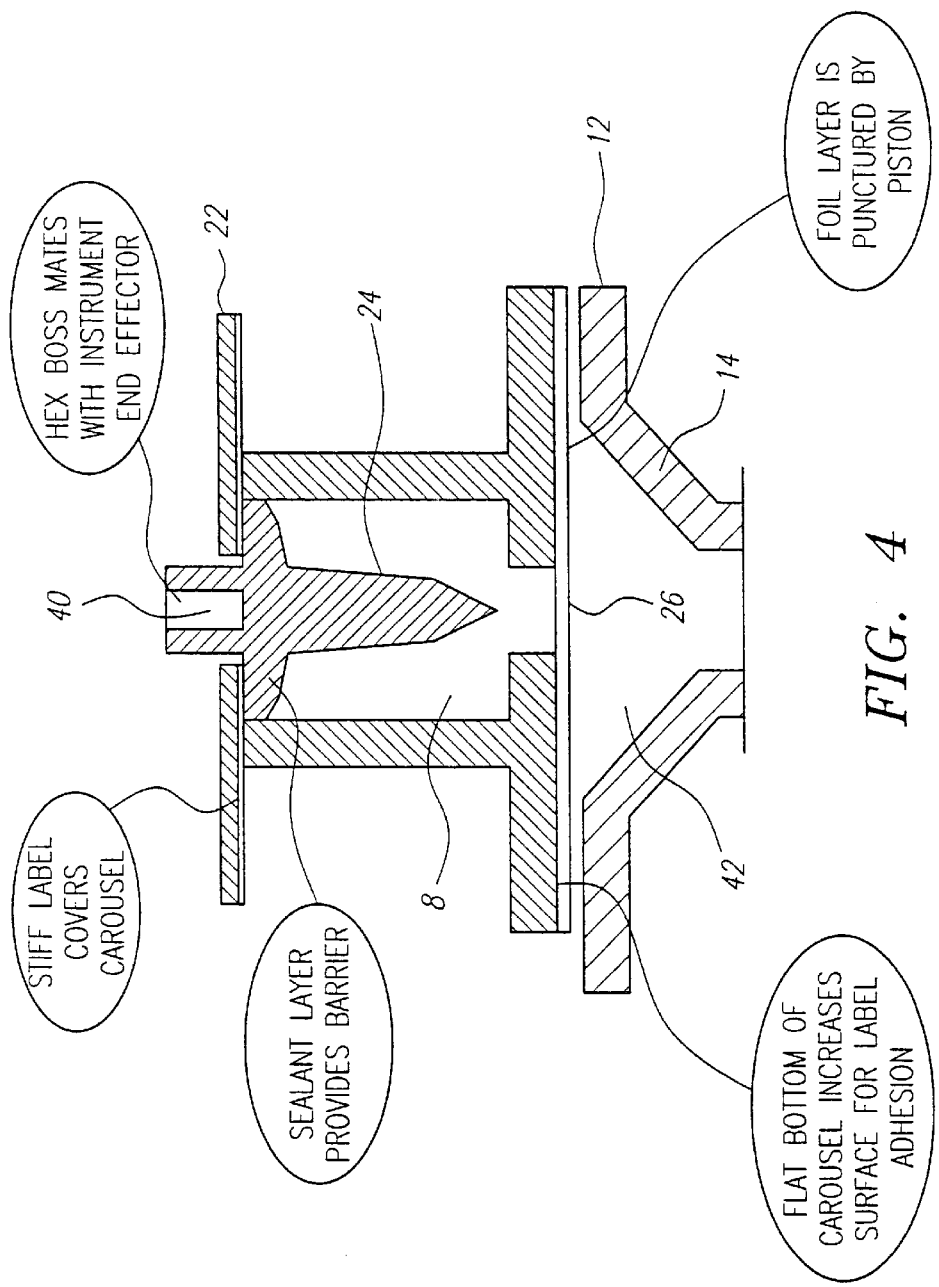
FIG. 4 depicts an enlargement of a sealed reagent well within the reagent carousel and one possible piston design contained within the reagent well and the contact between the reagent well and reagent delivery port in the bottom section of the assay cartridge.

FIG. 4 depicts an cross sectional view of a reagent well 8 in preferred embodiment of the final assembled reagent carousel 4. Label 22 is designed so that the upper portion of piston 24 is also sealed with label 22. Thus, the label 22 contacts the piston 24 and the top of the reagent wells 8 to provide a multi-component seal. The piston 24 includes an optional hex boss feature 40 designed to mate with the instrument plunger mechanism and has a pointed end structure. FIG. 4 shows the reagent well 8 positioned over the optical reading well 20 and shows a cross sectional view of the optical read well 20 side walls 42. The side walls 42 are preferably designed to provide an uninterrupted optical pathway and to accommodate the reagent volumes to be applied to the optically active test surface. An optional gasket may be placed between the reagent carousel 4 and the upper portion 14 of the bottom section of the cartridge 2.

Figure 5:
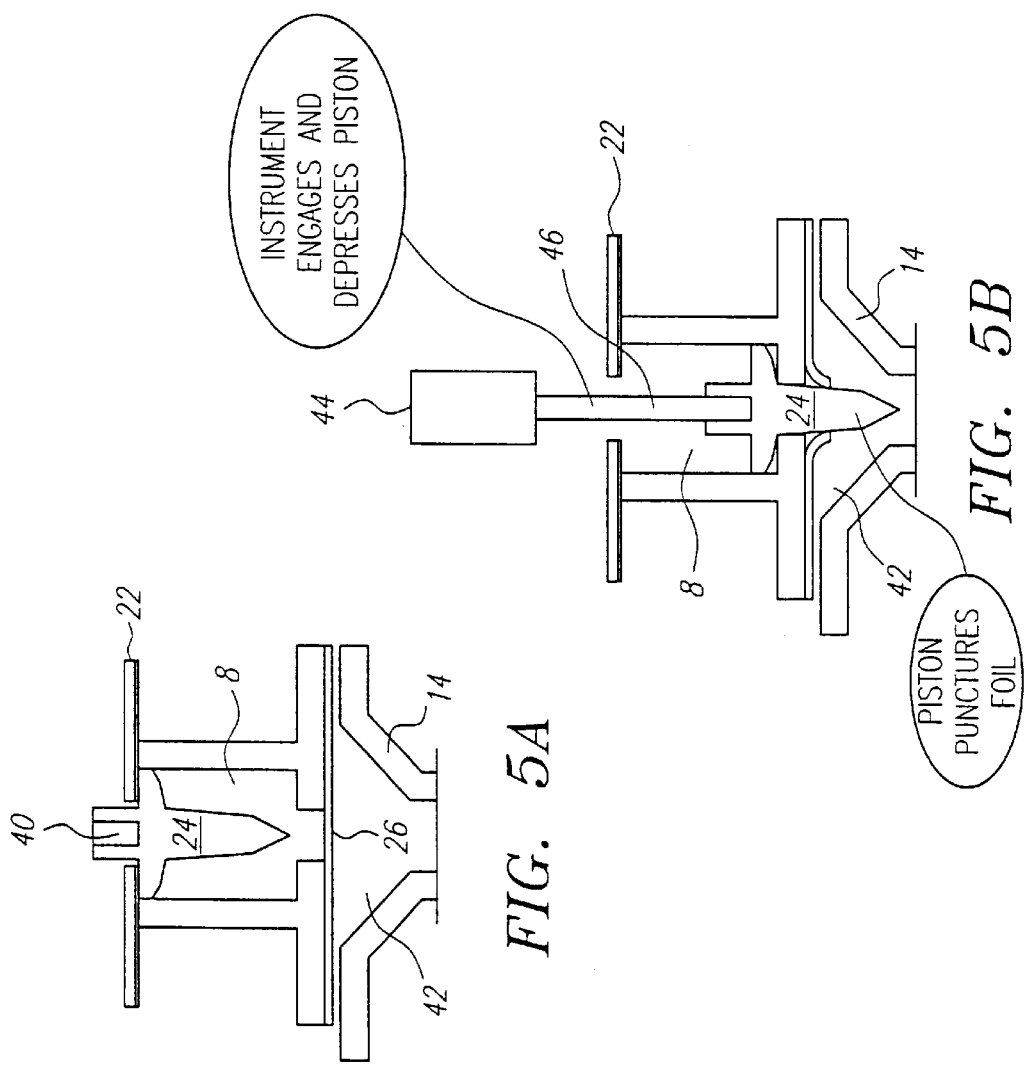
FIGS. 5(a–c) depicts the reagent well within the reagent carousel and the piston action for reagent delivery.

FIGS. 5, a–c, depicts a preferred displacement process for the piston 24 to deliver reagent to the surface of an optically active test surface. In this embodiment, a push rod 46 is attached to a vertical drive element 44 (FIG. 5*b*). The end of push rod 46 is designed to seat within the optional hex boss 40 of the piston 24. When the piston does not include a hex boss feature the push rod may simply contact the piston to drive it. As in FIG. 5*b* the vertical drive element 44 then drives the push rod 46 and the piston 24 downward and piston 24 will pierce the seal 26 and release the reagent from the reagent well 8. Push rod 46 may also pierce label 22 prior to contact with the piston 24. The downward force exerted by the vertical drive element 44 and the push rod 46 is sufficient to break the seal of the upper flat structure of piston 24 from the seal 22. For the preferred seal material described herein, approximately 5–7 pounds of force is required. The skilled artisan can easily determine the necessary force for breaking other sealing materials. Once the seal 26 is pierced the reagent preferably flows down the side walls 42 of the optical reading well 20 and into contact with the optically active test surface. The vertical drive element 44 and the push rod 46 then optionally pull the piston 24 back to its original position within the reagent well 8 to prevent the piston 24 from restricting rotation of the cartridge 2 (FIG. 5*c*). The retraction mechanism may not be required if the hex boss is not included in the piston or it is not required to return the piston to an original position.

Figure 53:
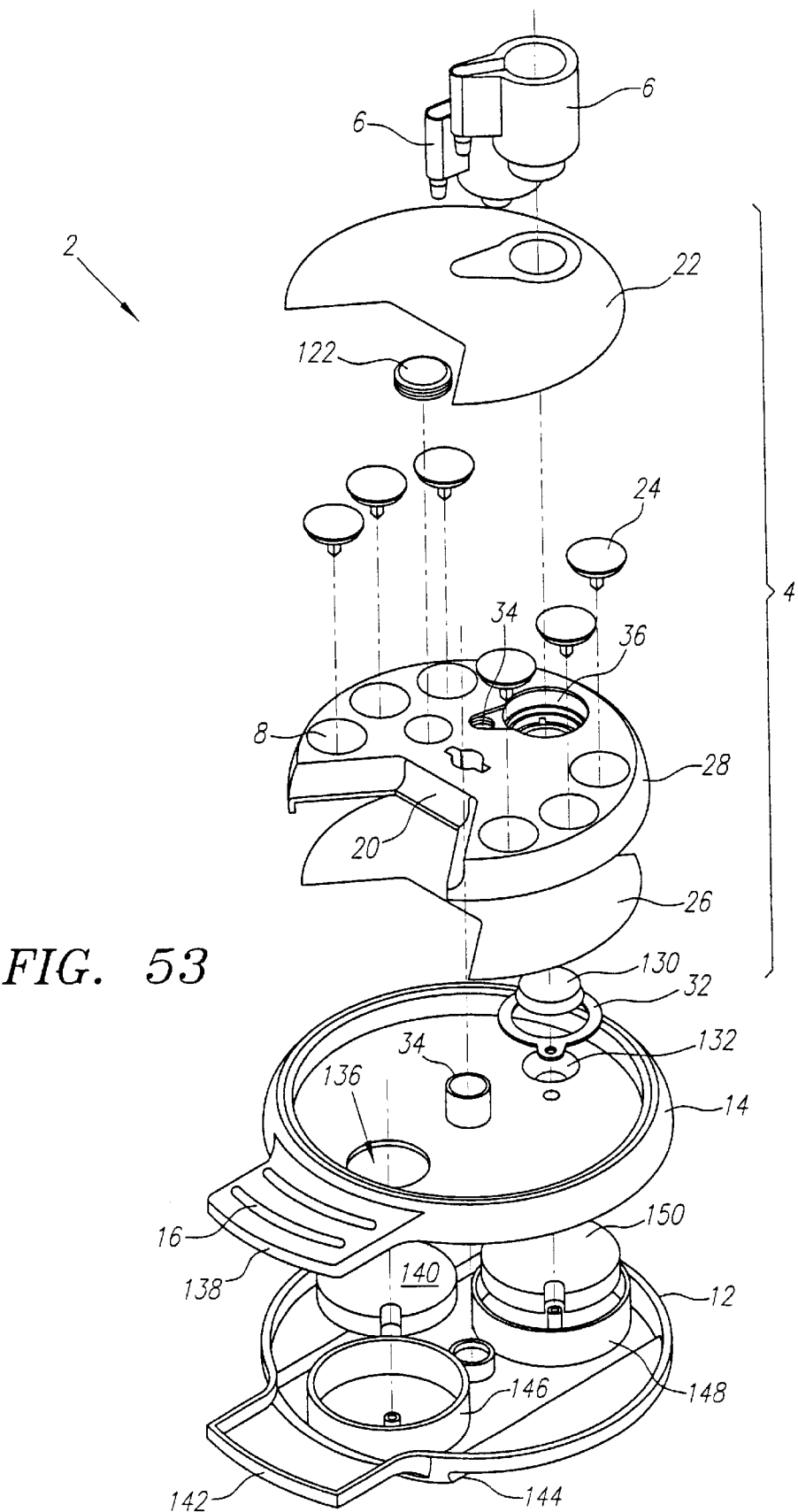
FIG. 53 depicts an expanded view of an assembled reagent cartridge.

FIG. 53 depicts an exploded view of the depicted embodiment of the assembled cartridge, consisting of the cartridge bottom of FIGS. 54*a–d* with the reagent carousel 4 of FIG. 1. When the sample type to be analyzed is a fluid from which an analyte containing particulate is to be removed, the bottom of sample-processing feature 36 preferably consists of an optional membrane material designed to retain the particulate and remove the excess sample fluid. If required, vacuum is applied to 36 after the fluid sample is applied and port 36 is aligned with 136 so that fluid flows into adsorbent 140. An extraction reagent can be applied to the membrane in 36, such that the analyte is removed from the particulate matrix. In the depicted embodiment, when 36 is aligned over the optically active test surface 132 and vacuum is applied, the extracted analyte flows through the membrane at the bottom of 36 and through the filter unit 130 and onto the optically active surface 132. If the sample processing feature 36 is designed for use with a non-fluid sample, or the analyte is not particulate associated, the membrane sealed to the bottom of 36 may not be required. Piston 122 is the piston used to deliver extraction reagent as described herein.

FIG. 54*a* depicts a preferred configuration of the assay cartridge bottom 152, where part 152 replaces part 12 and part 14 of the assay cartridge shown in FIG. 1. Extension 34 mates with the corresponding opening 34 in the reagent carousel 28 and matches the part 120 of the instrument to drive the rotation of the reagent carousel. This cartridge configuration includes an optional grip position 138 that may support surface extensions to improve the manual grip of the assay cartridge. Opening 136 allows a fluid sample such as urine to be directed to the adsorbent waste pad 140 seen in FIG. 53. Opening 132 provides access to the optically active test surface. The optically active test surface is attached to the bottom of part 152 at position 132. Opening 154 is a vacuum port. FIG. 54*b* depicts the bottom view of the preferred configuration of the assay cartridge bottom 152.

Figures 54C, 54D:
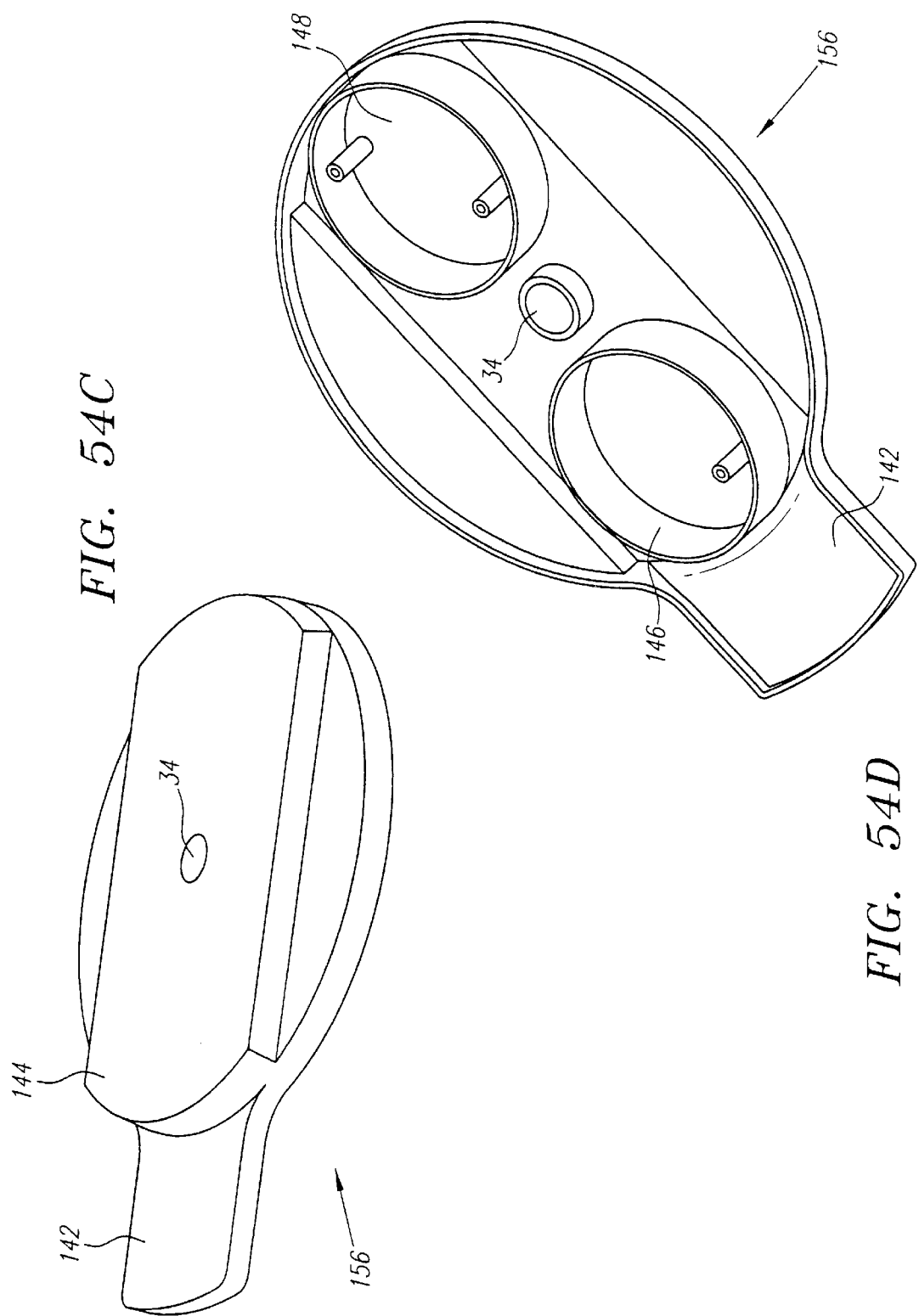

FIG. 54*c* depicts the bottom view of a preferred configuration of a cartridge bottom-housing portion 156 of the assay cartridge 2. The bottom-housing portion 156 has an optional grip portion 142 that aligns with optional grip 138 in the assembled assay cartridge. Opening 34 aligns with the opening 34 of the cartridge bottom 152 as part of the assay cartridge rotation mechanism. Raised section 144 of the vacuum housing portion 156 is used to provide a mechanical seating of the cartridge within the instrument. FIG. 54*d* shows the upper view of a preferred configuration of vacuum housing portion 156. Wells 146 and 148 preferably retain the adsorbent materials 150 and 140 shown in FIG. 53.

The Analytical Instrument

Figure 6:
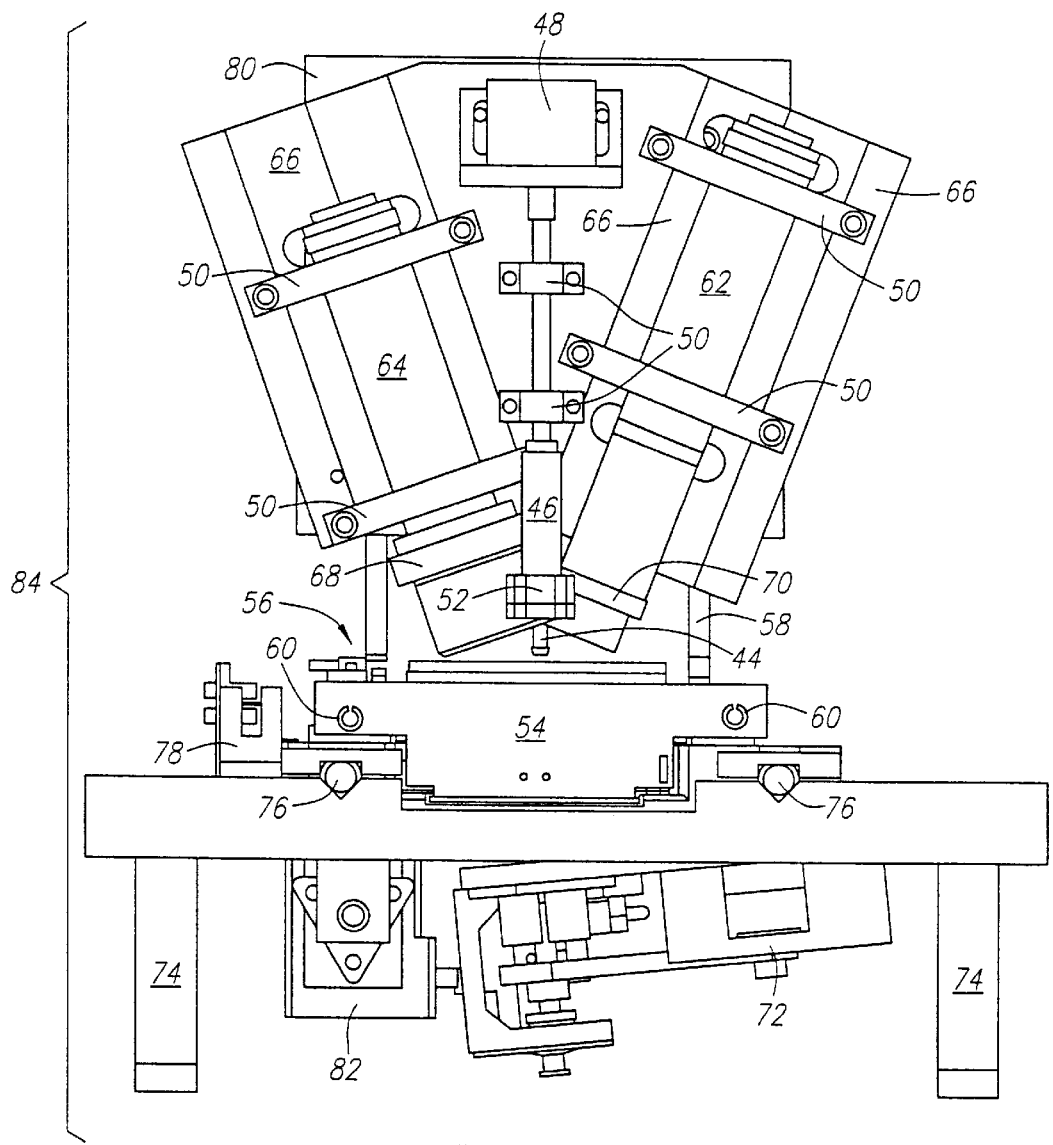
FIG. 6 depicts a front view of an open instrument system.

FIG. 6 depicts a front view of a preferred embodiment of instrument system 84. In this embodiment, the instrument is supported on a platform supported by legs 74. Preferably, the instrument comprises an optical detection portion that consists of parts 66, 64, 68, 62, 70, and optional retention brackets 50. The brackets 50 can be used to stabilize the placement of key instrument components. Part 66 is an optional solid plate designed to attach to instrument back support 80 and casing support 58 and to align the components of the optical detection portion of the instrument. In this preferred embodiment, the optical detection portion consists of a light source 62 and a fixed polarizing element 70. In addition the optical detection portion consists of a detector 64 and a fixed analyzing polarizing element 68. The v-block structure of 66 provides the angle control or a fixed angle position for the optical detection portion of the instrument. An optical encoder 78 is used to assist in the optical scanning of the surface. The skilled artisan will recognize that the instrument design can be modified to use alternative detector types, as described herein. For example, the described optical detection portion may be replaced by a fluorimeter, spectrophotometer, etc.

A plunger, or vertical drive, element 44 is preferably attached to linear motor 48. A push rod 46 can be attached to the vertical drive element 44. Another element of this embodiment of a total vertical or linear drive assembly is an optional presser foot 52. The presser foot 52 provides downward pressure on the cartridge 2 to align and stabilize the cartridge 2. The presser foot may not be required if a lock and key mechanical registration method is used to secure the cartridge within the instrument.

In the depicted embodiment, the cartridge positioning assembly includes an optional loading door 54 that is attached to rails that are anchored to loading door 54 by retention rings 60. Cartridge rails 76 can be used to horizontally align and place the assay cartridge 2 within the proper position for the optical detection portion and the vertical drive assembly for reagent release and optical analysis. In this embodiment a latch 56 is used to secure optional loading door 54, but the skilled artisan will recognize that other mechanisms can be utilized. All or some of the depicted features may be preferably eliminated, for example if a locking-type or pin set mechanism is used for cartridge retention and stability, and the optimal design is left to the artisan, based upon the requirements of the selected cartridge format, detector type, etc. With such a pin set mechanism, relying on two set pins and the rotation element 96 for cartridge retention, part numbers 52, 76, 54, 60, 88, 90, 92, 94, and 54 are eliminated. The cartridge rails 76 can be replaced by a single extruded sliding support on each side of the instrument. The cartridge receiving stage is attached to brackets that are capable of sliding and the brackets are slidably attached to the side supports.

Optional sensor 104 detects when the optional vacuum engagement mechanism 72 is aligned to apply vacuum to the assay cartridge 2. In certain embodiments, the vacuum engagement mechanism 72 displaces the vacuum from engagement with the bottom of the instrument to allow cartridge rotation and cartridge loading and unloading. The sensor 104 and the vacuum engagement mechanism 72 may be replaced when the cartridge receiving mechanism is sufficient to align and stabilize the cartridge in the absence of vacuum. In preferred embodiments, the stage is attached by brackets to the extruded side supports, and the cartridge is pressed down as it is brought into the interior of the instrument from the cartridge loading door. As the cartridge is lowered on to the receiving stage it contacts an optional vacuum mat that serves to provide a vacuum seal when vacuum is applied to the cartridge.

Figure 7:
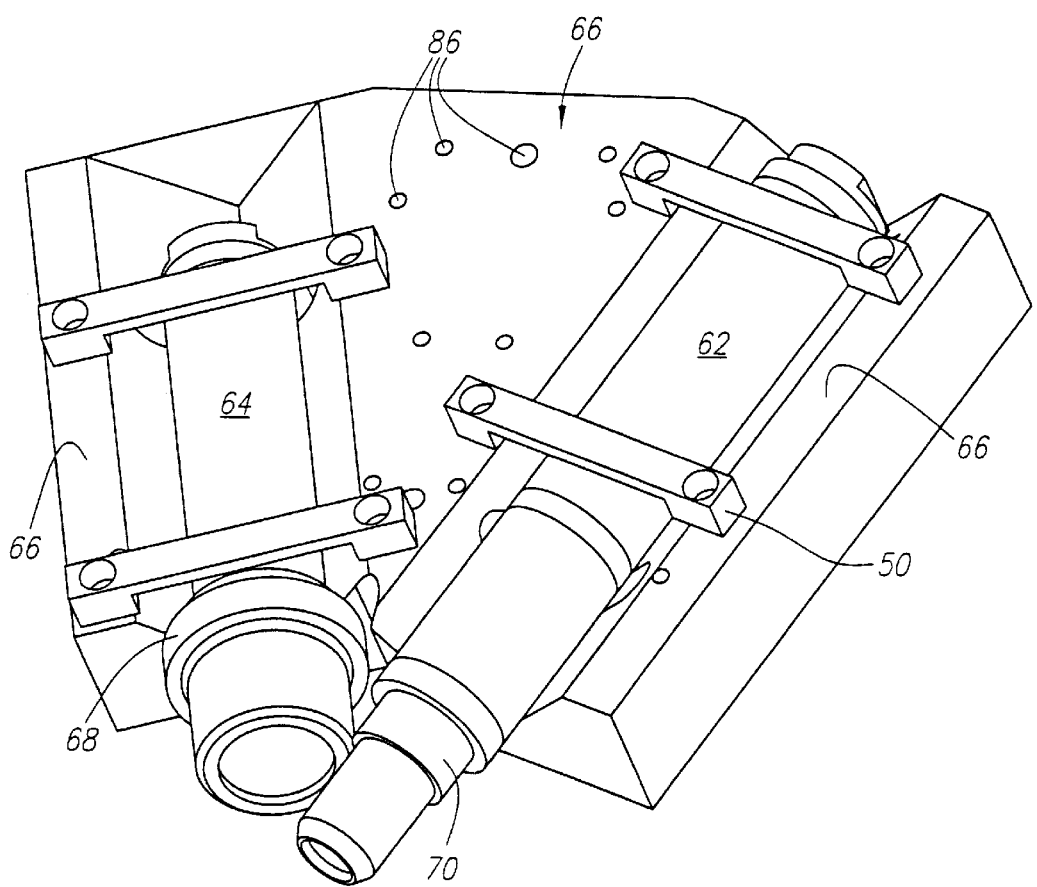
FIG. 7 depicts the optical components and the anchor plate for those components.

FIG. 7 depicts an enlarged view of a preferred optical detection portion of the instrument 84. The v-block structure 66 is clearly visible and provides for proper optical alignment. The v-block structure is preferably made of machined or cast metal construction to provide the stability that the optical alignment requires. Other similar materials known to the artisan can provide similar stability. Various mounting holes 86 are shown within the v-block structure 66.

Figure 8:
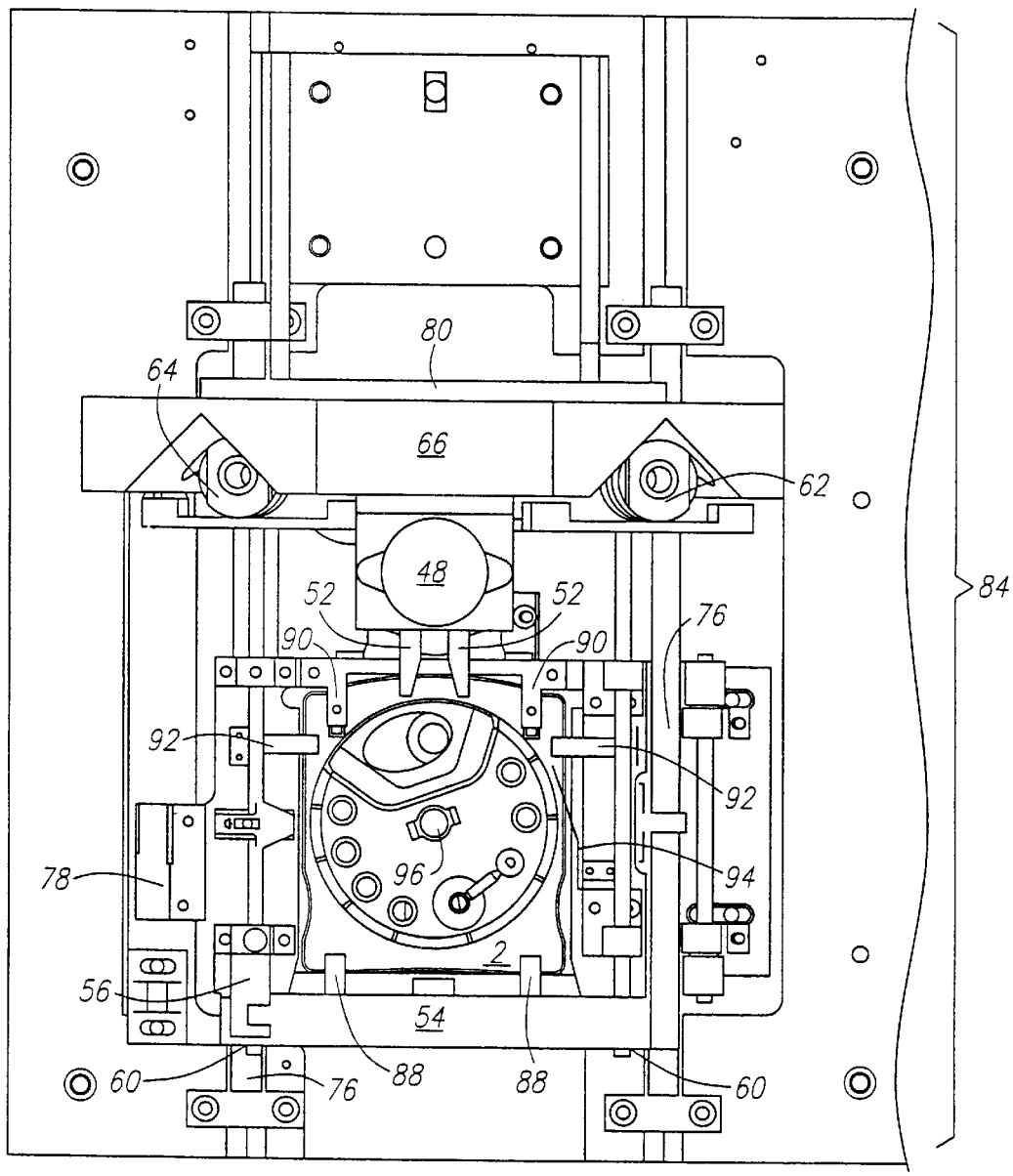
FIG. 8 depicts a downward looking view of an open instrument system demonstrating cartridge placement and other key instrument features.

FIG. 8 shows a top view of the depicted embodiment of instrument 84. Optional features demonstrated in this view are the alignment springs 94 that provide alignment and stability for the cartridge 2 once secured in the cartridge delivery assembly. The optional presser foot 52 that assists in cartridge positioning is also more clearly visible. In preferred embodiments springs 92 also assist in the alignment and stability of the cartridge 2.

In certain preferred embodiments, the cartridge 2 is freed to rotate by contact of optional pressure feet 90 with the optional tabs 10 on the cartridge 2. Additionally, alignment and stability can be provided by locking feet 88. The cartridge delivery assembly rails 76 are also shown. In the depicted embodiment, the cartridge 2 is displaced from the front of the instrument where it is loaded to the proper position for analysis. Optional cartridge loading door 54 also provides stability and alignment of cartridge 2. Rotation drive element 96 preferably seats in the center of cartridge 2 and assists in the rotation of the reagent carousel 4 to the appropriate position as the assay procedure is conducted. As noted above some or all of these elements may be replaced or eliminated depending on the mechanism used to retain and position the cartridge.

Figure 9:
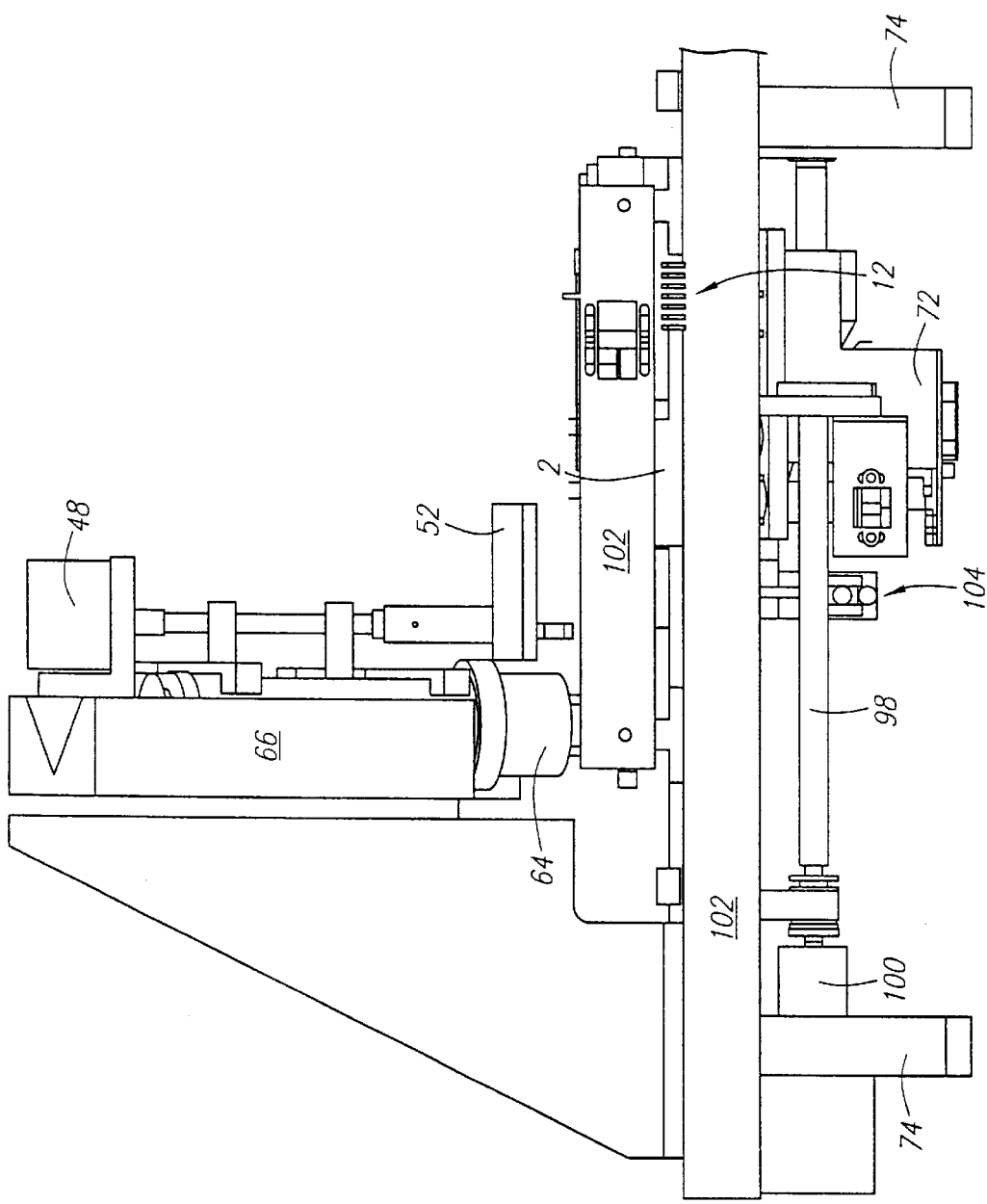
FIG. 9 depicts a side view of an open instrument system.

FIG. 9 depicts a side view of the depicted embodiment of instrument 84. Features visible in this view include an optional cartridge positioning assembly side wall 102. In preferred embodiments, the side walls help retain and align the cartridge 2 as it is moved into proper alignment for the assay procedure to be conducted and the optical analysis completed. In this view the optional vacuum engagement element 72 is in the engaged position such that vacuum is applied in the proper sequence and positions. Optional optical sensor 104 is involved in control of the cartridge 2 rotation. In the depicted embodiment a translation screw 98 is attached to motor rail 100, providing for the movement of the cartridge 2 into and out of the instrument detection path and processing elements. In certain preferred embodiments, the two separate pieces numbered 102 may become one single extruded side support when the cartridge platform is attached to brackets that are capable of sliding and the brackets are slidably attached to the side support. The slide can allow for proper positioning of the cartridge within the instrument.

Figure 10:
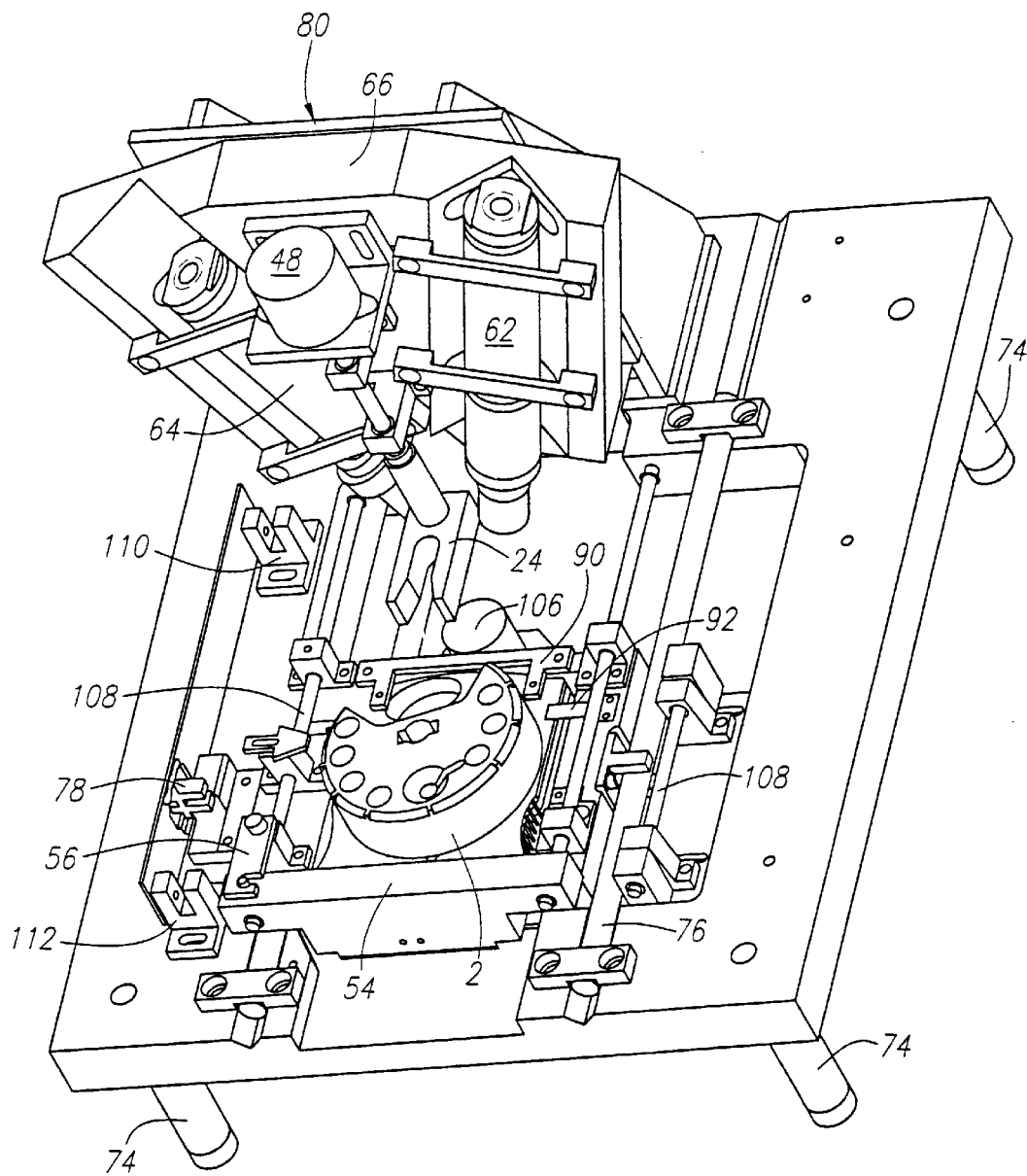
FIG. 10 depicts an elevated off angle view of an open instrument system.

FIG. 10 depicts an oblique view of the depicted embodiment of instrument 84. In this view the optional presser foot 52 is raised from the contact with cartridge 2 so that motor 106 is visible. In this preferred embodiment, motor 106 moves the optional vacuum engagement mechanism 72 into and out of contact with the bottom of instrument 84. Thus motor 106 assists in the activation and removal of vacuum during the assay procedure. An optional latching mechanism 56 is also more visible. As noted previously, any other mechanism that can be used to secure the loading door 54 once a cartridge 2 is loaded into the cartridge delivery track can be used or may not be necessary if a different mechanical registration mechanism is used for the cartridge. Optional optical sensor 110 is used to sense when the cartridge is properly positioned under the optical detection portion and relative to the piston drive elements. In preferred embodiments, rails 108 serve to seal the cartridge loading door 54 against the cartridge 2 and provide secure cartridge alignment. These optional rails 108 may be driven by motor 106 or may have an independent motor controlling their translocation. Optical sensor 112 senses when the cartridge loading door 54 is in the home or initial position. Motor 106 may be eliminated if the vacuum system engagement features is addressed by the cartridge positioning and a vacuum mat system.

Figure 11:
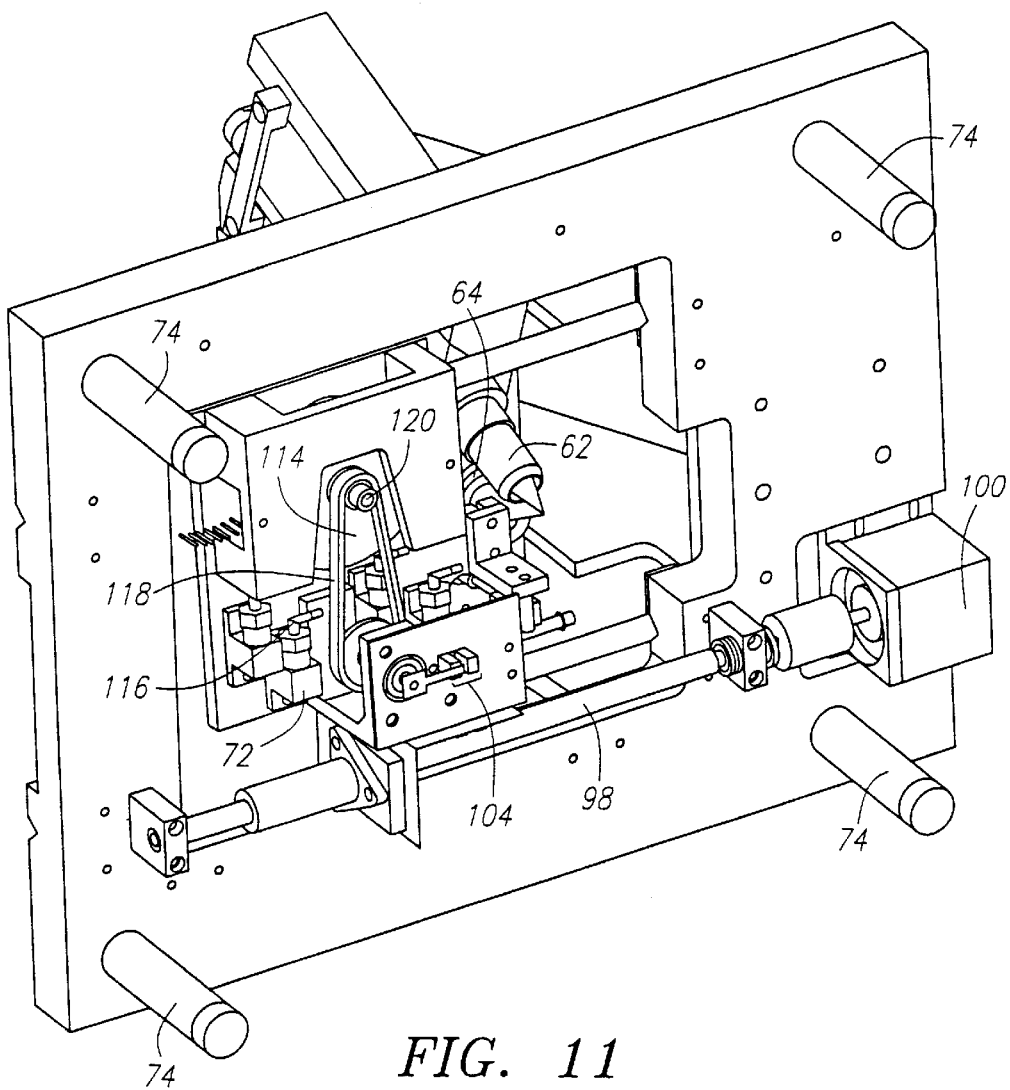
FIG. 11 depicts a bottom view of an open instrument system.

FIG. 11 depicts the depicted embodiment of instrument 84 in a bottom view. Features visible in this view include a carousel rotation motor 114 and vacuum connectors 116. The optional vacuum connectors feed into pliable plastic gaskets or suction cups that assist in creating the vacuum seal to the appropriate cartridge features. In this preferred embodiment, drive belt 118 works with rotation motor 114 to rotate the cartridge. Also visible is the bottom section of rotation drive element 120 that is in contact with drive belt 118. Other mechanisms to rotate and/or index the cartridge can be used in place of the motor and drive belt of the depicted embodiment. The choice of a suitable rotation mechanism is preferably left to the skilled artisan, and can be appropriate to the cartridge design.

Instrument Control Algorithms

FIGS. 12–54 depict various system flow charts for preferred power-on processes to a final data analysis. The design of the instrument provides sufficient flexibility for the skilled artisan to design appropriate control algorithms for a particular assay. One skilled in the art will recognize that not all of the depicted flow charts, or the various portions thereof, will be required for a given assay or instrument design. The skilled artesian will also recognize that the depicted flow charts, or various portions thereof, may be combined into one function, or split into multiple functions, dependent upon the needs of a given protocol, assay, or instrument.

Figure 12:
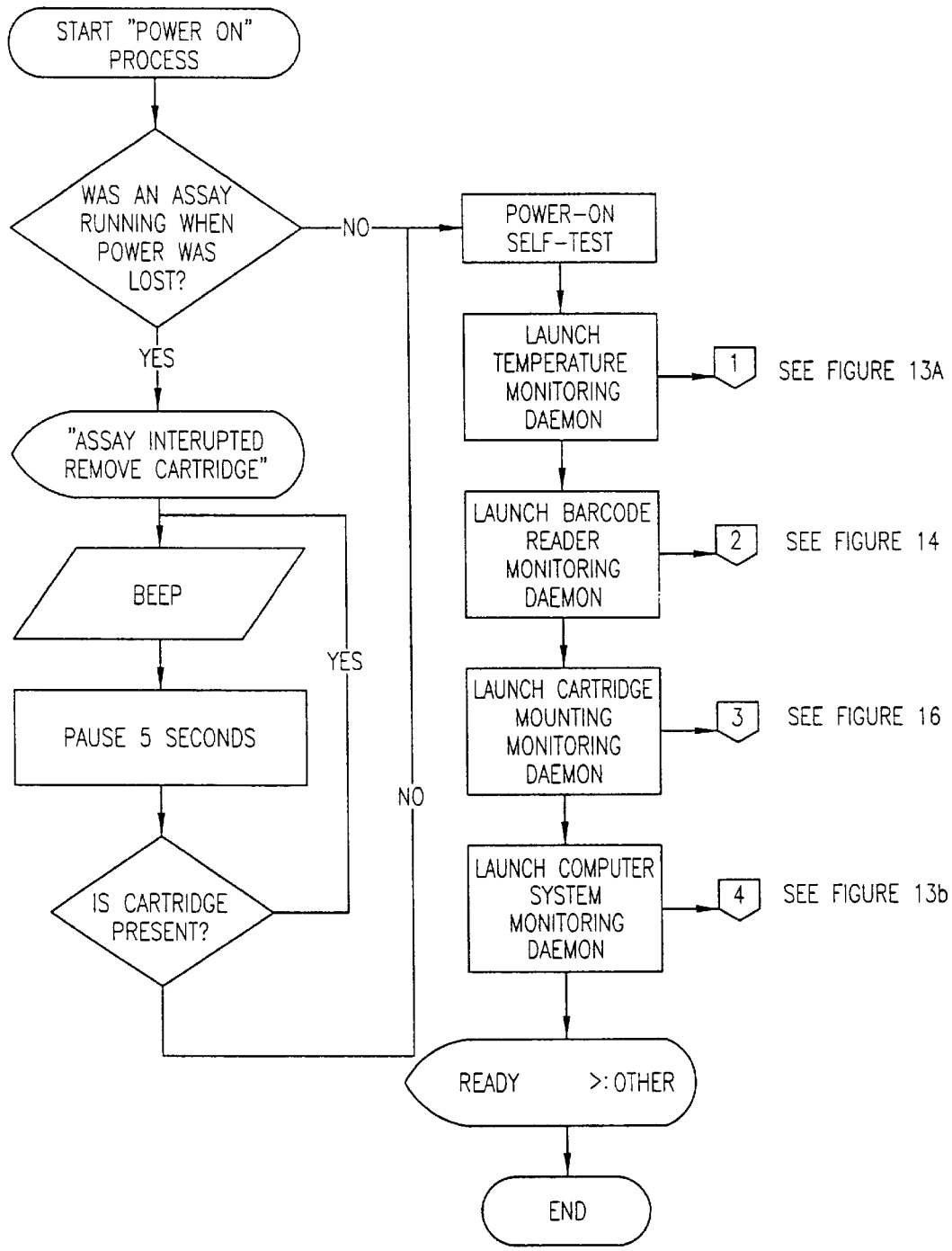
FIG. 12 depicts a system flow chart for the power on process of the instrumented system.
Figure 13A:
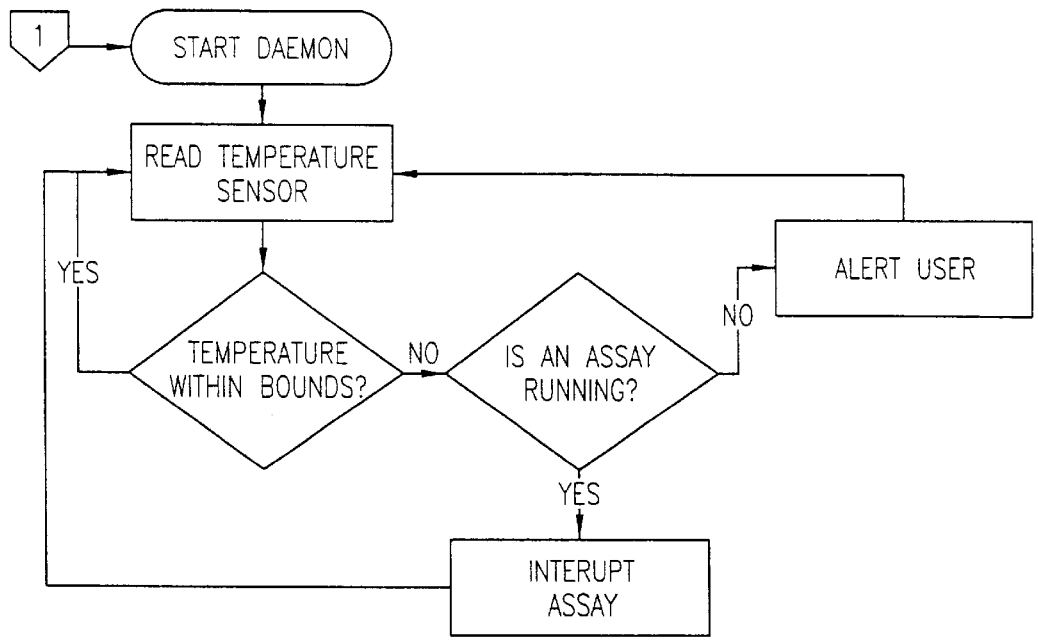
FIG. 13 depicts a system flow chart for the temperature monitoring and computer system monitoring Daemon.
Figure 13B:
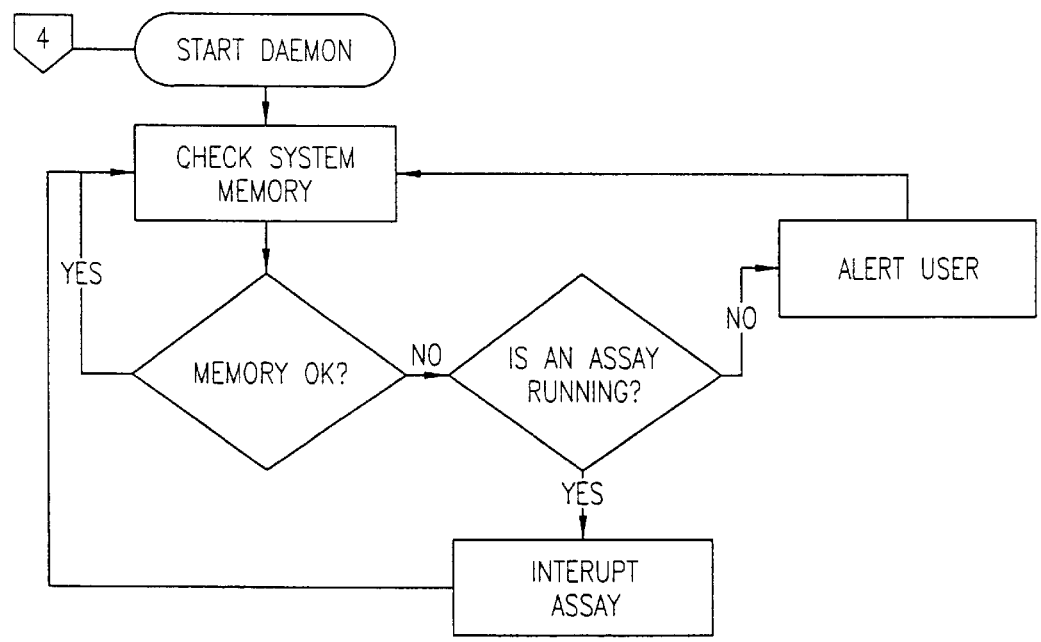
Figure 14:
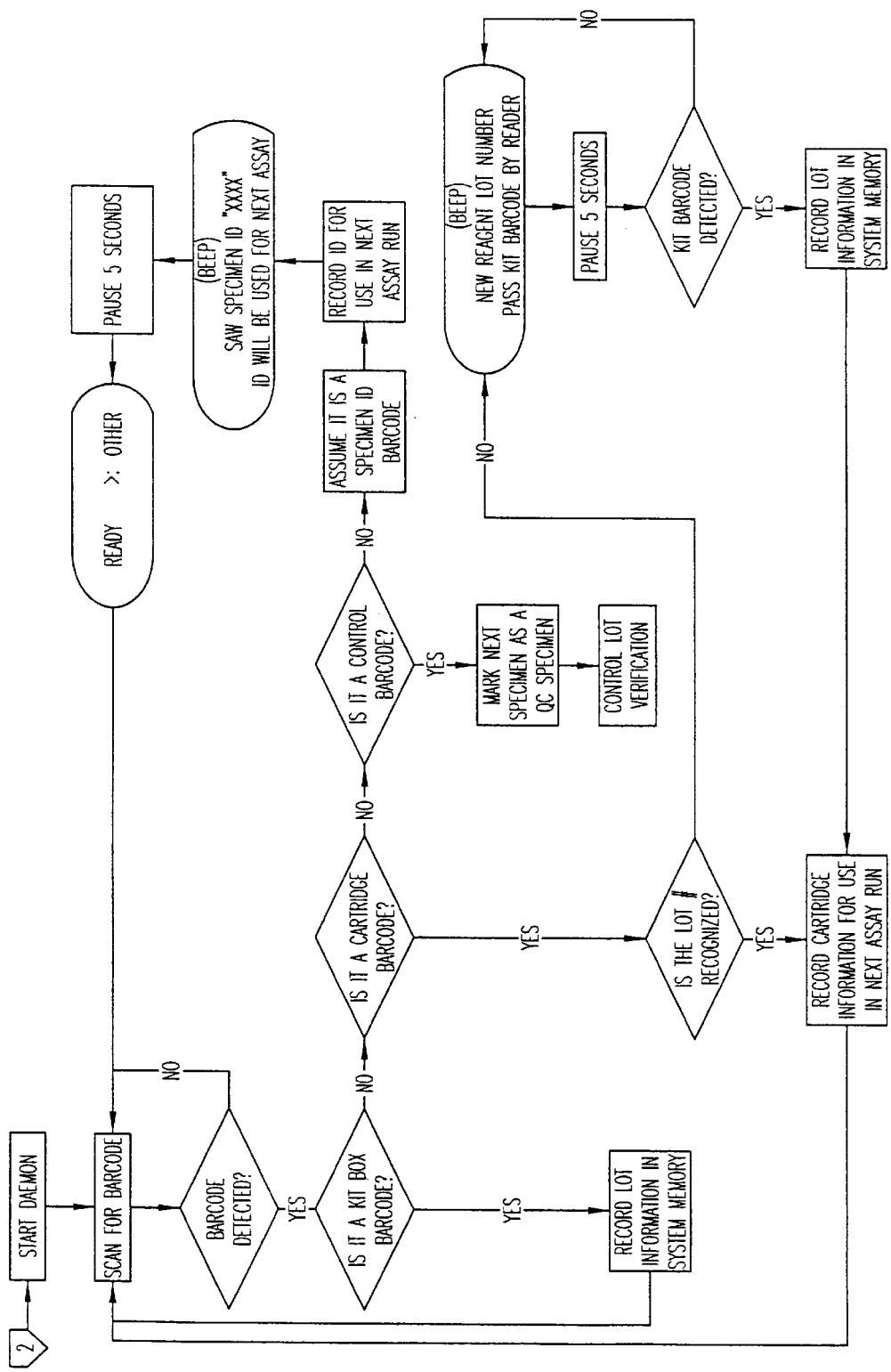
FIG. 14 depicts a system flow chart for the bar code monitoring Daemon.
Figure 16:
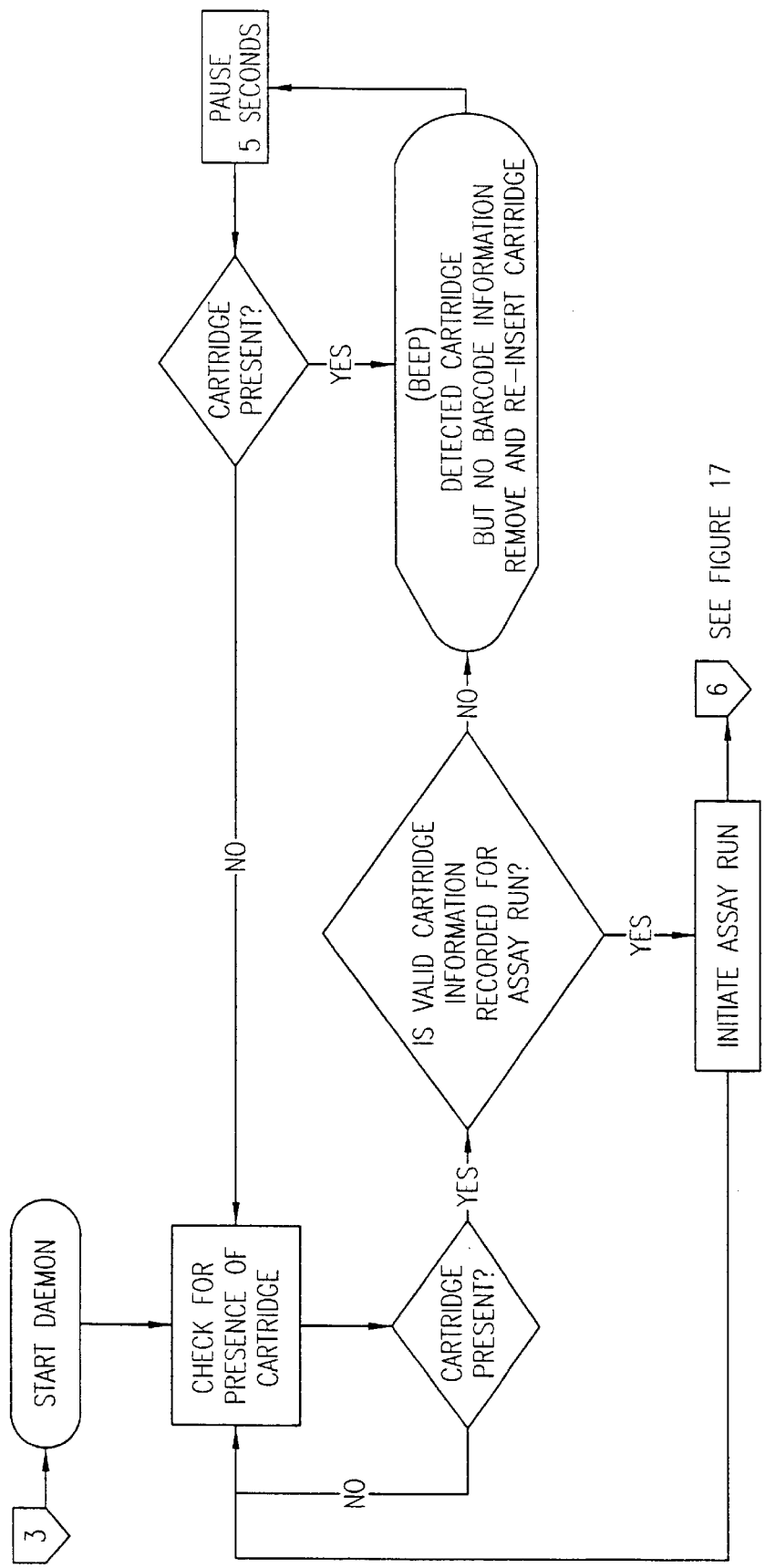
FIG. 16 depicts a system flow chart for the cartridge mounting monitoring Daemon.
Figure 17A:
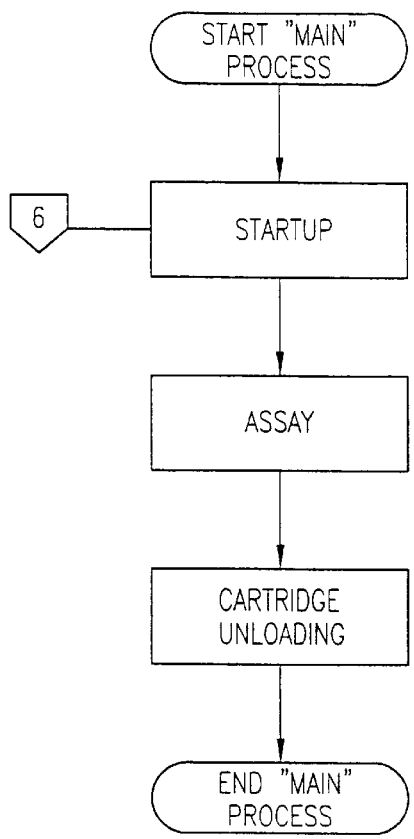
FIG. 17 depicts a system flow chart for the main process.
Figure 17B:
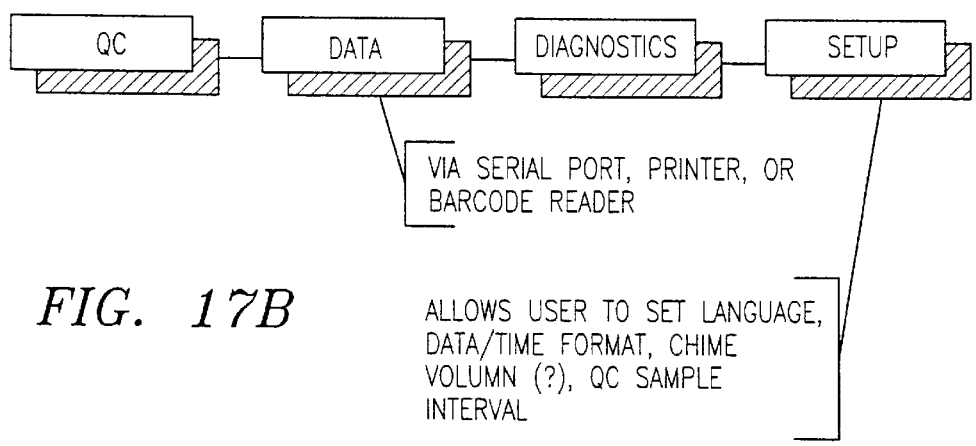

FIG. 12 depicts a preferred control algorithm used for the system power-on process. The depicted control algorithm indicates the various control points during a preferred start-up procedure where an out of specification reading can lead to failure to complete the start-up procedure and where action by the user may be required. For example, control points 1–4 are found in FIGS. 13a, 14, 16, 13b, respectively. Control point 1 determines that the system's ambient temperature is in the proper range for optimal assay performance before an analysis can be performed (FIG. 13a). In certain embodiments this control point may include feedback control over a heating an/or cooling unit designed to maintain the system's temperature at the requirements of a given assay. Those skilled in the art will recognize assay temperature requirements comprising an assay or protocol for a given system. Control point 2 determines that the barcode reader function (when included) can properly identify the barcode information on the kit box, the assay cartridge, and/or the specimen. If there is a failure in the barcode, cycle user intervention may be required (FIG. 14). Control point 3 determines that the cartridge is present and that the cartridge information is adequate to begin the assay procedure (FIG. 16). Control point 3 has its own control point 6 (FIG. 17). This control point determines that all requirements are met and the assay procedure can be started. Control point 4 (FIG. 13b) establishes that the system memory is performing to specifications. If a bar code reader is not included in the instrumented system then an alternate verification scheme would be designed into the system software to confirm the availability of the proper control information.

Figure 15:
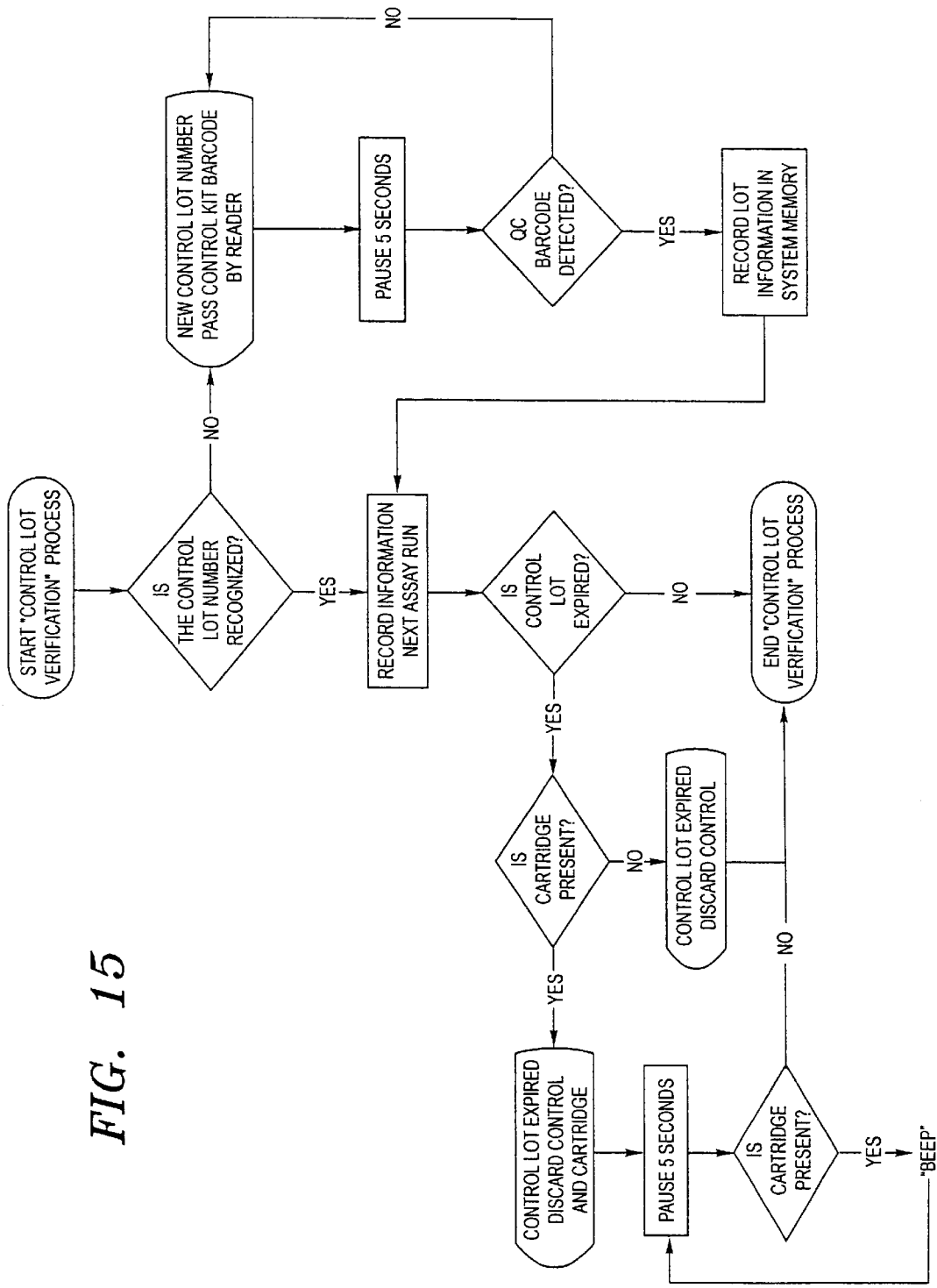
FIG. 15 depicts a system flow chart for control lot verification.
Figure 18:
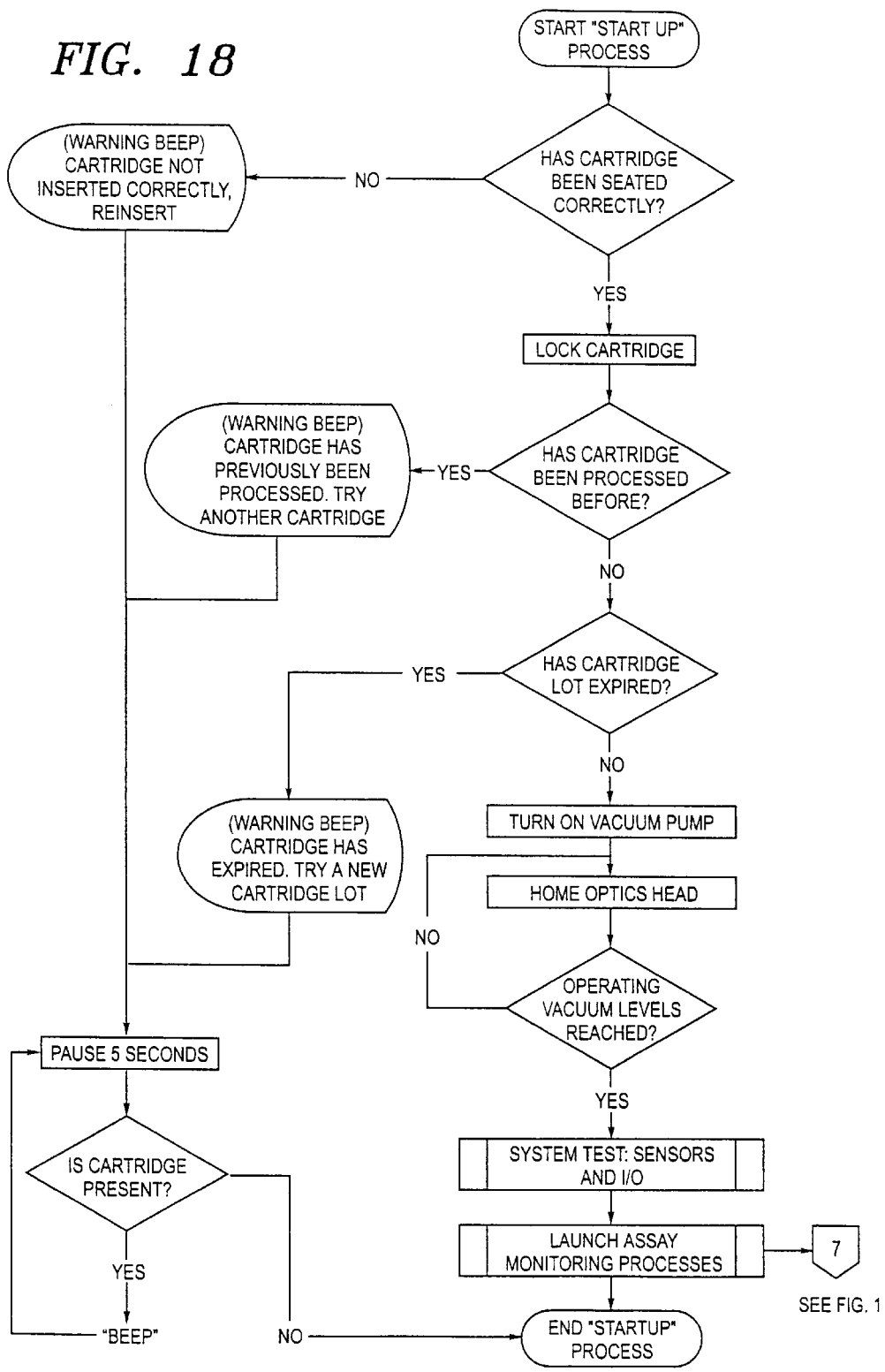
FIG. 18 depicts a system flow chart for start-up.
Figure 19:
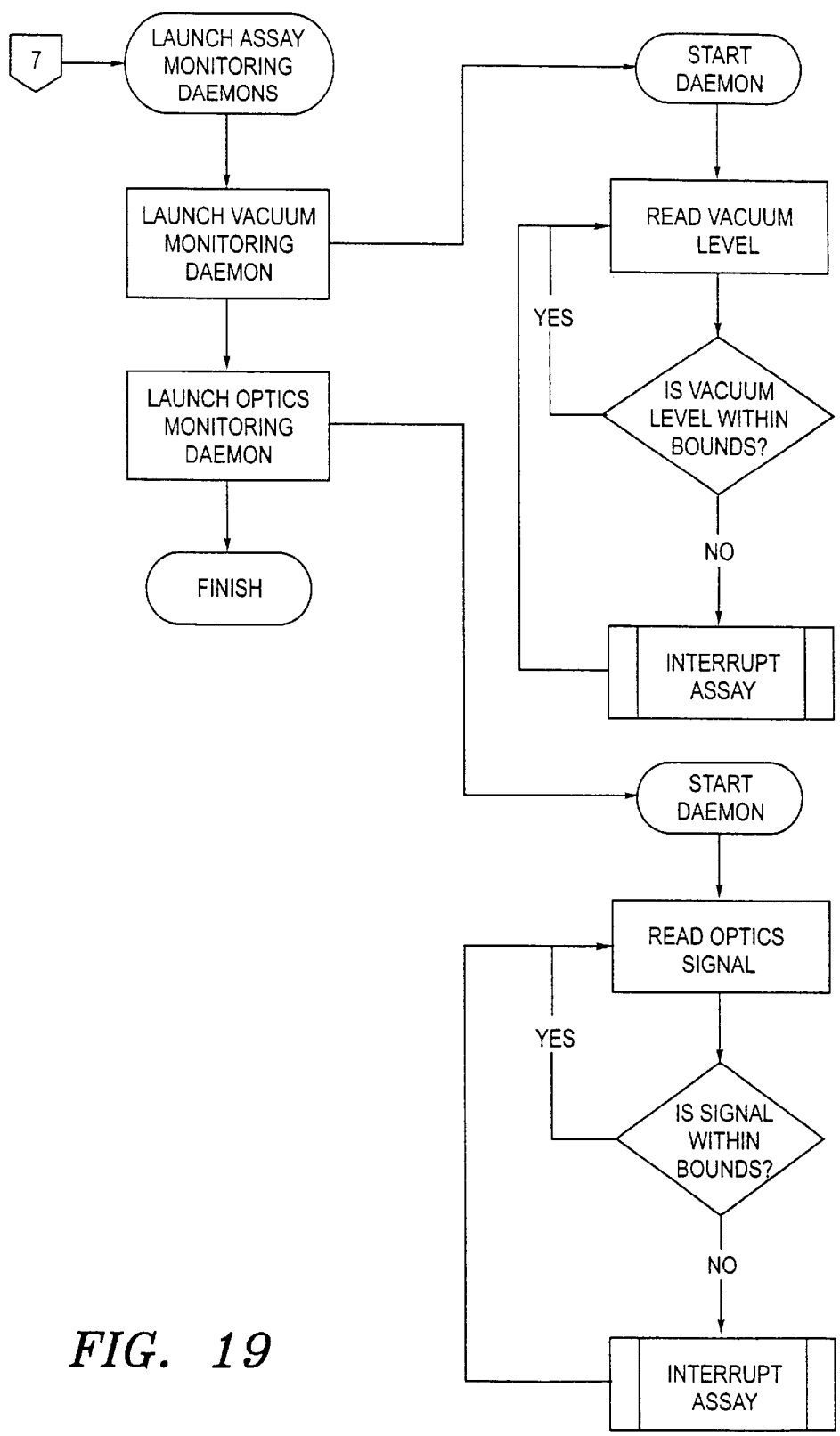
FIG. 19 depicts a system flow chart for the assay monitoring Daemon.

FIG. 15 depicts a preferred algorithm used to verify the lot information. FIG. 18 depicts a preferred system start up algorithm. The process insures that the assay cartridge is registered in the instrument correctly, that the cartridge has not been previously used, that the cartridge is within expiration dating, that the vacuum pump is on, and that the appropriate level of vacuum has been reached and that the optics are functioning correctly. Control point 7 (FIG. 19) determines that the vacuum level is within specification and the optical signal is within specification. Optics may also be monitored as a part of the startup daemon.

Figure 20B:
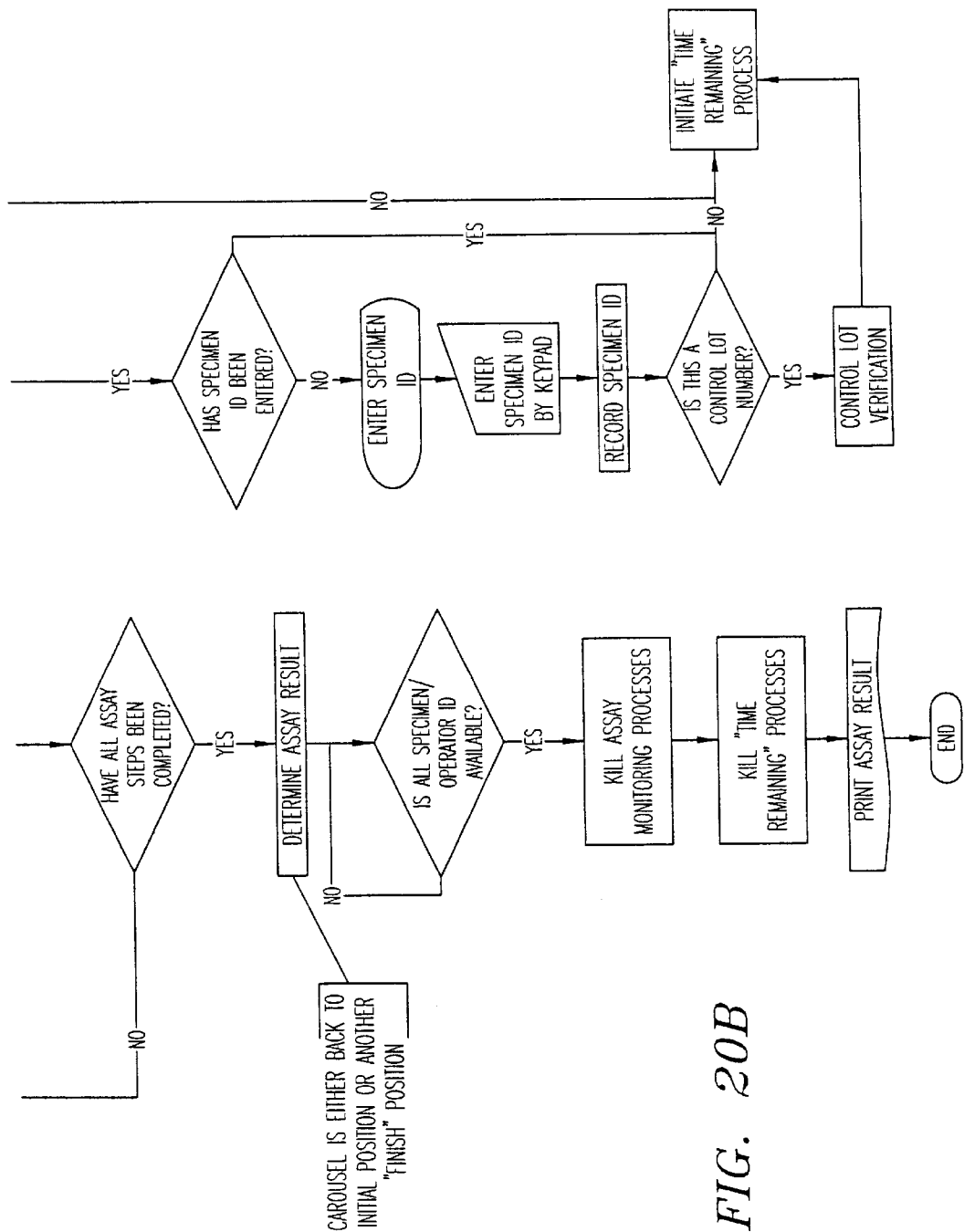
FIG. 20 depicts a system flow chart for the assay.

FIG. 20 depicts a preferred control algorithm for the assay procedure. In preferred embodiments, this algorithm is controls the highest level requirements for the assay procedure. Preferably, the algorithm insures that all of the components for the assay procedure are in place and within specification and controls the indexing of the assay cartridge to the proper processing positions for the selected assay procedure. It also provides for data output at the conclusion of the assay procedure. The algorithm has an internal control loop that must be satisfied for the assay to proceed. The control loop verifies that all required inputs have been entered or received. One skilled in the art will recognize that the control algorithm will depend on the steps required to perform a given assay.

Figure 21:
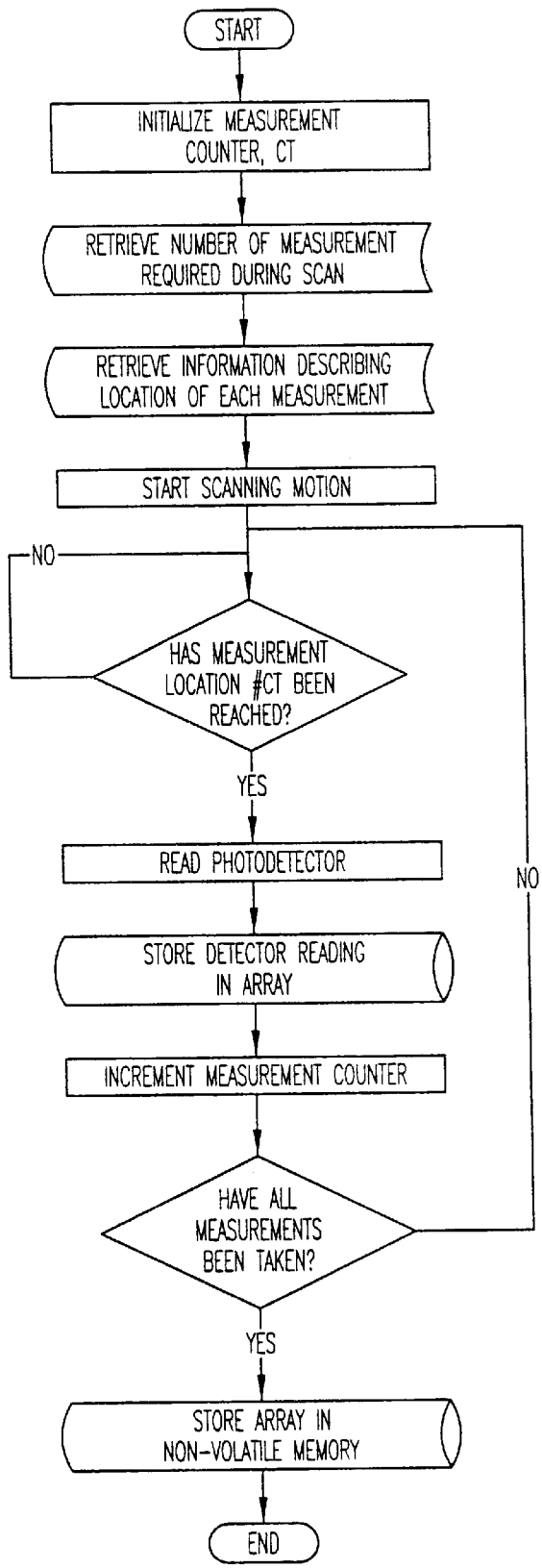
FIG. 21 depicts a system flow chart for the optical measurement.
Figure 22:
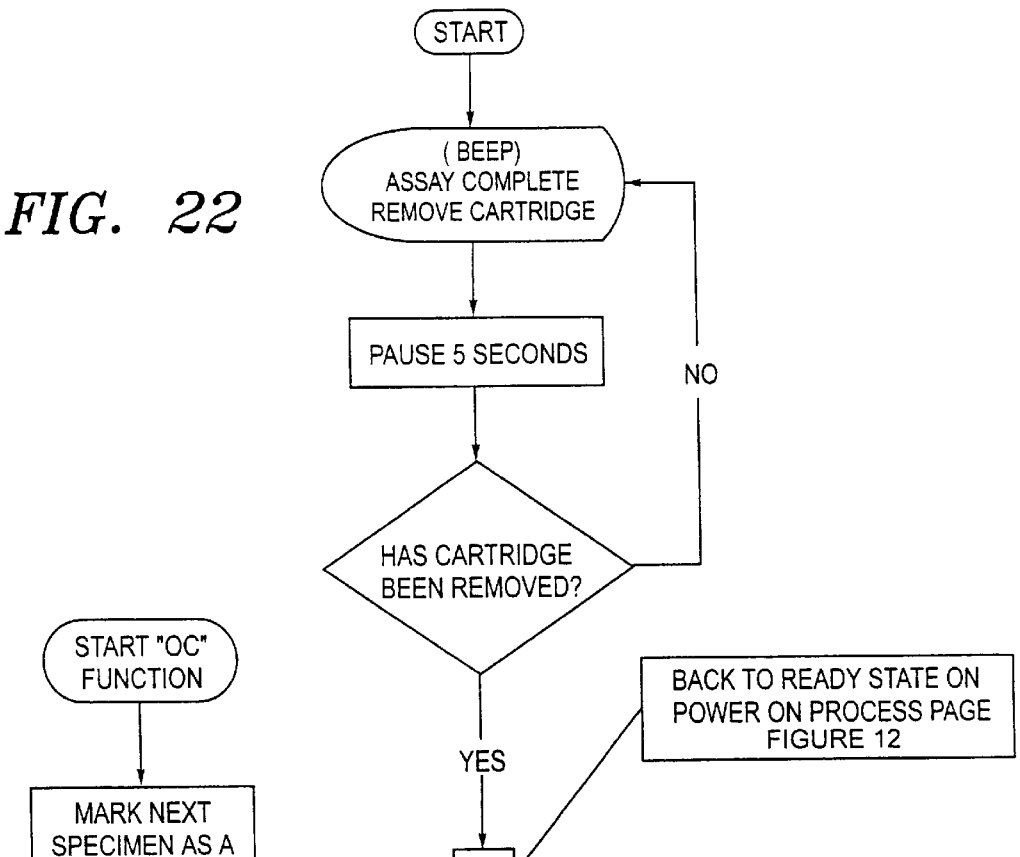
FIG. 22 depicts a system flow chart for the cartridge unloading.
Figure 23:
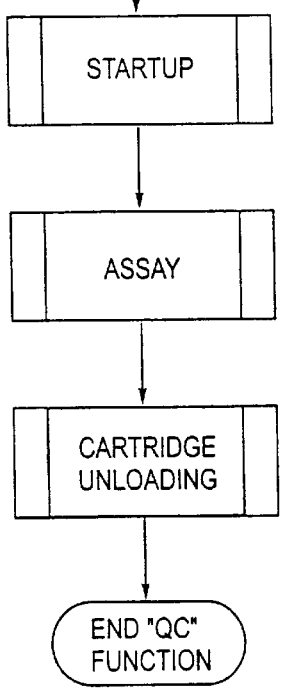
FIG. 23 depicts a system flow chart for instrument QC.
Figure 24A:
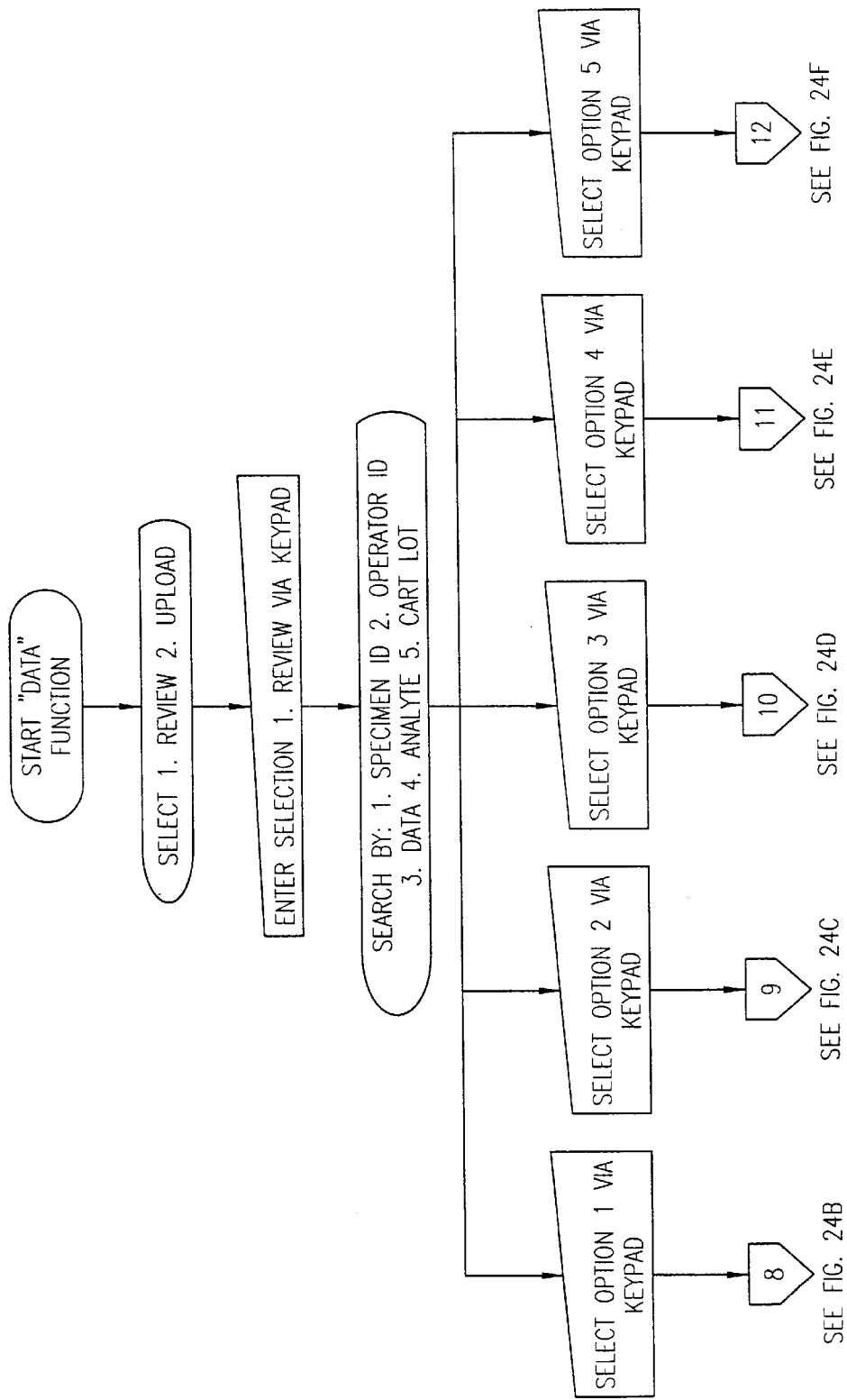
FIG. 24 depicts a system flow chart for data review.
Figure 24B:
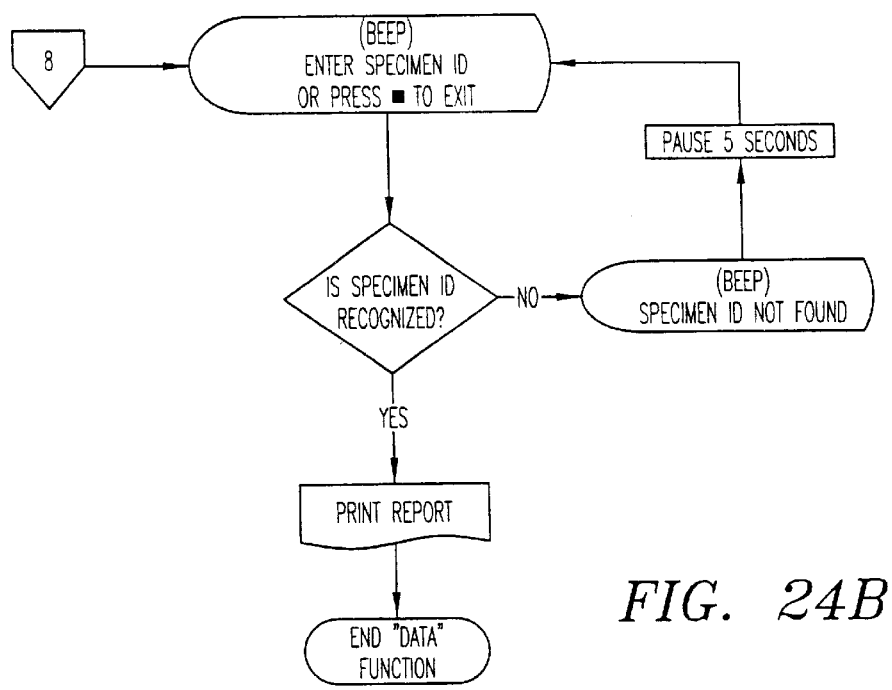
Figure 24C:
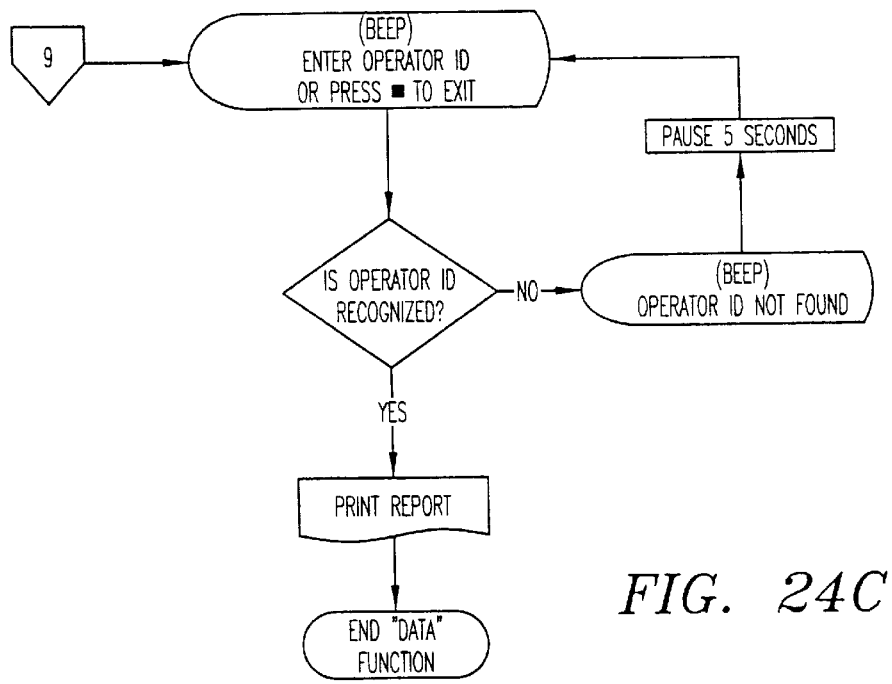
Figure 24D:
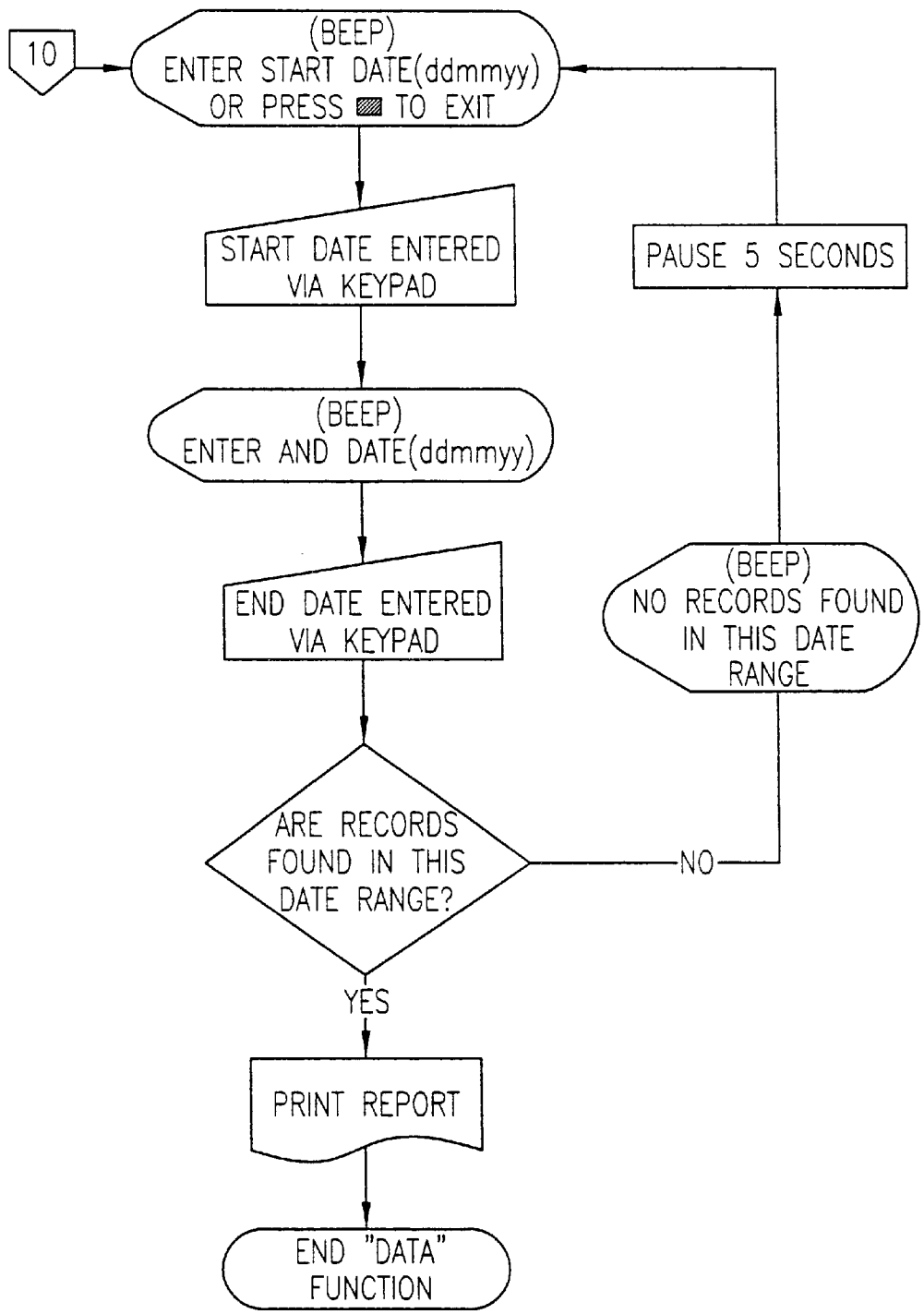
Figure 24E:
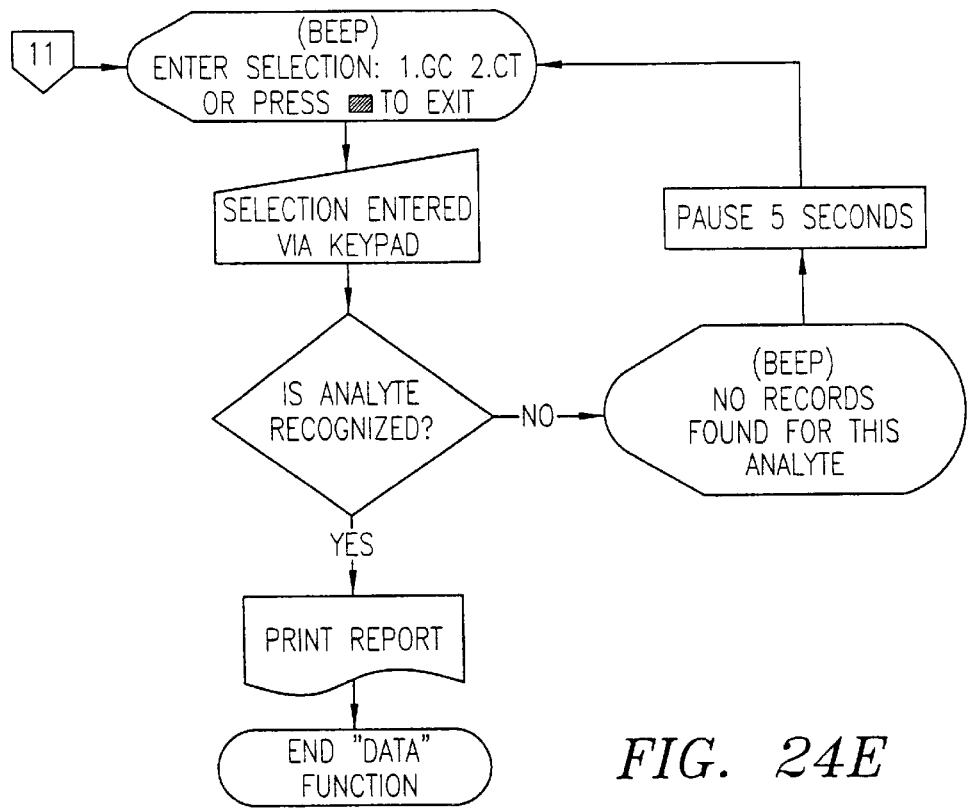
Figure 24F:
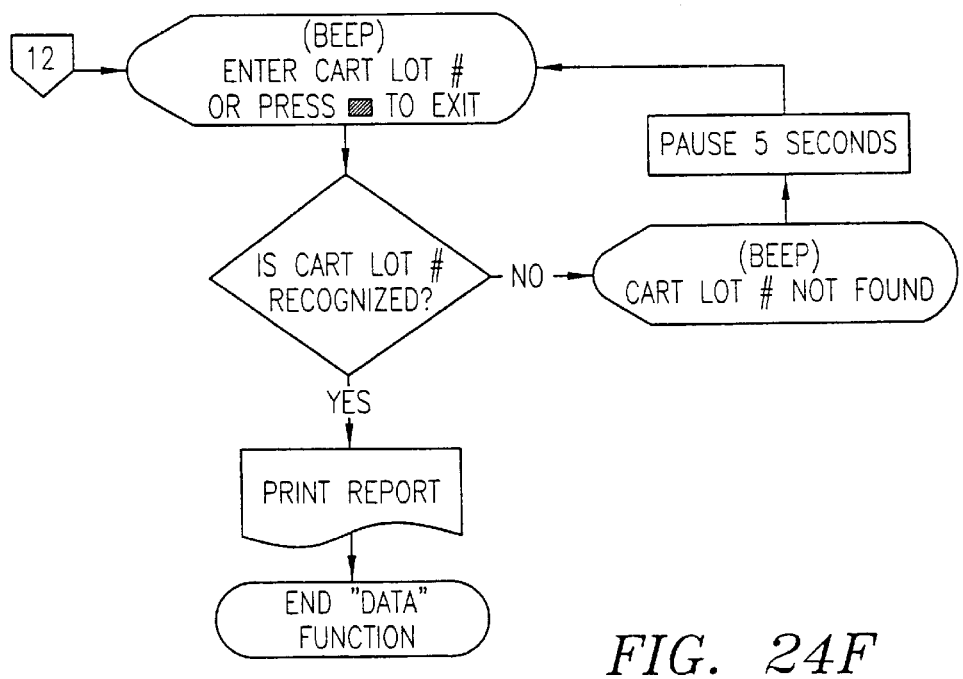

FIG. 21 depicts a preferred control algorithm for an optical measurement procedure. In certain embodiments, this algorithm controls the scanning of the reacted optically active test surface, the number of measurements made during the scan, and data storage. FIG. 22 depicts a preferred control algorithm for the unloading of a reacted assay cartridge and the return to the start position. In preferred embodiments, control point 5 allows the instrument to verify that an assay cartridge has been removed from the instrument, and returns the instrument to "ready" mode for insertion of a new assay cartridge. FIG. 23 depicts a preferred control algorithm for a QC process. Beyond identifying the run as a QC run the remaining protocol is the same as for a test sample.

Figure 25:
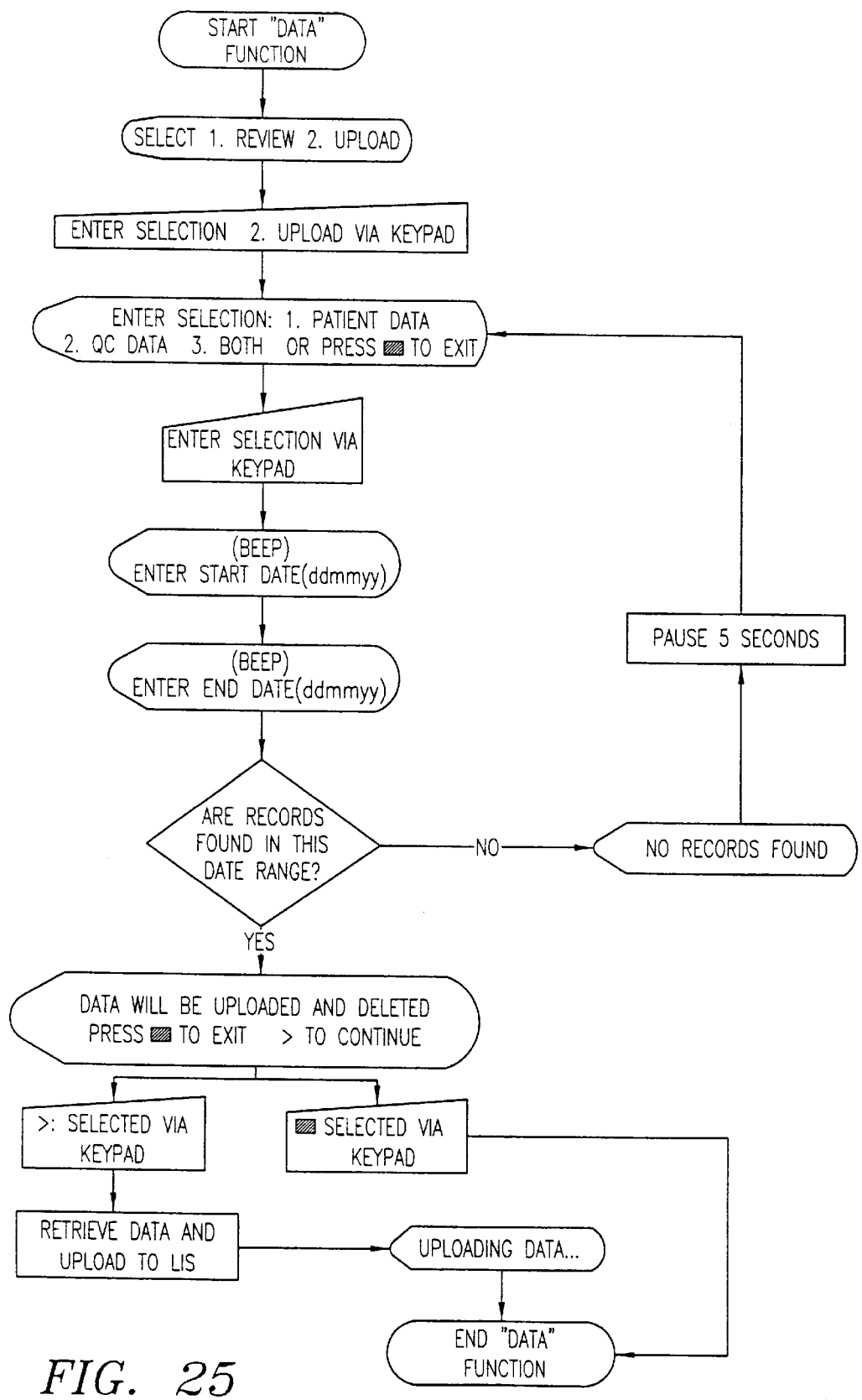
FIG. 25 depicts a system flow chart for data uploading.
Figure 26A:
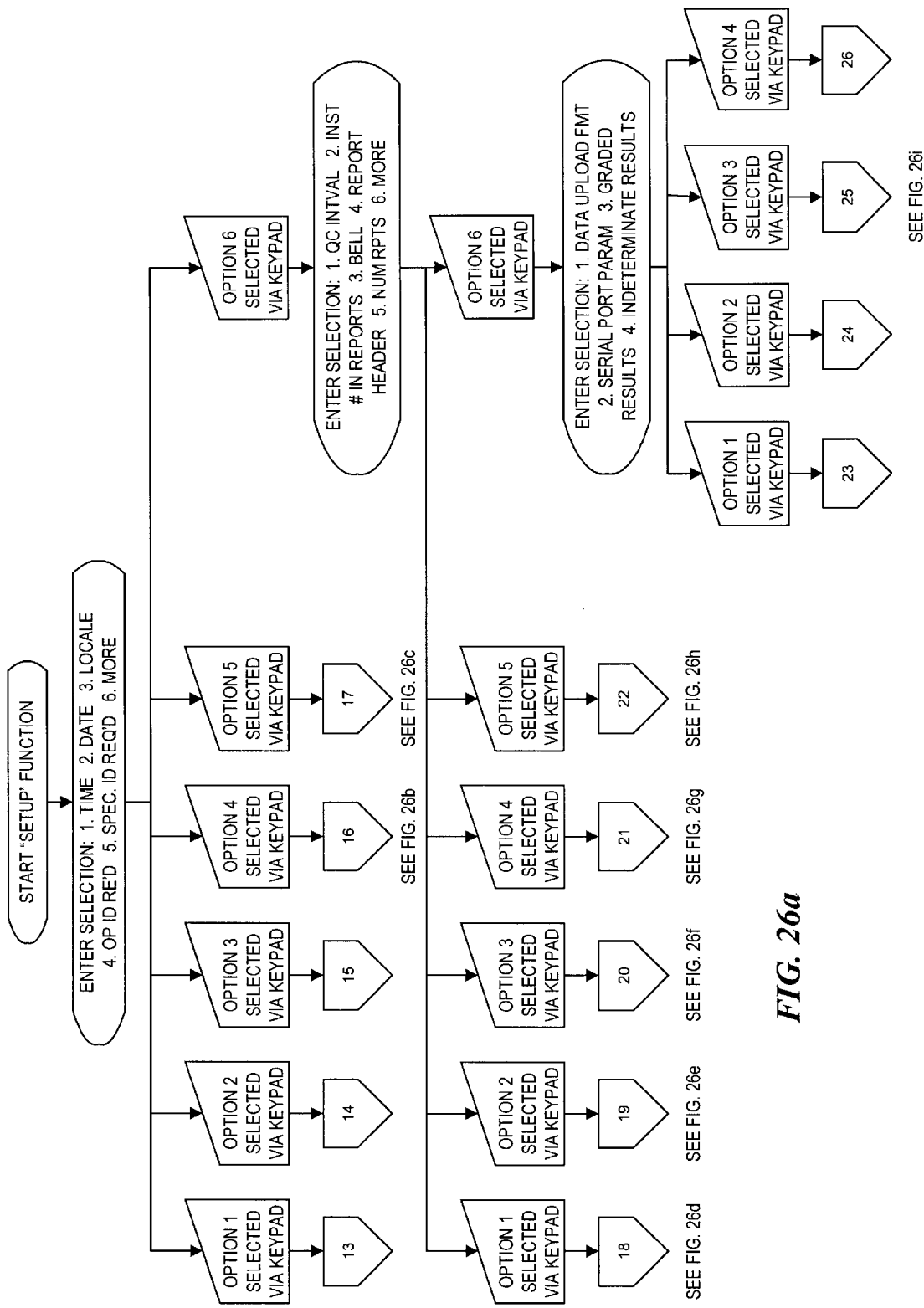
FIG. 26 depicts a system flow chart for set-up.
Figure 26B:
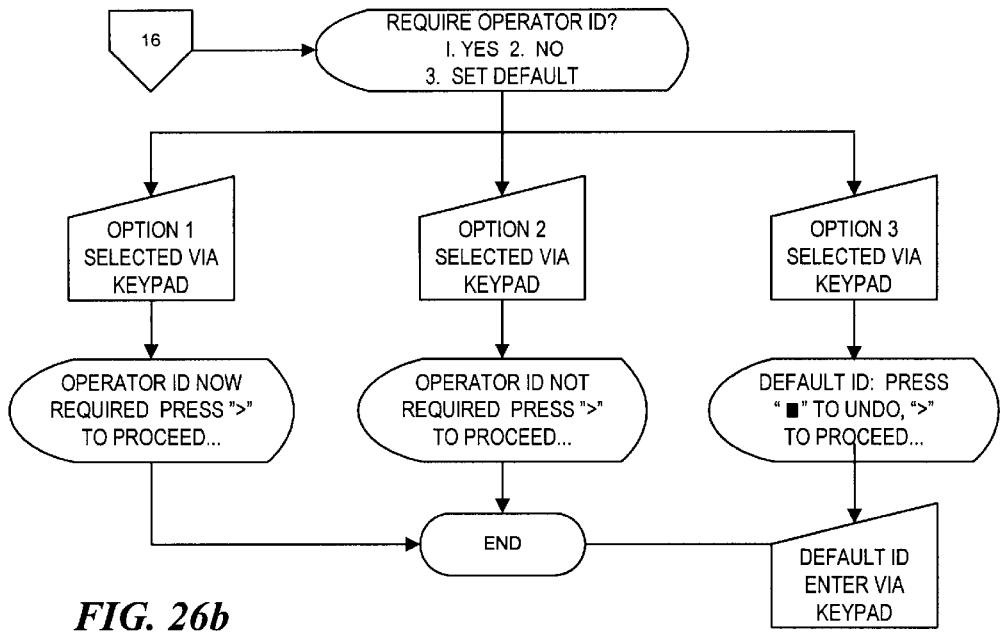
Figure 26C:
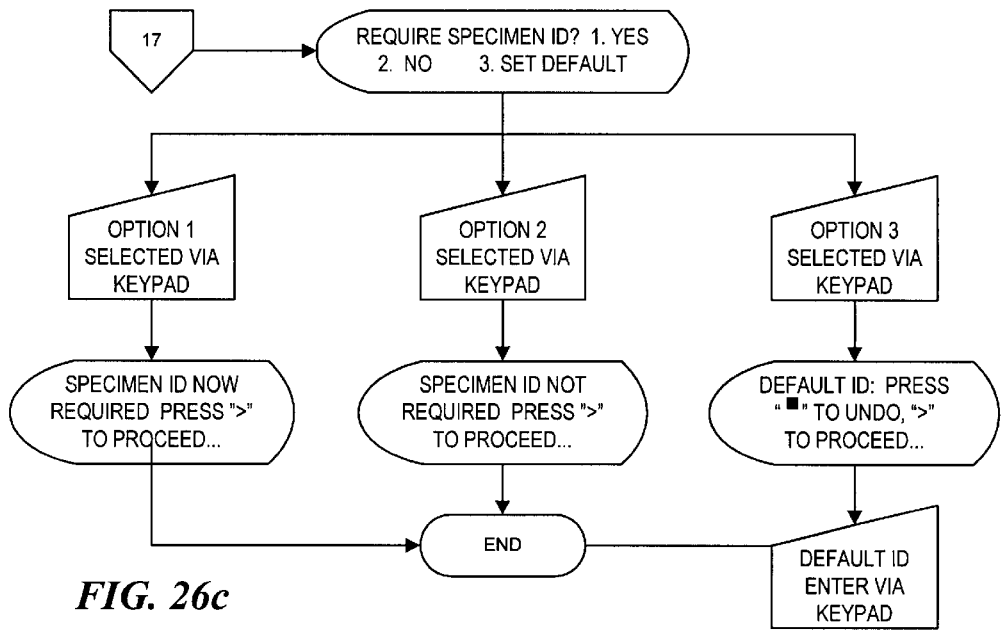
Figure 26D:
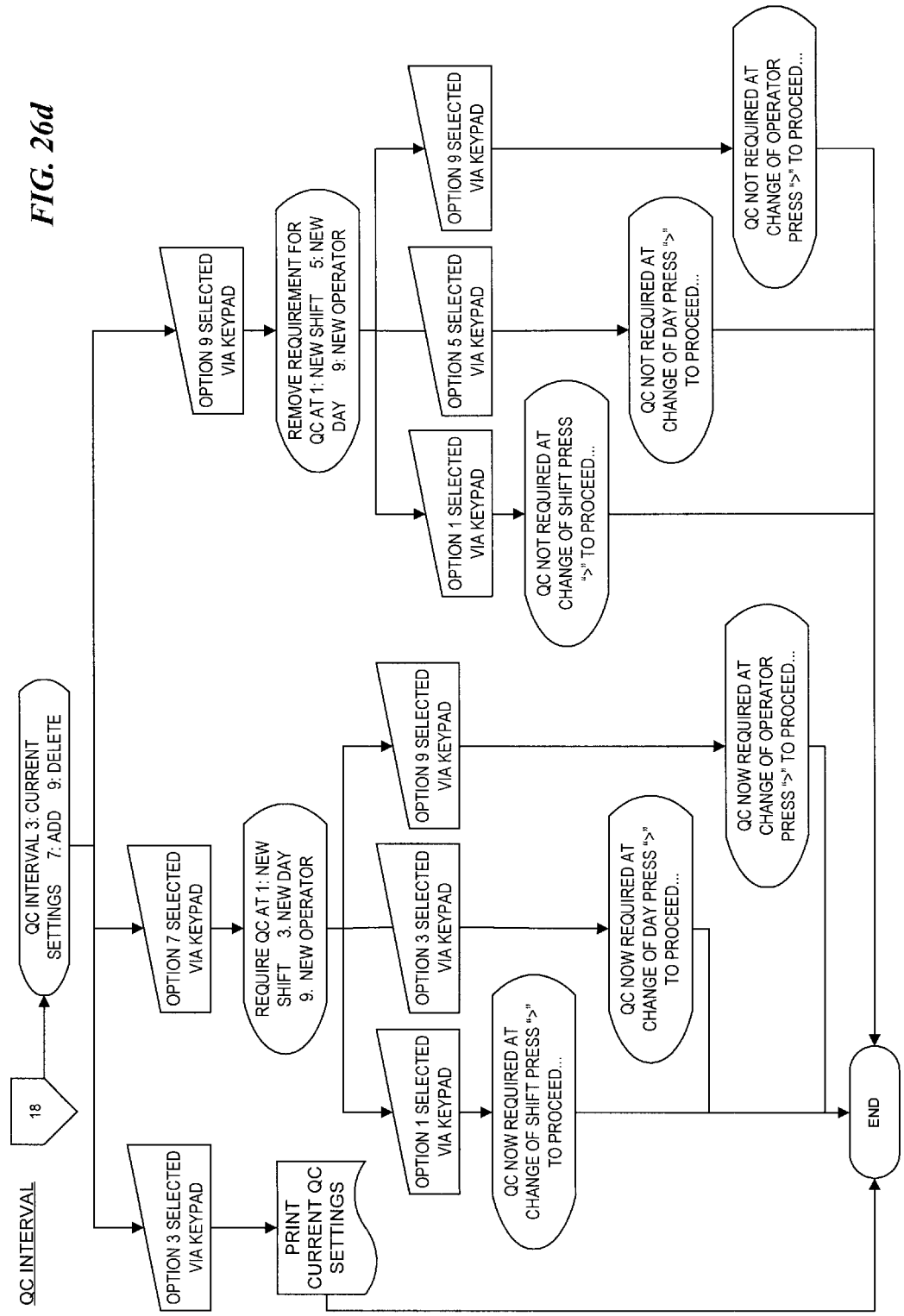
Figure 26E:
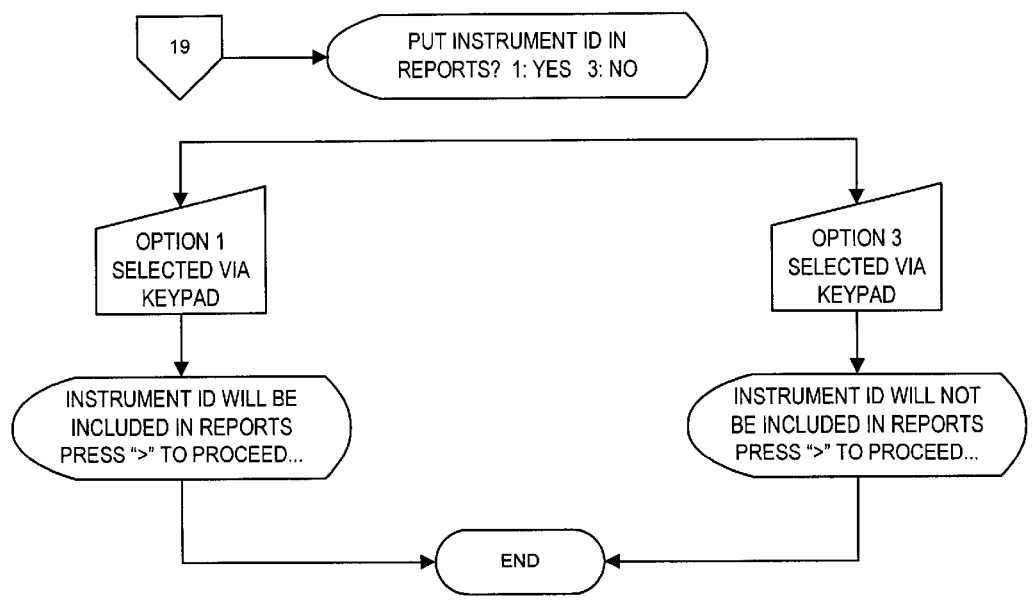
Figure 26F:
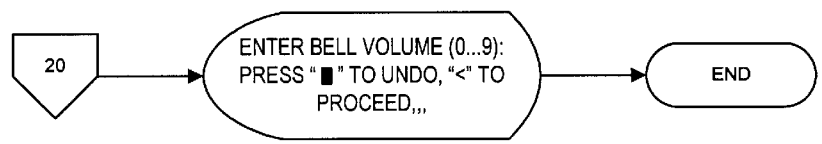
Figure 26G:
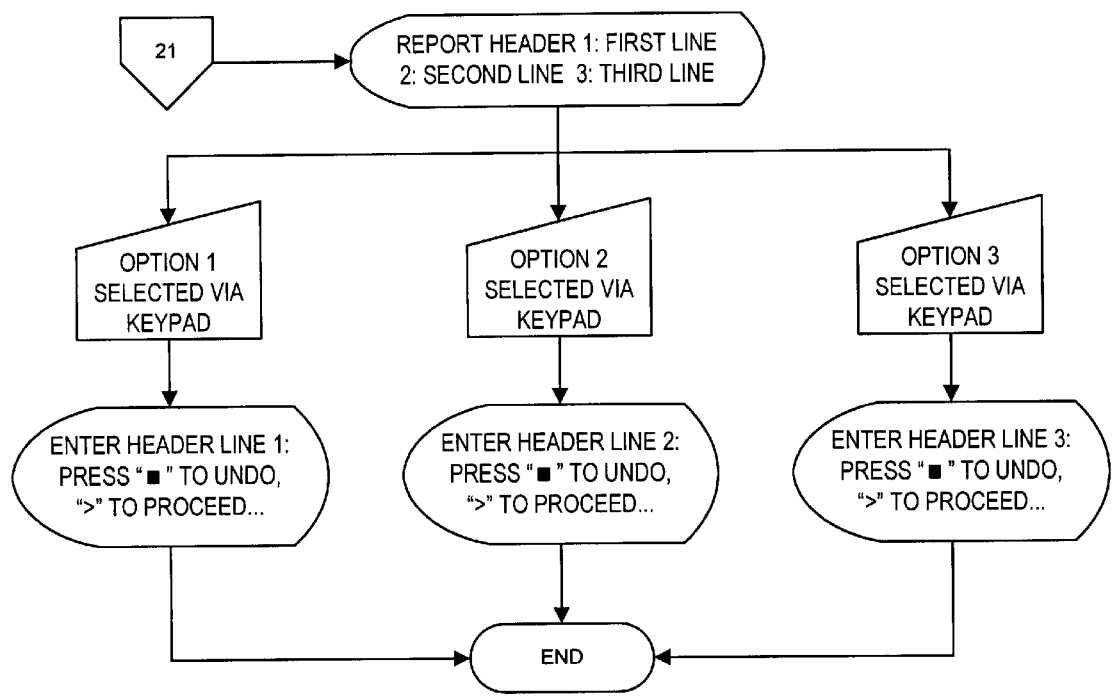
Figure 26H:
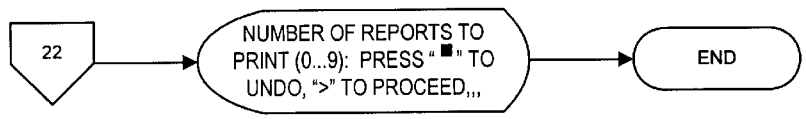
Figure 26I:
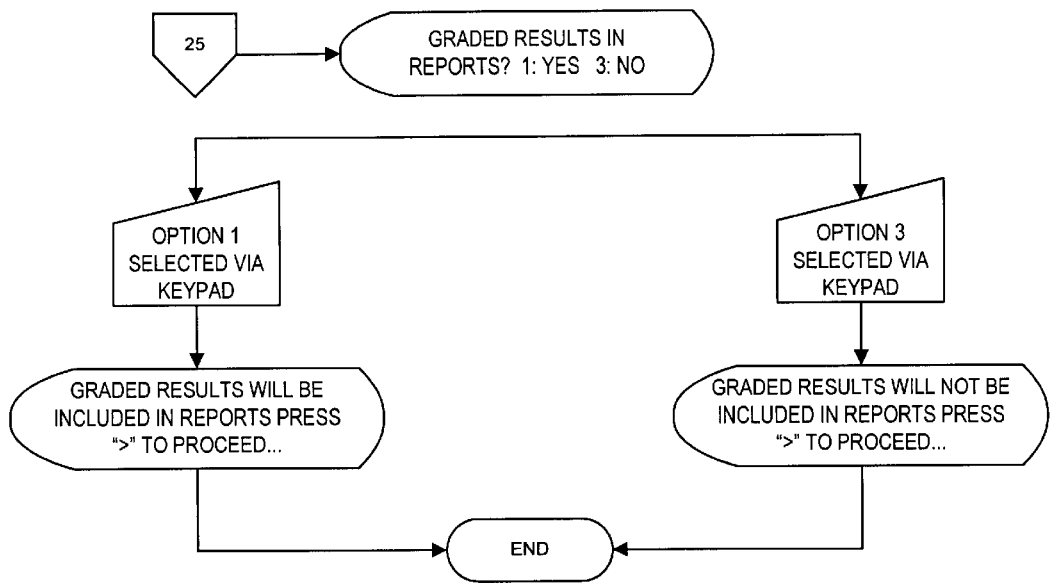

FIG. 24 depicts a preferred control algorithm for data review and the appropriate control points and control procedures. The appropriate processing function is selected based on the user choice of specimen identification, user identification, date, analyte, or cartridge designation. The control point 8 (FIG. 24b) allows data review by a specific specimen identification. Control point 9 (FIG. 24c) allows data to be reviewed by a specific operator identification. Control point 10 (FIG. 24d) allows data to be reviewed by a selected data set or range. Control point 11 (FIG. 24e) allows data to be reviewed by a specific analyte and control point 12 (FIG. 24f) allows data to be reviewed by a specific cartridge lot number. FIG. 25 depicts the control procedure for uploading data processing to a LIS or HIS. Data can be deleted upon uploading, or in an added separate function.

FIG. 26 depicts a preferred set-up control algorithm for an entire assay procedure. FIG. 26a is the highest level control chart and identifies control points 13–26. Control point 13 prompts the user to set a time and time format. Control point 14 prompts the user to set a date and date format. Control point 15 prompts the user to set a reporting language. Control point 16 (FIG. 26b) verifies that an operator identification was prompted for and entered or that a default identification was selected. Control point 17 (FIG. 26c) verifies that a specimen identification was prompted for and entered. Control point 18 (FIG. 26d) verifies that a QC specimen must be run if the user selects a new shift, new day, or new operator. Once the QC parameter is selected in the instrument set-up routine, the instrument will not allow any patient tests to be assayed until a QC specimen is ran when the QC parameter is changed. Control point 19 (FIG. 26e) verifies that the instrument identification is included in the report output generated. Control point 20 (FIG. 26f) verifies that the user has set an appropriate sound level for the system bells. Control point 21 (FIG. 26g) prompts the user to enter an appropriate report header. Control point 22 (FIG. 26h) prompts the user to enter the number of reports required for a single assay result. Control point 23 prompts the user to enter the data format for upload to LIS or HIS. Control point 24 prompts the user to set parameters for serial port connection to LIS or HIS. Control point 24 can also be present during instrument manufacture, and thus will not be required as a separate control point in the assay software. Control point 25 (FIG. 26i) provides the user the option of including graded or semi-quantitative results on a report in addition to a qualitative result. Control point 26 provides the user the option of using either a "+" or a "?" symbology on the report to represent an indeterminate result.

Figure 27:
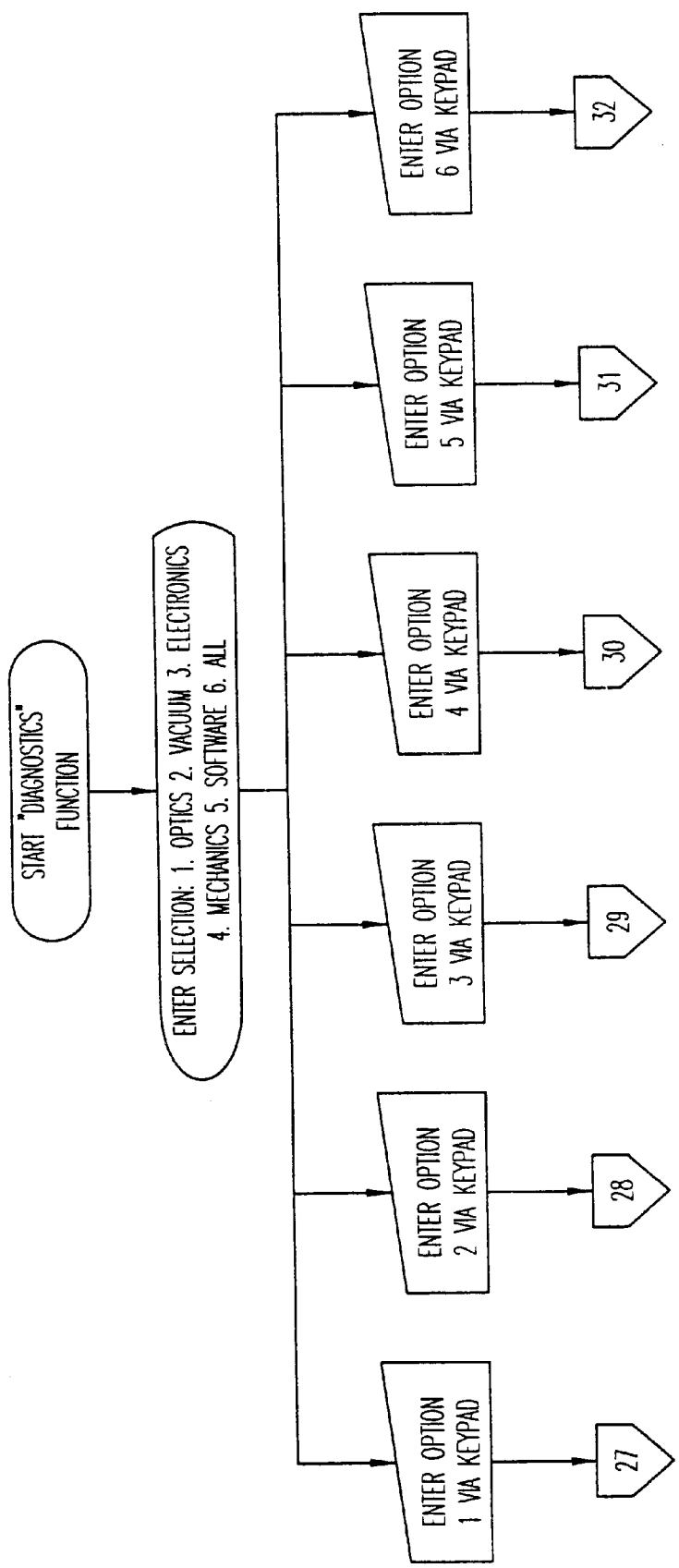
FIG. 27 depicts a system flow chart for diagnostics.

FIG. 27 depicts a preferred diagnostic processes for the various components of the instrument and their relation to the various assay procedures. Process flows 27–32 are not unique to every assay cartridge and assay procedure but are the highest level control processes required to assure that the various instrument components are active and within specification. These process flows may introduce a feedback loop into the self-check algorithms for monitoring purposes.

Figure 28:
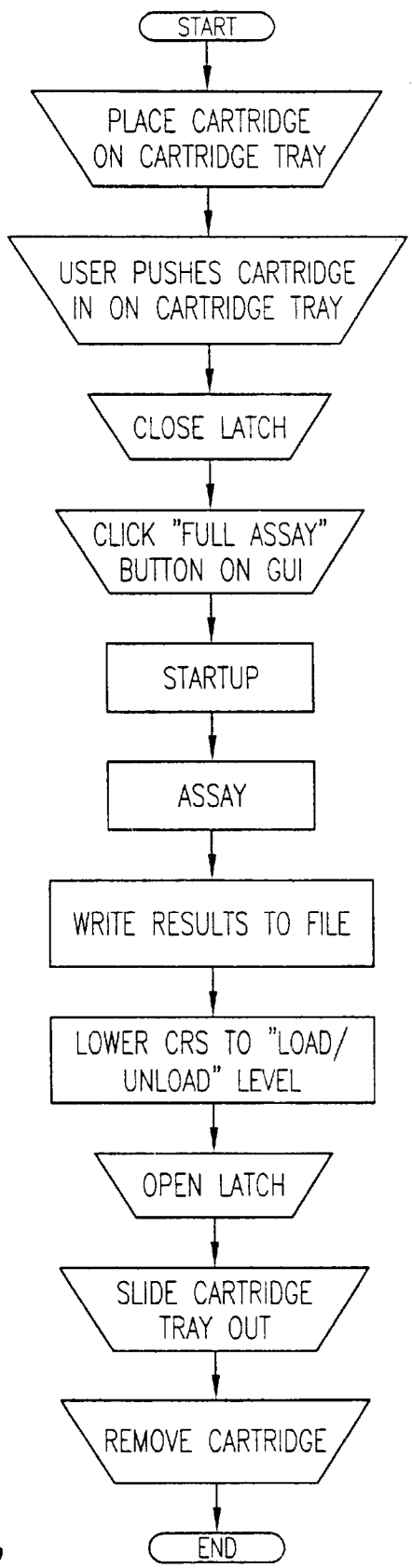
FIG. 28 depicts a system flow chart for main process; do-assay.
Figure 29:
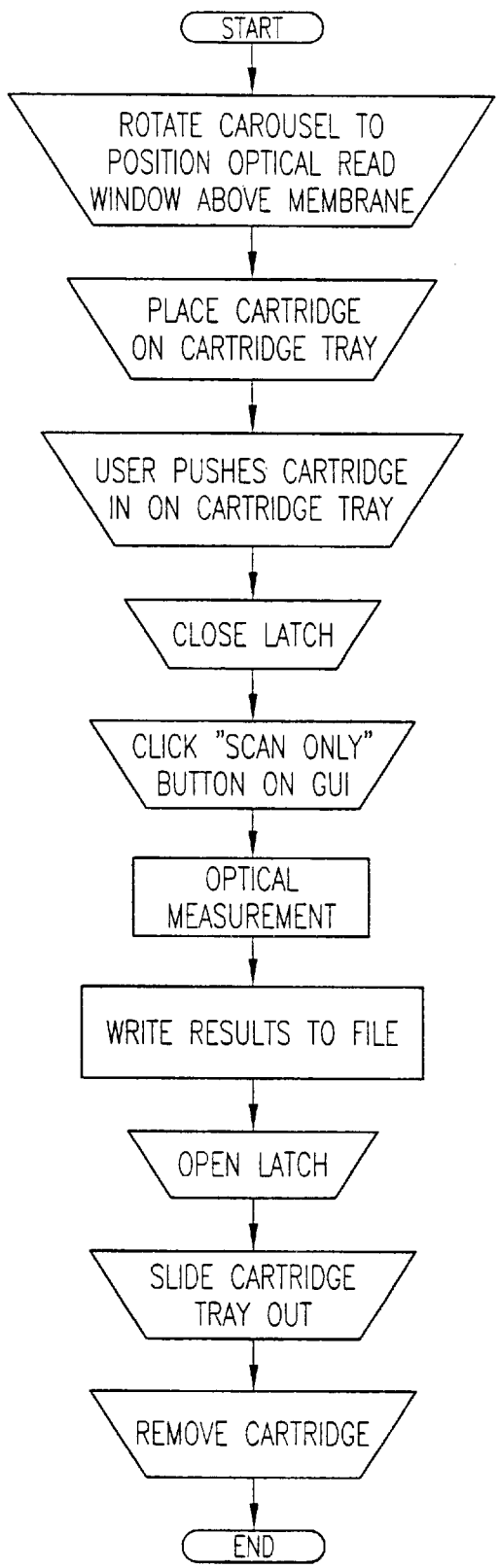
FIG. 29 depicts a system flow chart for main process; do-scan.
Figure 30:
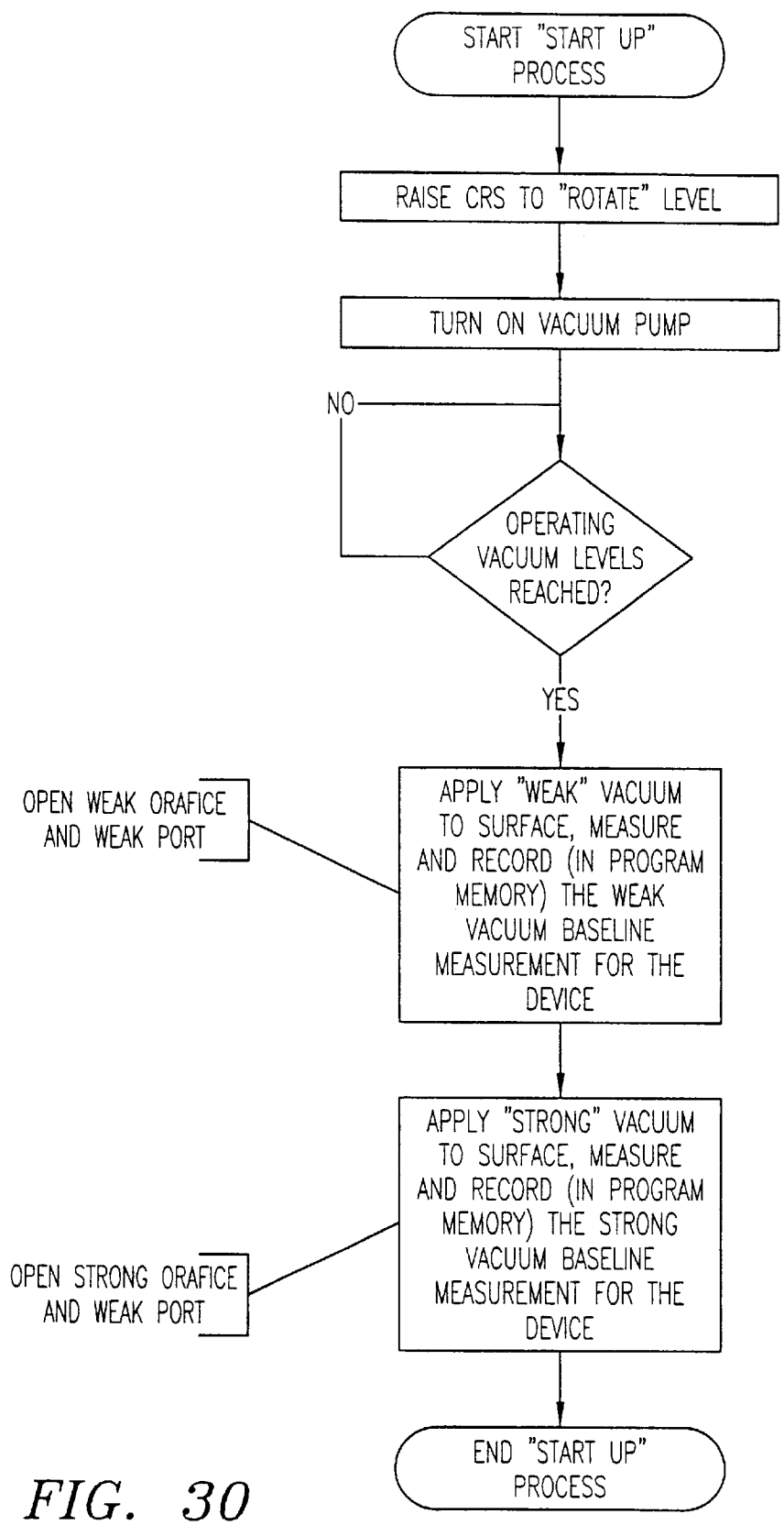
FIG. 30 depicts a system flow chart for start-up.
Figure 31:
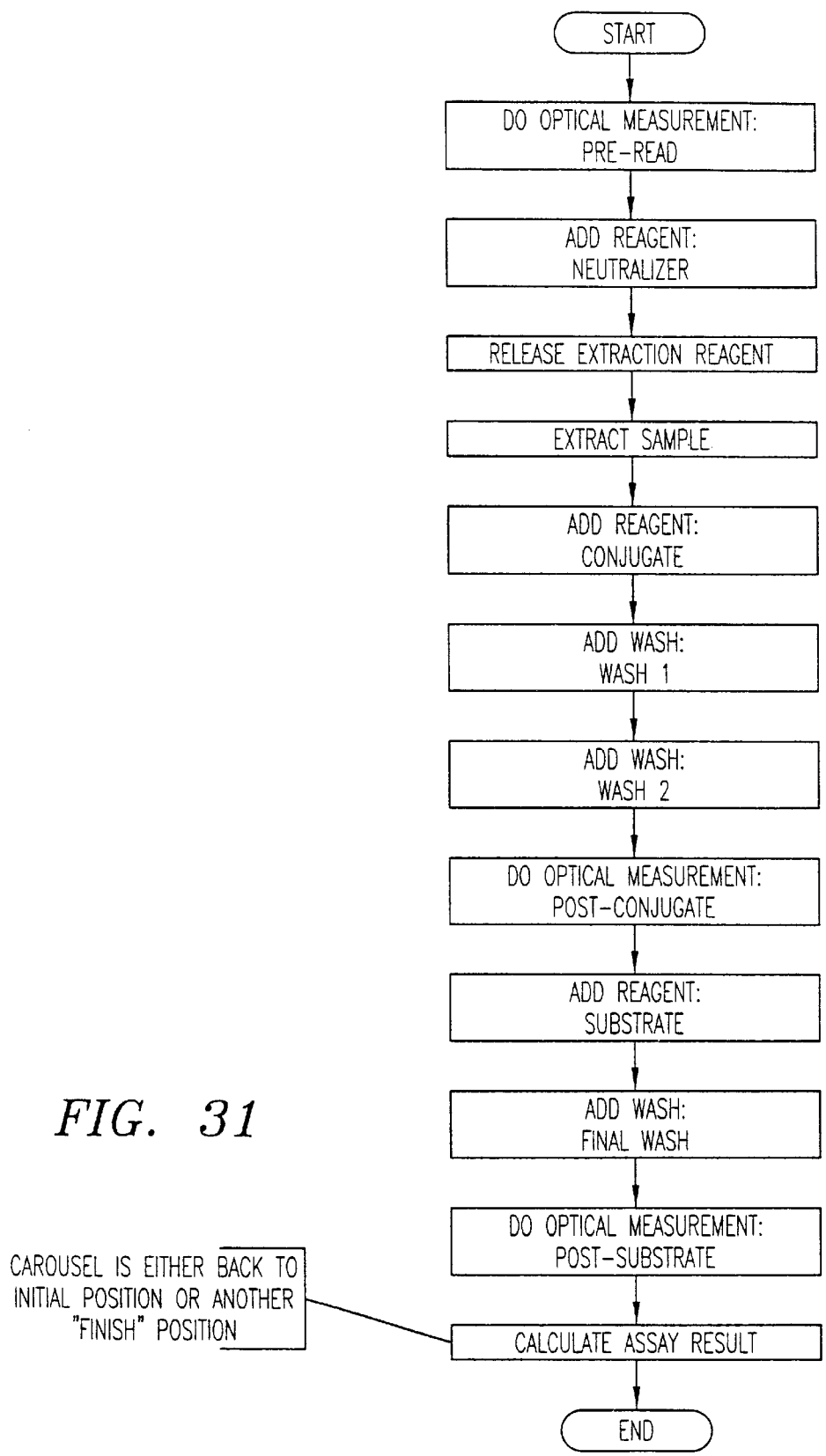
FIG. 31 depicts a system flow chart for assay.
Figure 32:
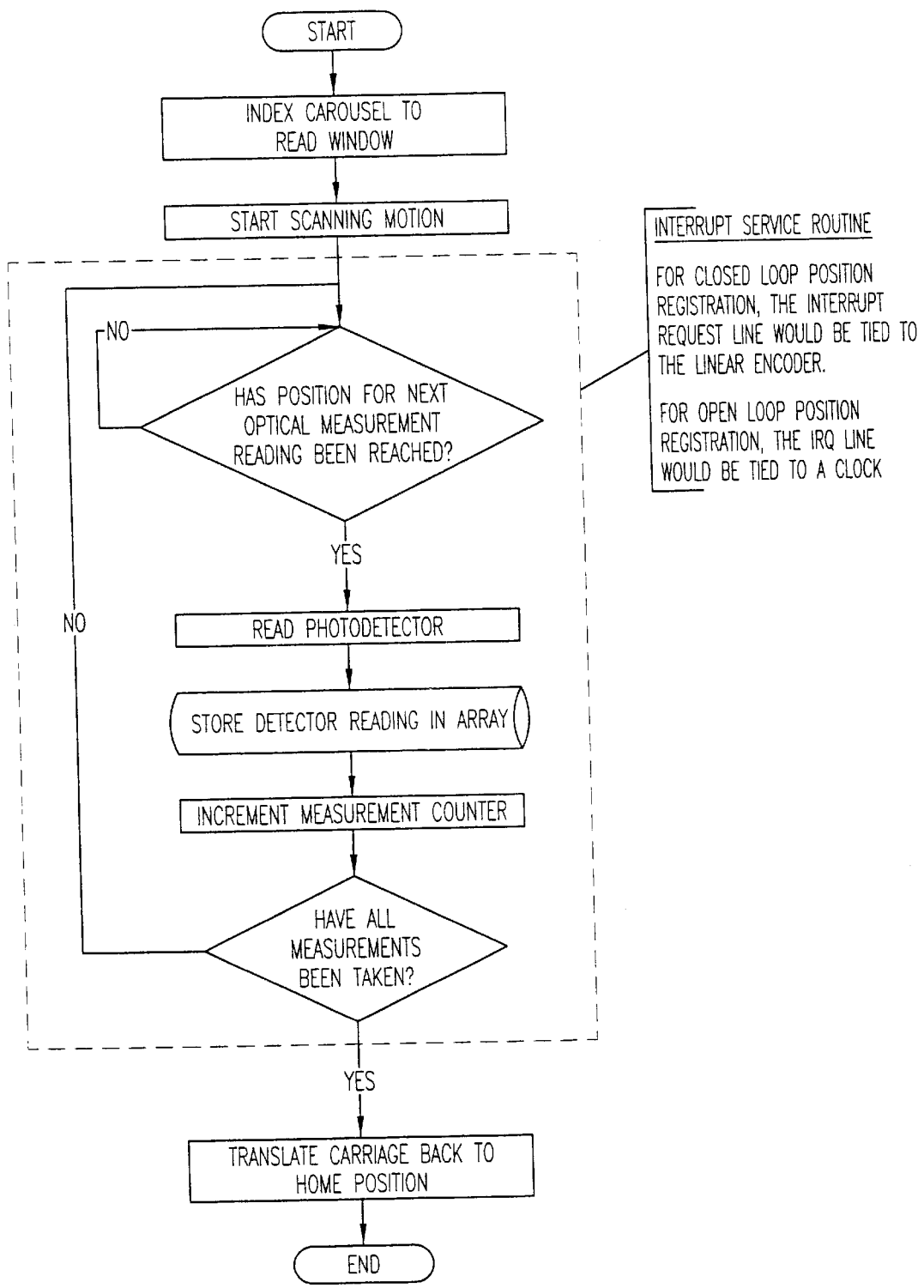
FIG. 32 depicts a system flow chart for optical measurements.
Figure 33:
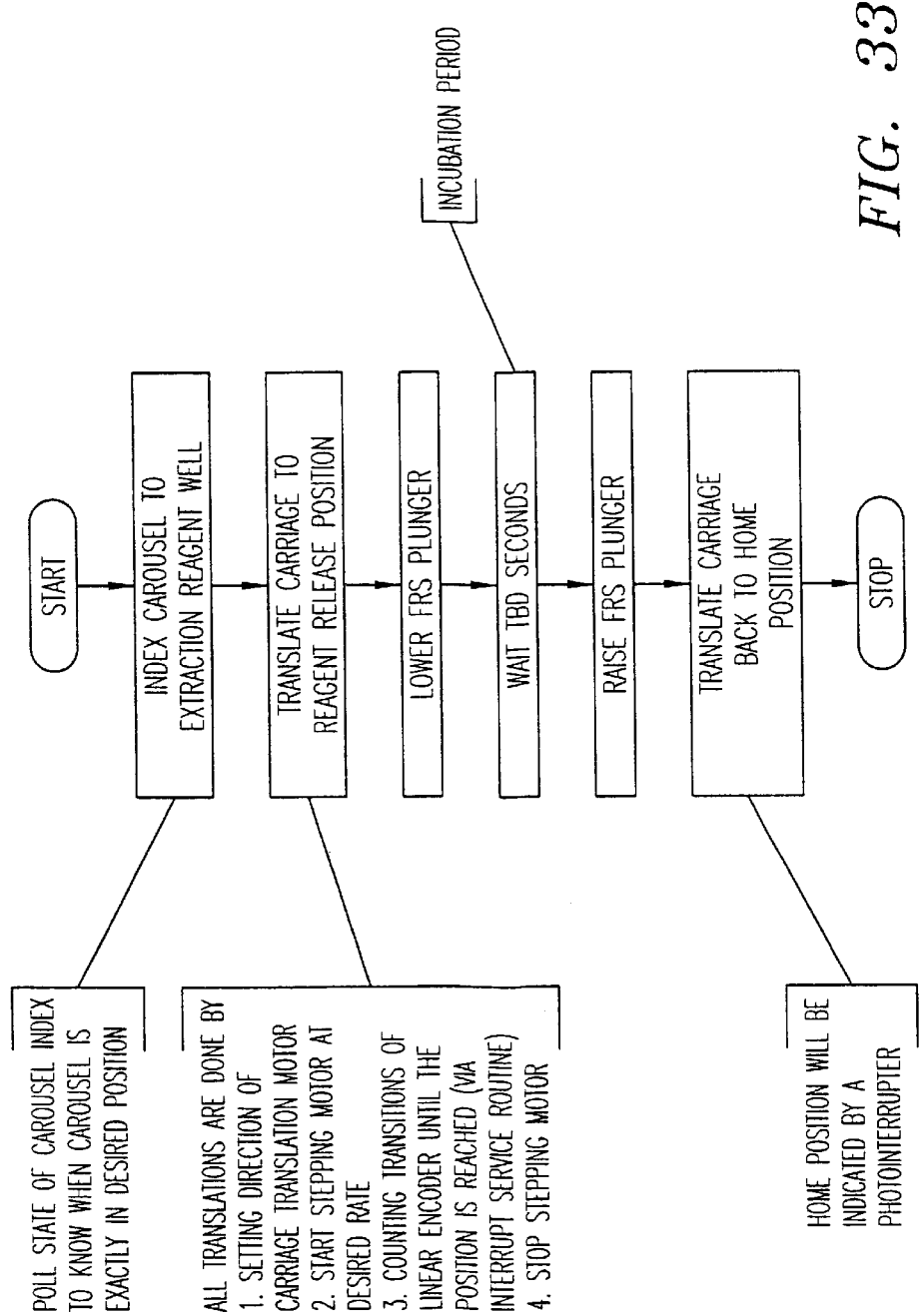
FIG. 33 depicts a system flow chart for releasing extraction reagent.
Figure 34:
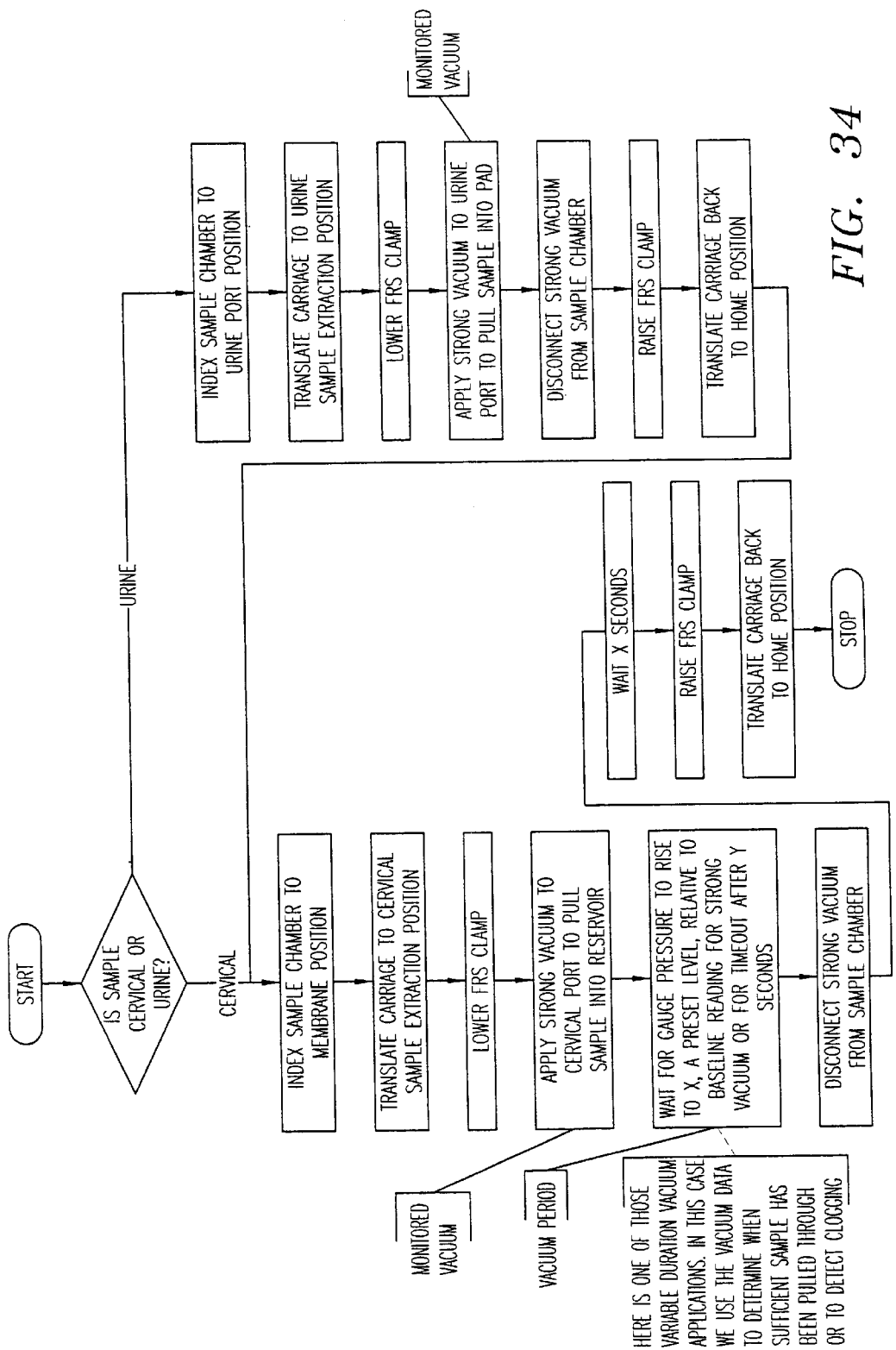
FIG. 34 depicts a system flow chart for extracting the sample.
Figure 35:
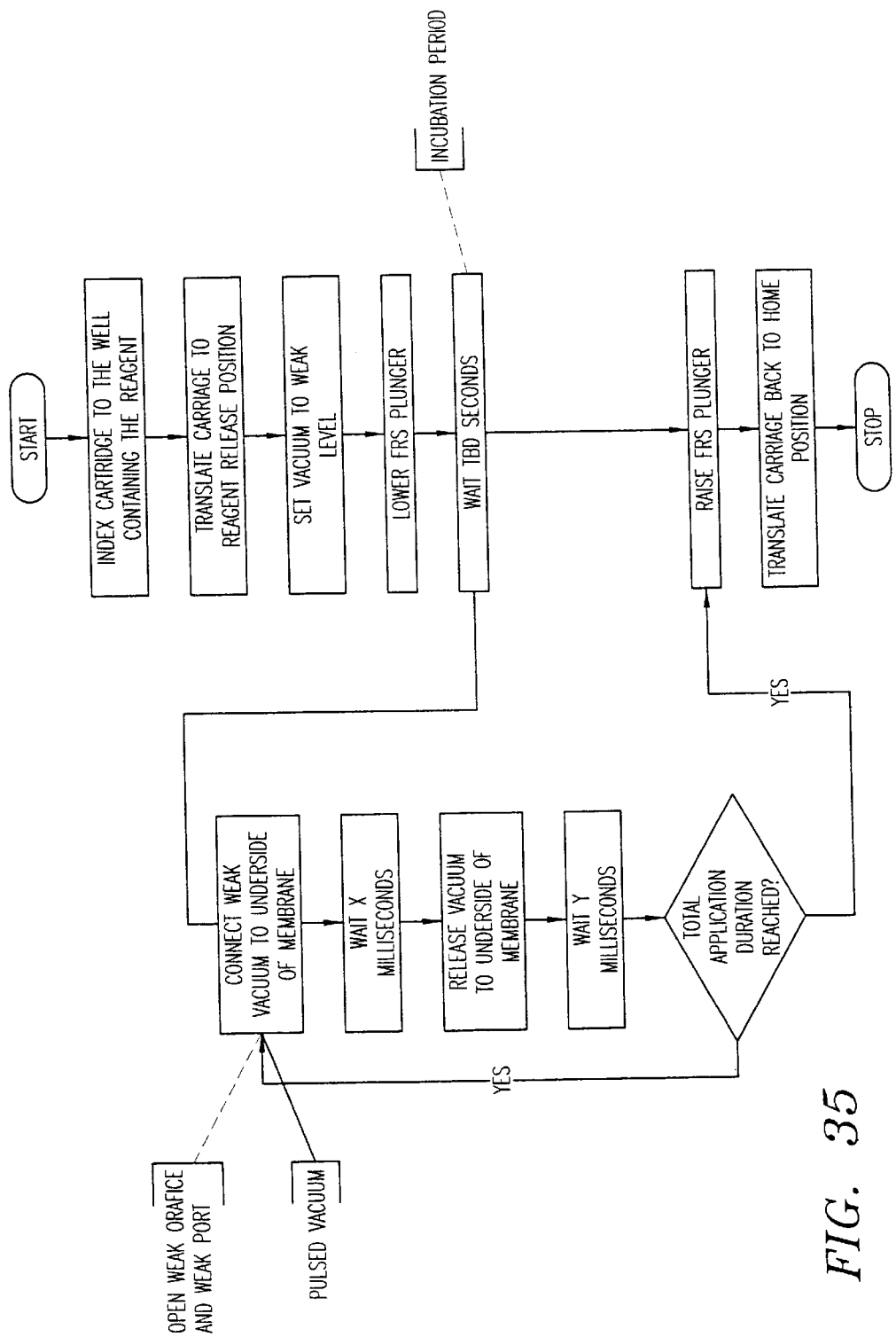
FIG. 35 depicts a system flow chart for adding reagent to the optically active surface or membrane.

FIG. 28 depicts preferred general assay procedure requirements in the sequence required to produce a final result. FIG. 29 depicts the general sequence required to complete the optical scanning process and the cartridge handling required to allow for the optical scanning procedure. FIG. 30 depicts the general sequence required for the vacuum control in the assay procedure. FIG. 31 depicts a general assay sequence of processing requirements. This protocol may accommodate a number of different analyte-specific testing protocols. However, the number and sequence of the processing steps may be adjusted to accommodate any analyte-specific test protocol. FIG. 32 depicts the processing sequence for the optical reading of the optically active test surface within the assay cartridge. FIG. 33 depicts one possible extraction reagent addition sequence. FIG. 34 completes one possible extraction sequence for an analyte-specific testing protocol. FIG. 35 depicts the sequence of processing steps required for reagent addition to an optically active test surface or membrane. This is one possible sequence of processing steps that is dependent on the analyte-specific test being performed. This protocol may be applicable to a number of analyte-specific tests.

Figure 36:
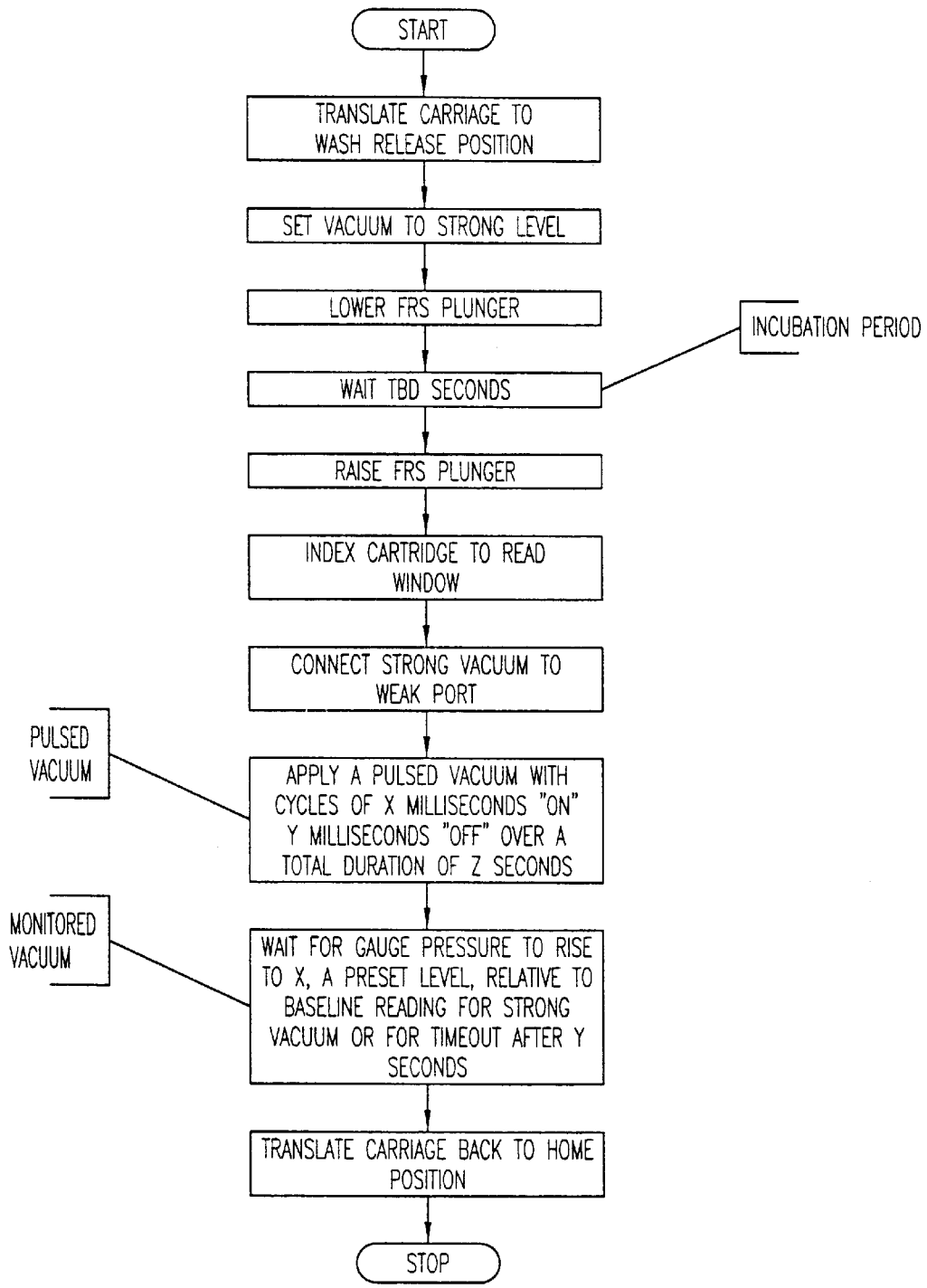
FIG. 36 depicts a system flow chart for adding wash to the optically active surface or membrane.
Figure 37A:
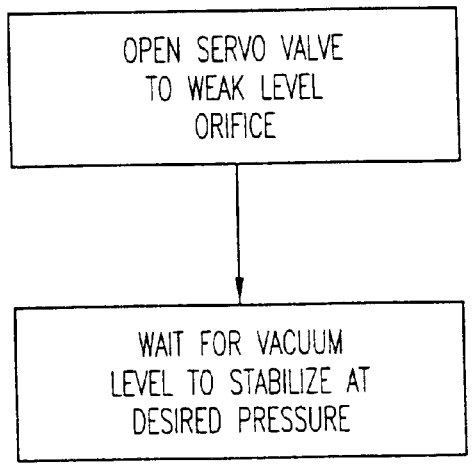
FIG. 37 depicts a system flow chart for other sub-processes.
Figure 37B:
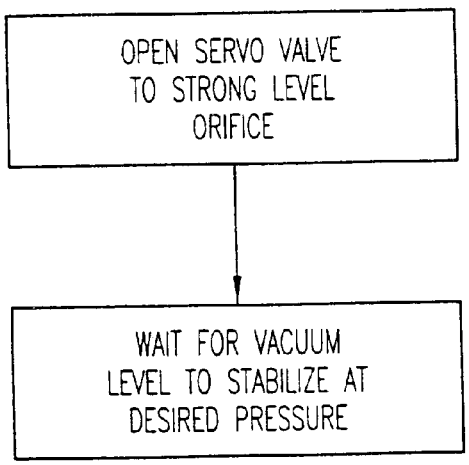

FIG. 36 depicts one possible sequence for a wash cycle on the optically active test surface or membrane. The wash cycles within a single assay procedure and between analyte-specific testing procedures may differ in a number of parameters. These parameters include the time wash is allowed to contact the surface prior to application of vacuum, the use of an air flow over the surface to facilitate drying of the test surface, the vacuum pulse times and pressure. Other parameters include the pressure level maintained and the time that level is maintained, etc. Drying of the test surface may be related to the vacuum pressure. The same level of drying may not be required following each wash step and the same level of drying may not be required for different types of test surfaces. When an optically active test surface is to be optically scanned the surface must be dry. FIG. 37 depicts the vacuum level considerations and procedures.

Figure 38:
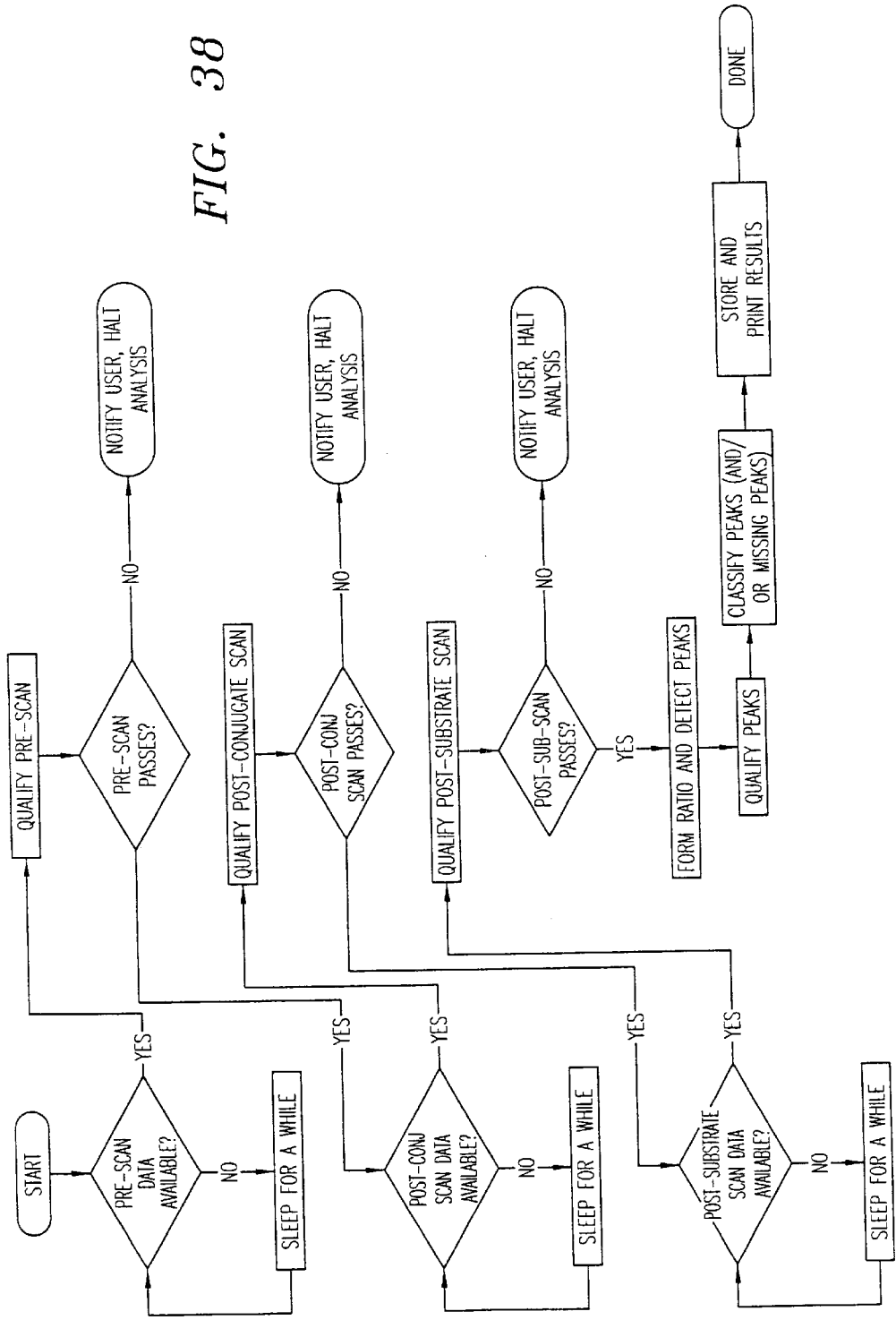
FIG. 38 depicts the highest-level data qualification/classification algorithm.
Figure 39:
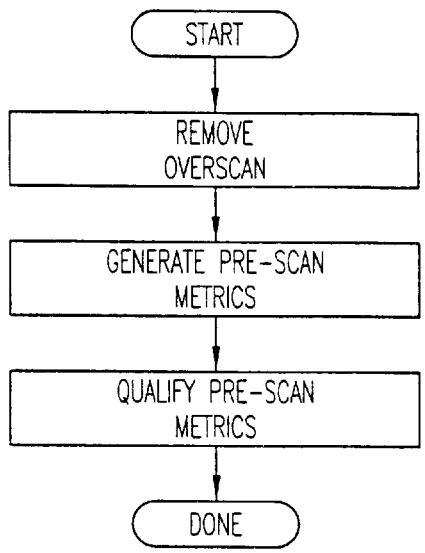
FIG. 39 depicts the data qualification/classification algorithm for the pre-scan qualification.
Figure 40:
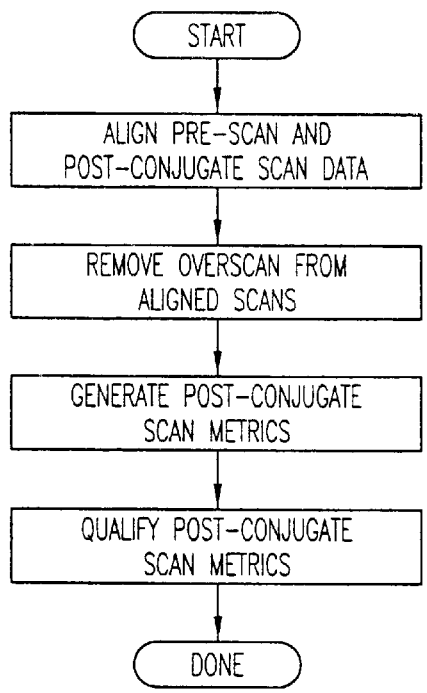
FIG. 40 depicts the data qualification/classification algorithm for the post-conjugate scan qualification.
Figure 41:
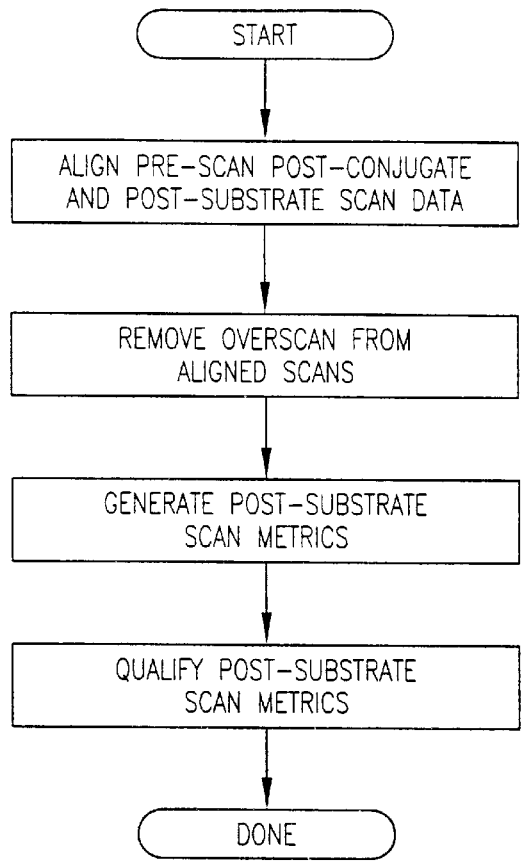
FIG. 41 depicts the data qualification/classification algorithm for the post-substrate scan qualification.
Figure 42:
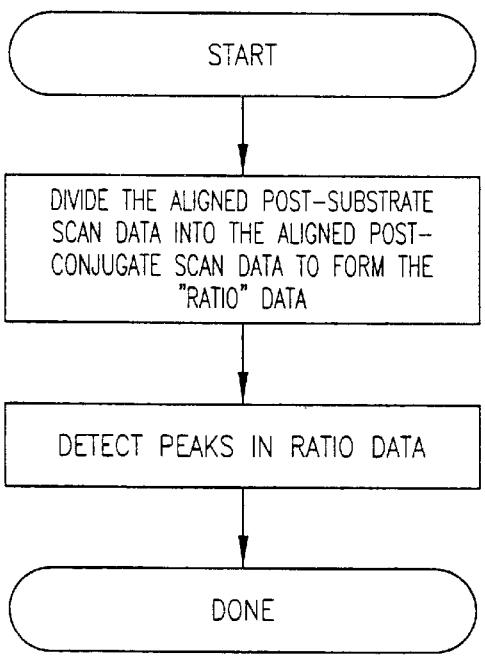
FIG. 42 depicts the data qualification/classification algorithm for the form ratios and detect peaks.
Figure 43:
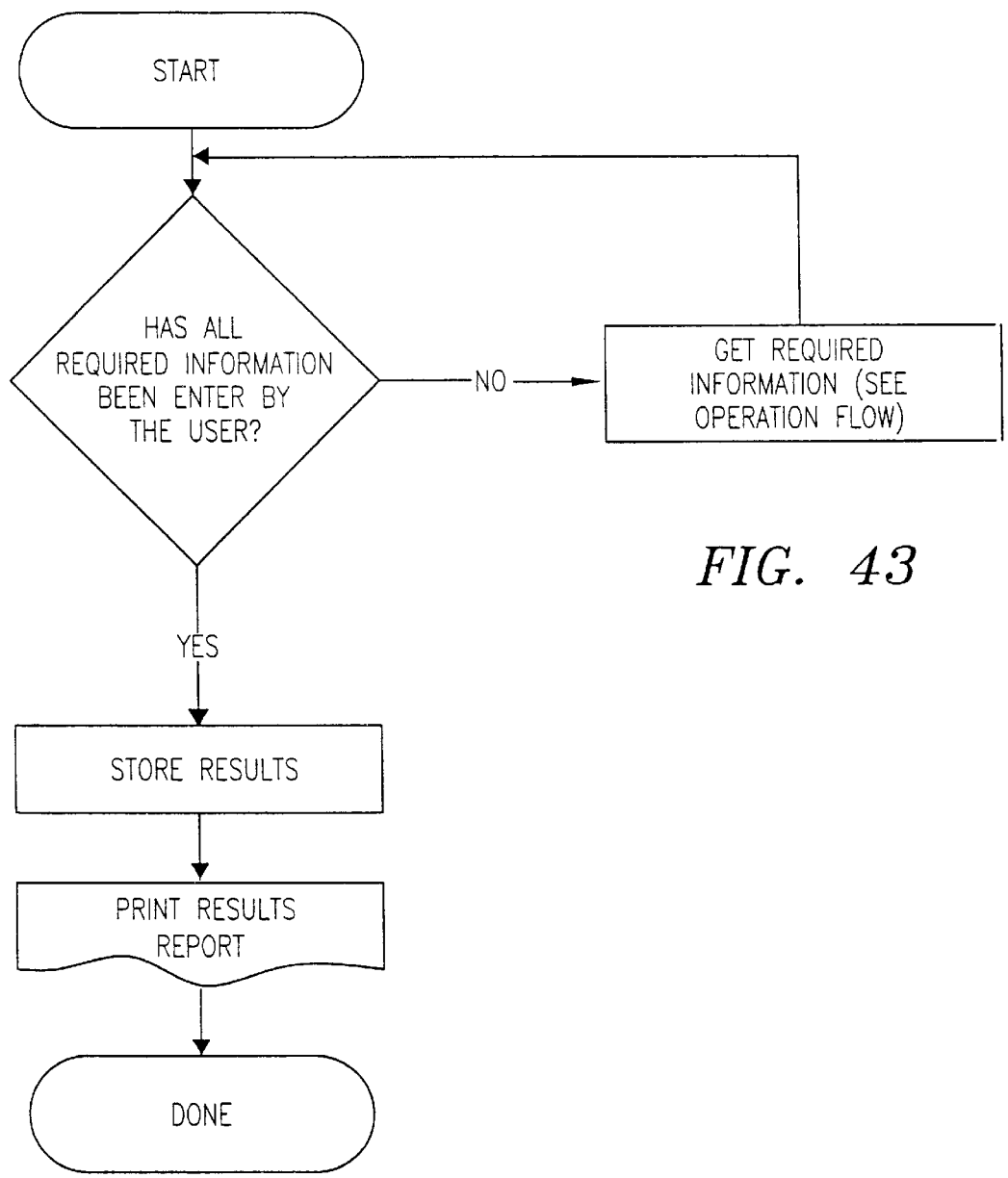
FIG. 43 depicts the data qualification/classification algorithm for the storage and printing of results.
Figure 44:
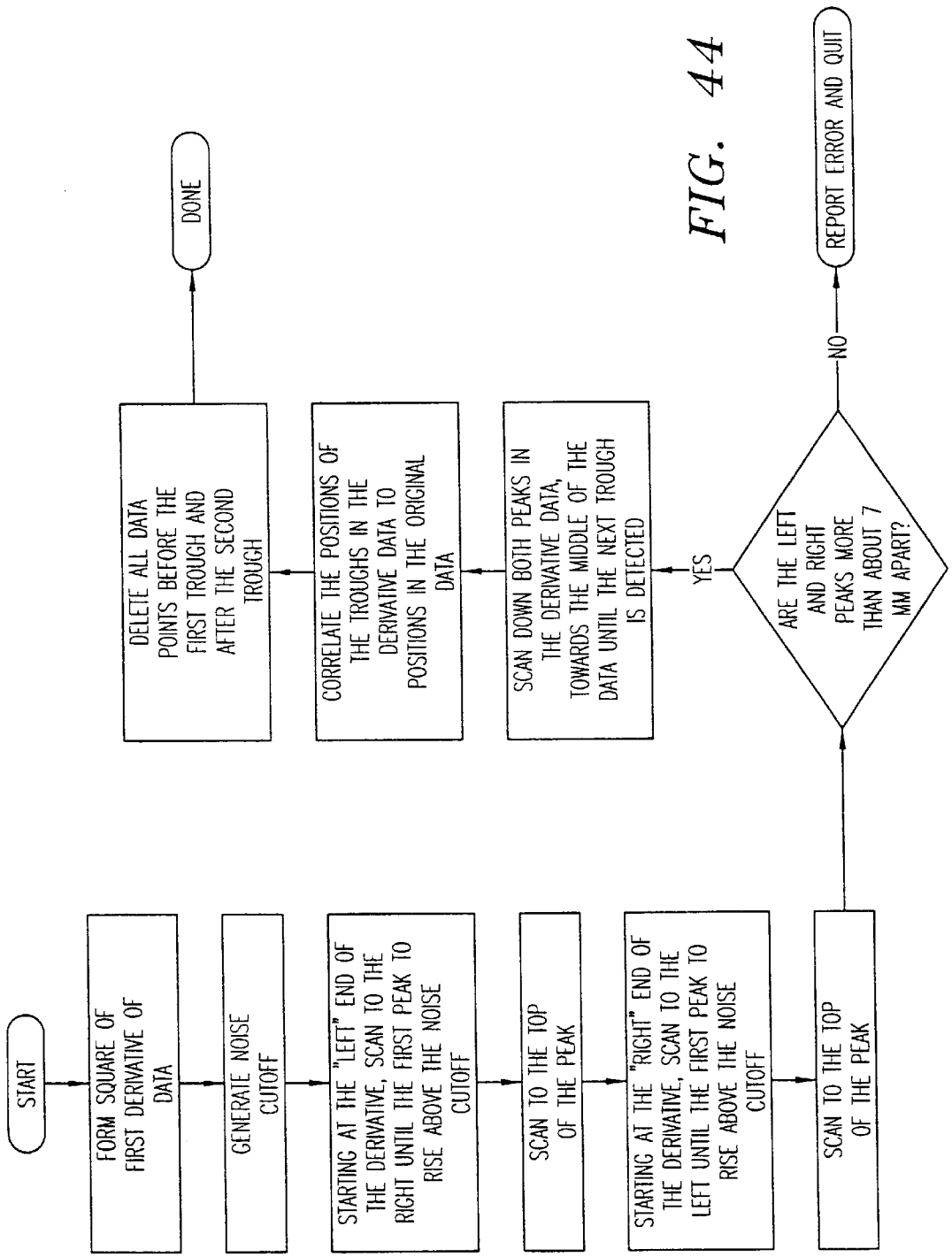
FIG. 44 depicts the data qualification/classification algorithm for the elimination of optical system over-scan from the data.
Figure 45:
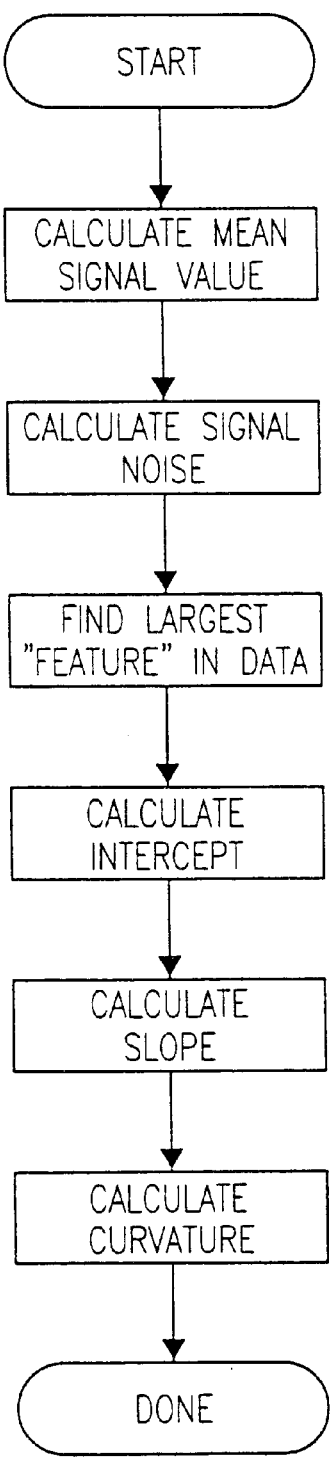
FIG. 45 depicts the data qualification/classification algorithm for the generation of pre-scan metrics.
Figure 46:
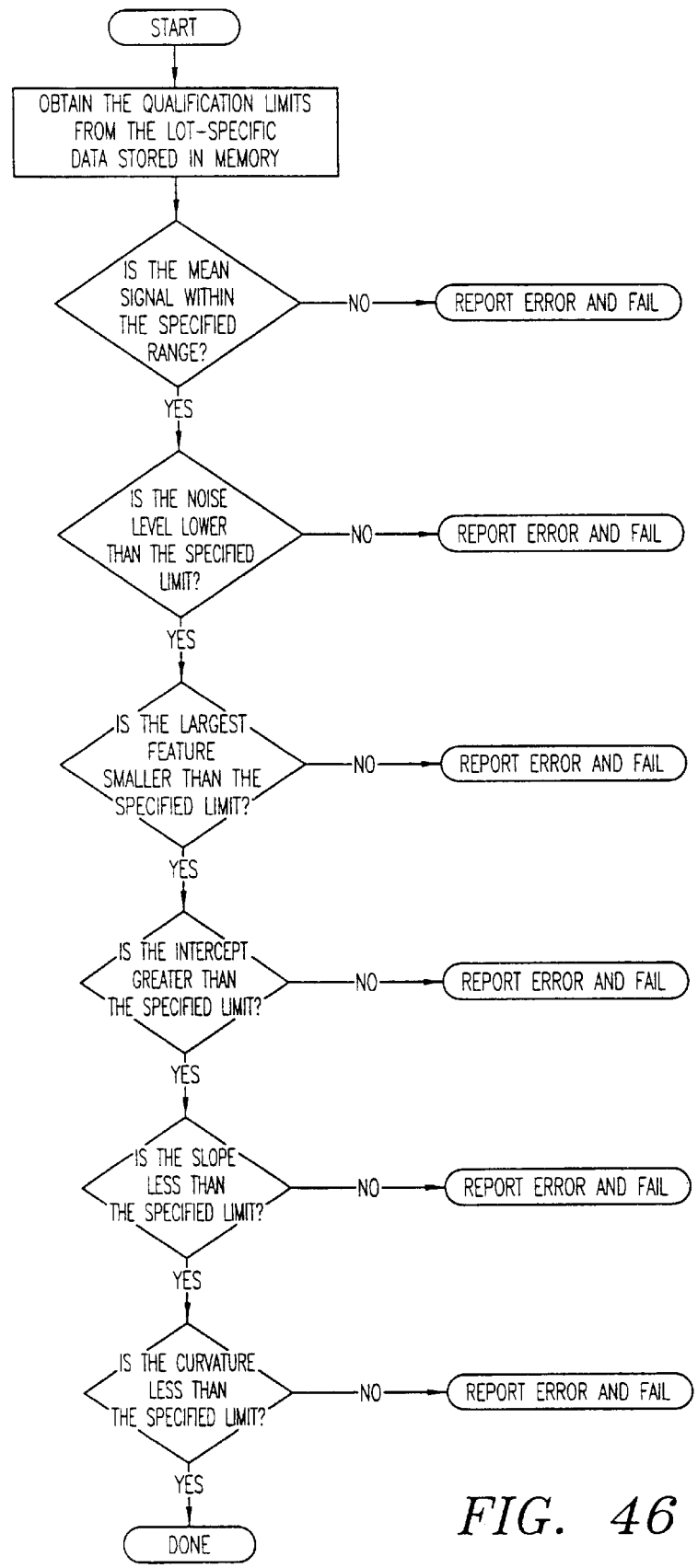
FIG. 46 depicts the data qualification/classification algorithm for the qualification of the pre-scan metrics.
Figure 47:
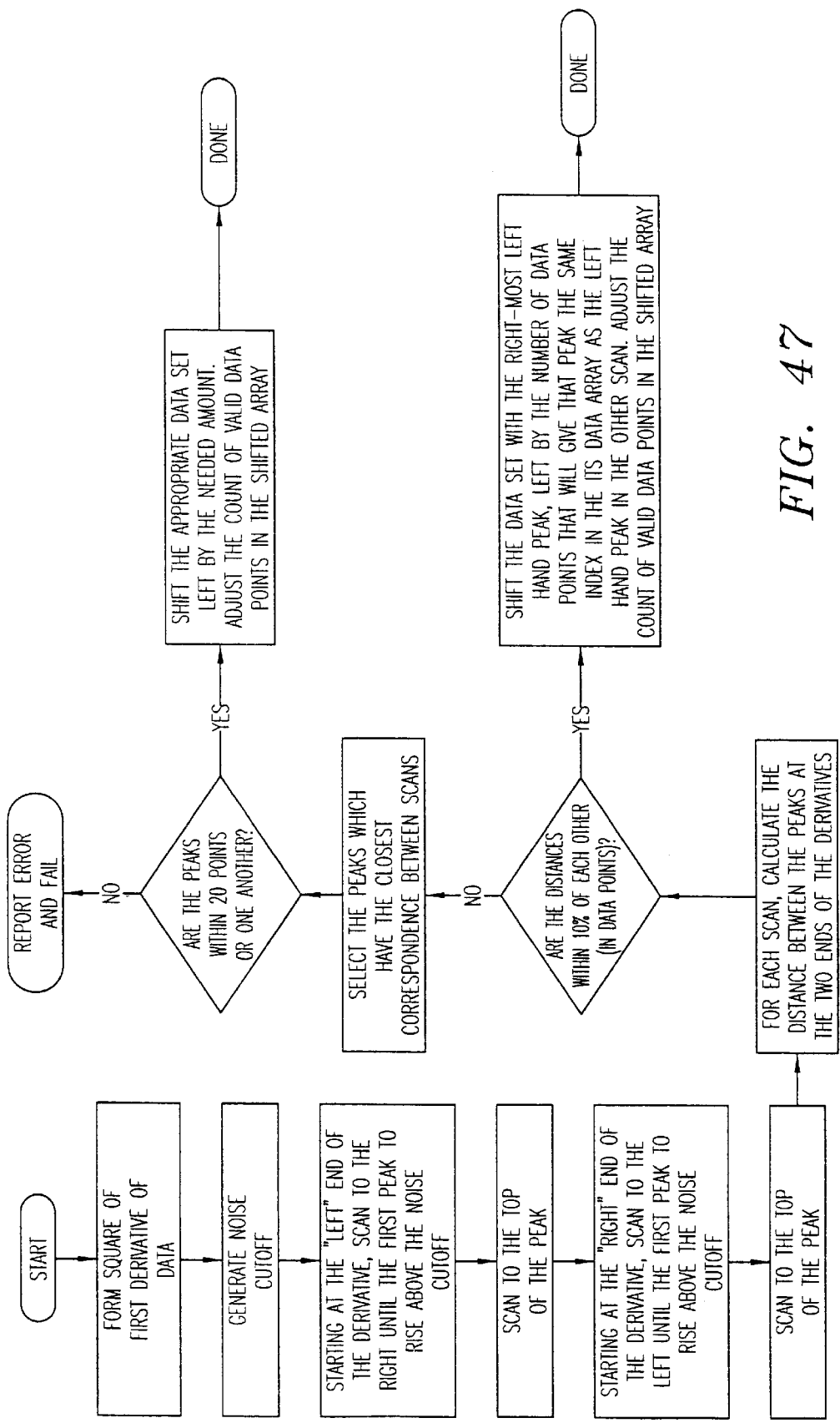
FIG. 47 depicts the data qualification/classification algorithm for the alignment of pre- and post-conjugate scan data.
Figure 48:
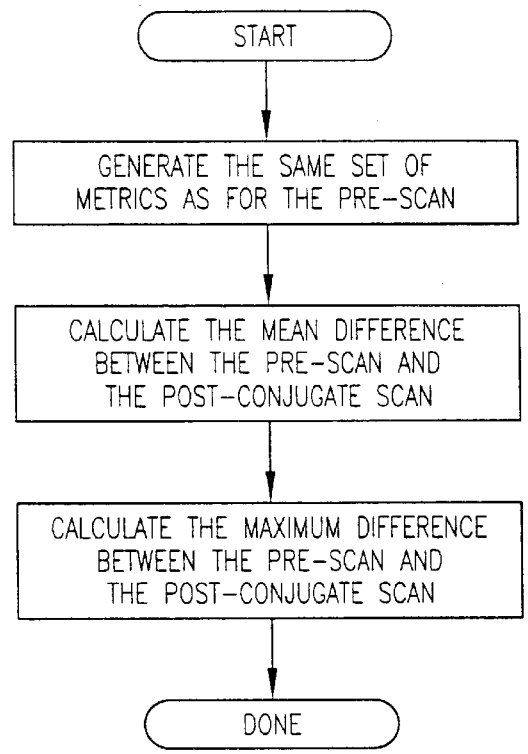
FIG. 48 depicts the data qualification/classification algorithm for the generation of post-conjugate metrics.
Figure 49:
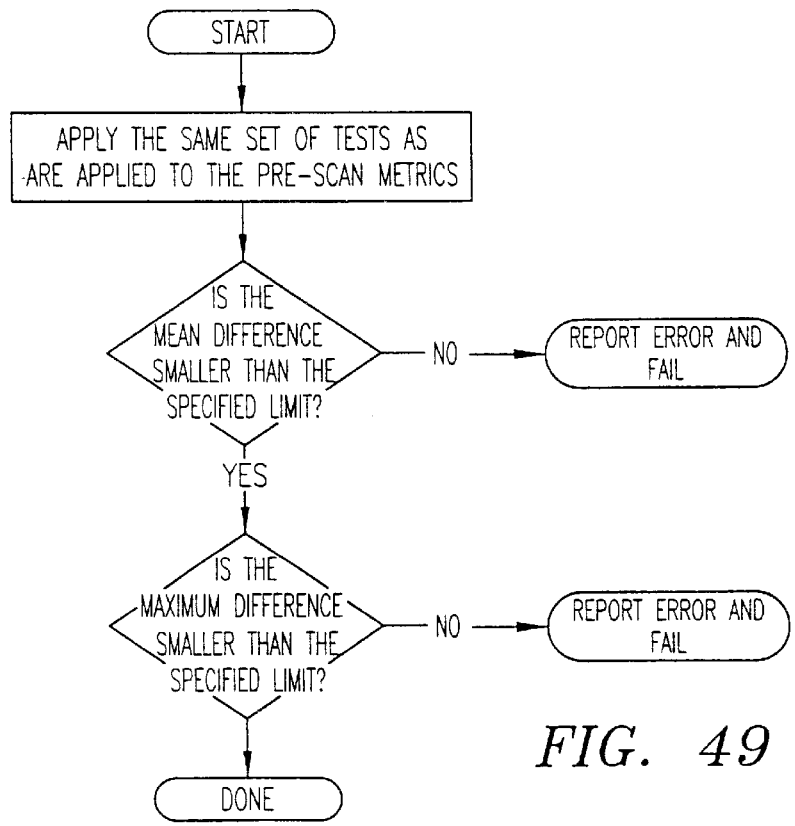
FIG. 49 depicts the data qualification/classification algorithm for the qualification of post-conjugate metrics.
Figure 50:
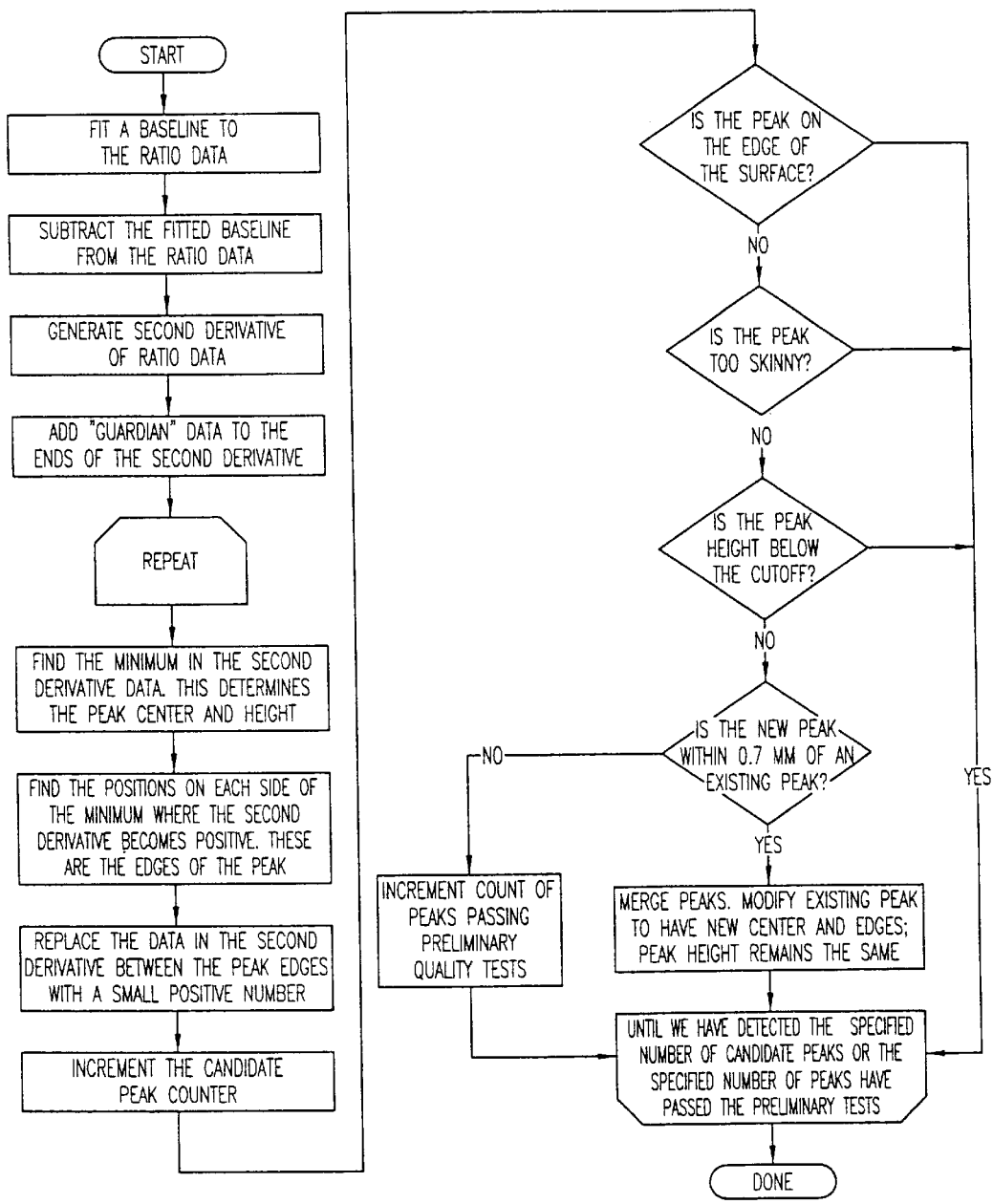
FIG. 50 depicts the data qualification/classification algorithm for the detection of peaks in the ratio data.
Figure 51:
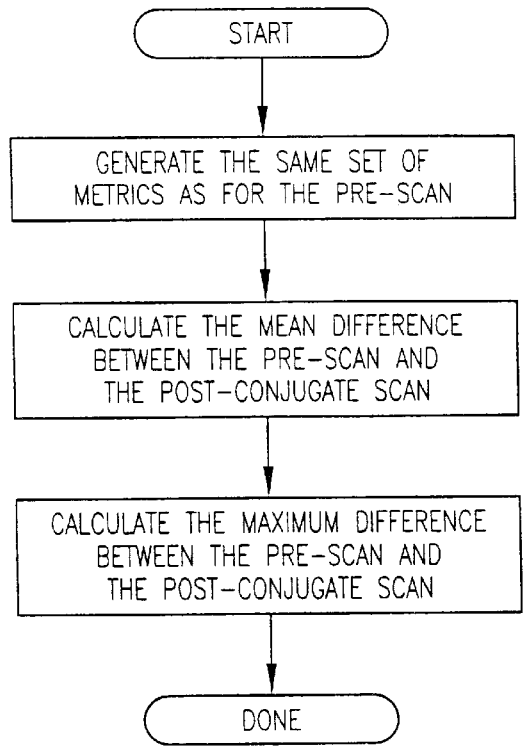
FIG. 51 depicts the data qualification/classification algorithm for the generation of post-conjugate metrics.
Figure 52:
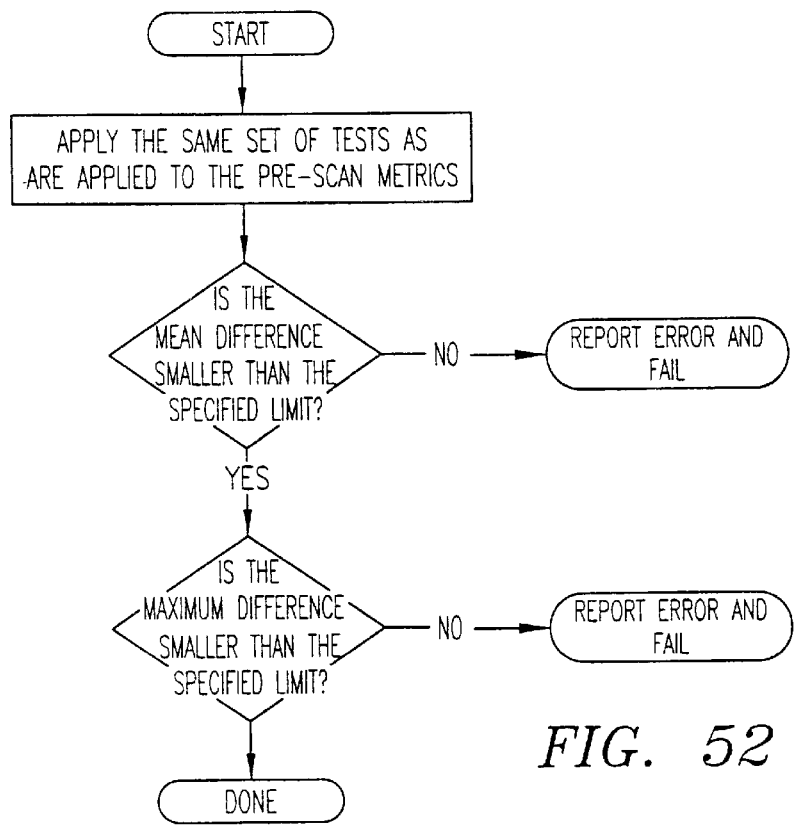
FIG. 52 depicts the data qualification/classification algorithm for the qualification of post-conjugate metrics.

FIG. 38 depicts one possible method for qualifying optical data as it is collected during the assay procedure. Data is qualified as it is collected and if at any point the data fails to meet the qualification requirements the analysis is terminated at that point. FIG. 39 depicts the first level of optical data qualification, applying metrics to the pre-assay procedure, optical scan. FIG. 40 depicts another level of optical data qualification. In this case the metrics are applied to a scan completed after the addition of an amplifying reagent to the optically active test surface. The amplifying reagent consists of an antibody and enzyme conjugate. The optical scan is conducted after a wash cycle is completed to remove any unbound amplifying reagent. One of the metrics applied must verify that the alignment of the optical scan being qualified matches the alignment of any previous scans to account for any surface variability that is not related to the assay result. The number of qualifications of optical data and optical scans and the metric applied will vary with the type of test surface under analysis. FIG. 41 depicts the same type of qualification as shown in FIG. 40. But the qualification is conducted after a precipitating substrate was been allowed to react with the amplifying reagent. FIG. 42 depicts one possible data processing mechanism. In this case the qualified optical scans are used to produce a ratio of the scan data. The peak ratio data is reported as a final result. FIG. 43 represents the steps required to store and report results. The storage table should allow all critical assay information to be stored. FIG. 44 depicts a method that can be used to eliminate optical overscan from the data set. Any number of normalization routines may be used to correct for the overscan in the data. A Savitsky-Golay polynomial can be used. Once the proper coefficients and polynomials are established for a particular assay cartridge the information is hard coded into the program. The noise cut-off for a particular assay system can be empirically determined and again hard coded into the program. FIG. 45 depicts one possible pre-scan metric analysis, while FIG. 46 depicts the qualification of those metrics. FIG. 47 depicts the process used for the alignment of the pre-and post-conjugate scans. This process is specific to one type of analyte-specific testing protocol and assay cartridge. However, similar considerations may apply to other assay systems. FIG. 48 depicts one method for the generation of metrics in one type of assay protocol, while FIG. 49 qualifies the same metrics. When the analyte capture portion of the test surface within the cartridge is created by applying the capture reagent in lines along the test surface, edge detection and peak detection in the optical scan will be a critical part of the data analysis. FIG. 50 represents one such approach to address these issues. FIG. 51 depicts a process to create the post-conjugate metrics, while FIG. 52 qualifies the metrics. Control algorithms also exist for the quality control requirements, adjusting or setting the time and date, instrument alarm and notification features, report language, instrument self-diagnostics, number of reports generated, etc.

Analyte Detection

Preferred analyte detection methods utilize an optically active test surface in conjunction with an ellipsometric detection method as described herein. One skilled in the art will understand that the methods described herein can be adapted to other test surfaces and detection methods. In certain preferred embodiments, an optically active test surface includes the following components: a support material, one or more optically functional layers, an optional attachment layer, an analyte-specific receptive material, and an optional protective overcoat. Preferably, the optically active test surface is designed to exploit thin film interactions with light. Attenuation of light incident on the optically active test surface is related to the changes in optical film thickness due to analyte binding to the optically active test surface.

In preferred embodiments, a representative support material would be a track etched polycarbonate membrane with a pore density of less than 15% of the total surface area. Other appropriate support materials are polyester, nylon, cellulose acetate, woven and non-woven materials, polysulfones, polypropylenes, and polyurethanes. Other porous or non-porous materials may be utilized. Non-porous materials would require adaptation of the cartridge 1 to permit fluid flow around the test surface under vacuum and the surface must not break or crack under vacuum. The support must be capable of being processed by the procedures used to deposit the optically functional layers and all subsequent processing steps. The support need not have the optical properties desired in the final optically active test surface as the subsequent coatings can supply the proper optical characteristics. The support should be chemically inert to all the chemicals and solvents used in subsequent processing steps. All subsequent layers should maintain the porosity of the original support.

Preferably, the analyte-specific receptive layer is a material or materials that have sufficient affinity and specificity to bind the analyte of interest to the surface of the optically active test device. This allows for detection of the analyte of interest. Once the analyte-specific receptive layer is coated onto the optically active test surface, an overcoat layer may be applied to increase the long term stability of the optically active test device. Representative analyte-specific receptive layers include antigens, antibodies, lipopolysaccharides, polysaccharides, microorganisms, food contaminants, environmental agents, allergens, nucleic acids, DNA, RNA, pesticides, ligands, receptors, chelates, proteins, enzymes, herbicides, inorganic or organic compounds or fragments or analogs thereof. The analyte-specific receptive material may be applied to surface by solution coating, spray coating, spot coating, ink jetting, air brushing, or other processes known to those skilled in the art. The analyte-specific binding material can be applied as a stripe, or a spot, or other appropriate geometric design. The analyte-specific binding material should be applied in a specific, reproducible pattern to facilitate optical reading of the reacted surface.

In addition to an analyte-specific binding material, the test surface may be coated with one or more control materials. These control materials can be used to assist in the verification that the proper assay sequence was performed and that the assay reagents were functioning as anticipated. In other preferred embodiments, more than one analyte-specific binding material can be applied to the test surface. The number of analyte-specific binding materials applied is limited only by the ability to resolve the individual reaction zones with the detection method employed.

Preferred analytes may include antigens, antibodies, lipopolysaccharides, polysaccharides, microorganisms, food contaminants, environmental agents, allergens, nucleic acids, DNA, RNA, pesticides, ligands, receptors, chelates, proteins, enzymes, herbicides, inorganic or organic compounds or fragments or analogs thereof.

The assay system may be applied to a wide range of different analytical testing applications. The assay cartridge components determine what analyte is being detected and the instrument analyzes the reactions on the test surface in the cartridge and reports a result. The assay cartridge can be used in the detection of an infectious disease from a patient specimen where the specimen may be a throat swab, a nasal swab, a nasal wash, urine, blood, serum, plasma, a wound swab, a vaginal swab, a urethral swab, a endocervical swab, or other appropriate body fluid or collection swab. The assay cartridge can be used to detect other medical conditions from similar specimen types. The assay cartridge can be used to detect a specific component of a manufacturing process's waste. The assay cartridge can be used to detect the presence of an undesirable component in a food. The assay cartridge can be designed to detect a material for which there exists a specific binding agent.

In certain embodiments, an amplifying reagent may be used to increase the thin film effect of analyte binding to the thin film test surface (i.e., the optically active test surface) and is most preferably an enzyme-labeled antibody. For example, an insoluble reaction product results when an immobilized antibody-antigen-antibody-enzyme complex is present on the test surface. A reaction product is catalytically precipitated by the action of the enzyme on a precipitating agent in solution. Precipitating agents include combinations of alginic acid, dextran sulfate, methyl vinyl ether/maleic anhydride copolymer, or carrageenan and the like, as well as the product formed by the interaction of TMB (3,3',5,5'-tetra-methyl-benzidine) with an oxygen free radical. This particular precipitating agent forms an insoluble product whenever a free radical contacts the TMB. Other substances including 4-chloronapthol, diaminobenzidene tetrahydrochloride, aminoethyl-carbazole, orthophenylene-diamine and the like can also be used as precipitating agents. The precipitating agent is typically used in concentrations ranging from about 10 mM to 100 mM. But any material that can be attached to an analyte-specific binding reagent and can serve to increase the optical thickness of the analyte layer can be utilized.

Most preferably, the optical detection system used in the instrument is a thin film analyzer described in U.S. Pat. Nos. 5,494,829 and 5,631,171 and these references are hereby incorporated in their entirety. The thin film analyzer is designed to detect a change in the degree of polarization of light incident upon the optically active test surface. A change in the thin film due to analyte binding results in an attenuation of the light due to a further change in the degree of polarization of the light. The light is phase delayed by reflection through the thin films. The optical detection system is simple and inexpensive. The system includes a light source, two polarizers, and a detector. Preferably the light source is monochromatic. The detector is a silicon diode. The first polarizer in the system is used to provide incident light that is linearly polarized. The second polarizer or analyzer is set to select the change in polarization of the reflected light that is due to the presence of analyte binding. In other words the analyzer is set to minimize the signal to the detector when light is reflected from an unreacted optically active test surface.

In other preferred embodiments, the test surface may also be an unmodified polycarbonate support. In this case the test surface is preferably coated with the analyte-specific binding reagent and the signal generation is due to a reagent that binds the immobilized analyte and carries with it a chromophore, fluorophore, or the like to assist in detection. Construction of the test surface would be very similar to the considerations applied to the optically active test surface without the intervening optical layers. However, application of the analyte-specific binding reagent would use very similar methods. Assembly and use of the cartridge may or may not be different than when an optically active surface is utilized. It is preferably left to the skill of the artisan to determine the appropriate cartridge design and methods to be employed, according to the specific requirements to be met by the assay to be performed.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

We claim:

1. An assay cartridge for use in an analytical instrument, the assay cartridge comprising:
a bottom member comprising an optical reading well and a test surface; and
a top member comprising a rotatable reagent carousel, said reagent carousel comprising a sample receiving port and a plurality of reagent wells, wherein one or more of said reagent wells comprise a reagent and a reagent well piston for delivery of said reagent to the test surface.

2. An assay cartridge for use in an analytical instrument, the assay cartridge comprising:
a bottom member comprising an optical reading well and a test surface; and
a top member comprising a rotatable reagent carousel, said reagent carousel comprising a sample receiving port, a plurality of reagent wells, a reagent flow channel, and a differential seal,
wherein said test surface lies in said optical reading well,
wherein one or more of said regent wells comprise a reagent and a reagent well piston for delivery of said reagent to the test surface, and
wherein said reagent flow channel is adjacent to said sample receiving port, a top part of said reagent flow channel is connected to a top part of said sample receiving port, and said differential seal lies between a bottom part of said reagent flow channel and a bottom part of one of said reagent wells, thereby allowing flow to occur from one of said reagent wells through said reagent flow channel to said sample receiving port.

3. An assay cartridge according to claims 1 or 2, wherein said test surface comprises an analyte-specific binding layer for immobilizing an analyte on said test surface.

4. An assay cartridge according to claims 1 or 2, wherein said test surface nonspecifically immobilizes an analyte on said test surface.

5. An assay cartridge according to claims 1 or 2, wherein said test surface is an optically active test surface.

6. An assay cartridge according to claim 5, wherein said optically active test surface is adapted to generate an interference, ellipsometric, or polarization signal.

7. An assay cartridge according to claims 1 or 2, wherein said rotatable carousel further comprises a sample processing element.

8. An assay cartridge according to claim 7, wherein said sample processing element comprises a filtration surface.

9. An assay cartridge according to claims 1 or 2, wherein said sample receiving port is adapted to receive a swab type sample collection device.

10. An assay cartridge according to claims 1 or 2, wherein a bottom portion of each reagent well is sealed by a breakable seal material, and wherein a top portion of each reagent well is sealed by said reagent well piston in combination with a breakable seal material.

11. An assay cartridge according to claim 10, wherein each reagent well piston comprises a piercing element to break said breakable seal material sealing the bottom of said reagent well upon application of a sufficient force.

12. An assay cartridge according to claims 1 or 2, wherein the bottom member comprises extender tabs adapted to ensure proper registration of said assay cartridge with said analytical instrument.

13. The assay cartridge of claim 12, wherein the extender tabs further comprise a locking mechanism for carousel rotation.

14. An assay cartridge according to claims 1 or 2, wherein each reagent well piston comprises a hex boss element.

15. An assay cartridge according to claims 1 or 2, wherein said analytical instrument is a completely automated point of care instrument.

16. An assay cartridge according to claim 2, wherein said analytical instrument is a completely automated point of care instrument.

17. The assay cartridge of claims 1 or 2, further comprising an extraction reagent flow channel and a differential seal for the control of extraction reagent to the sample receiving port.

18. A method of fabricating an assay cartridge according to claims 1 or 2, the method comprising:
attaching the bottom member to the top member such that the rotatable reagent carousel may be rotated relative to the bottom member.

19. An analytical instrument for determining the presence or amount of an analyte in a sample, the analytical instrument comprising:
an assay cartridge comprising
(i) a bottom member comprising an optical reading well and a test surface; and
(ii) a top member comprising a reagent carousel, said reagent carousel comprising a sample receiving port and a plurality of reagent wells, wherein one or more of said reagent wells comprise a reagent and a reagent well piston for delivery of said reagent to the test surface, said top member attached to said bottom member such that the reagent carousel may be rotated relative to the bottom member.
a mechanism for receiving said assay cartridge;
a rotation element for rotating and indexing said reagent carousel;
a plunger element for engaging said reagent well pistons to deliver reagent from said reagent wells to said sample receiving port and/or said test surface;
a vacuum element for directing sample and/or reagent to said test surface;
a detector for detecting a signal from said test surface;
a control processor for controlling the rotating, plunger, and vacuum elements according to an assay algorithm; and
a signal processor for relating the generated signal to the presence or amount of said analyte.

20. An analytical instrument according to claim 19 further comprising a mechanism for linear translation mechanism for translating the assay cartridge within the analytical instrument.

21. An analytical instrument according to claim 19 further comprising a presser foot for stabilizing said assay cartridge.

22. An analytical instrument according to claim 19 further comprising an optical control element for determining cartridge orientation.

23. An analytical instrument according to claim 19, wherein said rotation element comprises a mechanical arm and motor.

24. An analytical instrument according to claim 19, wherein said plunger element comprises a push rod attached to a vertical drive element.

25. An analytical instrument according to claim 24 wherein said push rod is adapted to seat in a hex boss element on said reagent well piston.

26. An analytical instrument according to claim 25, wherein said push rod returns said reagent well piston to about its original position in the reagent well following delivery of said reagent.

27. An analytical instrument according to claim 19, wherein said detector is selected from the group consisting of a color sensor, a color detector, an image detector, a spectrophotometer, a luminometer, a fluorometer, a potentiometer, an interferometer, a polarimeter, and an ellipsometer.

28. An analytical instrument according to claim 19, wherein said detector is a fixed polarizer ellipsometer.

29. An analytical instrument according to claim 19, wherein said control processor and said signal processor consist of a single general purpose computer programmed to perform instrument control and data processing algorithms.

30. An analytical instrument according to claim 19, wherein said assay cartridge comprises an identifying element which identifies the analyte and/or the sample to the analytical instrument.

31. An analytical instrument according to claim 30, wherein said identifying element is a bar code, and said analytical instrument comprises a bar code reader configured to read said bar code.

32. An analytical instrument according to claim 19, wherein said sample receiving port is adapted to receive a swab type sample collection device.

33. An analytical instrument according to claim 19, wherein said analytical instrument is a completely automated point of care instrument.

34. A method of determining the presence or amount of an analyte in a sample, the method comprising:
providing an assay cartridge comprising
(i) a bottom member comprising an optical reading well and a test surface; and
(ii) a top member comprising a reagent carousel, said reagent carousel comprising a sample receiving port and a plurality of reagent wells, wherein one or more of said reagent wells comprise a reagent and a reagent well piston for delivery of said reagent to the test surface, said top member attached to said bottom member such that the reagent carousel may be rotated relative to the bottom member;
providing an analytical instrument comprising
(i) a mechanism for receiving said assay cartridge;
(ii) a rotation element for rotating and indexing said rotatable carousel;
(iii) a plunger element for engaging said reagent well pistons to deliver reagent from said reagent wells to said test surface;
(iv) a vacuum element for directing sample and/or reagent to said test surface;
(v) a detector for generating a signal from said test surface;
(vi) a control processor for controlling the rotating, plunger, and vacuum mechanisms according to an assay algorithm; and
(vii) a signal processor for relating the generated signal to the presence or amount of said analyte;
placing said sample into the sample receiving port of said cartridge;
placing said assay cartridge into said receiving mechanism;
performing an assay using said analytical instrument according to said assay algorithm, whereby said signal processor determines the presence or amount of said analyte in said sample.

35. A method according to claim 34, wherein said sample is selected from the group consisting of a throat swab, a vaginal swab, an endocervical swab, a rectal swab, a urethral swab, a nasal swab, a nasopharyngeal swab, a fluid, water, urine, blood, sputum, serum, plasma, an aspirate, a wash, a tissue homogenate, and a process fluid.

36. A method of determining the presence or amount of an analyte in a sample, the method comprising:
providing an assay cartridge comprising
a test surface;
a sample receiving port;
all reagents necessary for performing an assay;
a bottom member comprising an optical reading well and said test surface; and
a top member comprising a rotatable reagent carousel, said reagent carousel comprising said sample receiving port and a plurality of reagent wells, wherein one or more of said reagent wells comprise a reagent and a reagent well piston for delivery of said reagent to the test surface; and
providing an analytic instrument comprising
(i) a mechanism for receiving said assay cartridge;
(ii) a mechanism for delivering said sample to said test surface;
(iii) a mechanism for delivering said reagents to said test surface;
(iv) a detector for generating a signal from said test surface;
(v) a control processor for controlling said delivery mechanisms according to an assay algorithm; and
(vi) a signal processor for relating the generated signal to the presence or amount of said analyte;
placing said sample into the sample receiving port of said cartridge;
placing said assay cartridge into said receiving mechanism; and
performing said assay automatically using said analytical instrument according to said assay algorithm, whereby said signal processor determines the presence or amount of said analyte in said sample.

37. The method of claim 36, wherein one of said reagents comprises a sample extraction reagent, and said analytical instrument further comprises a mechanism for delivering said sample extraction reagent to said sample receiving port and allowing for extraction of one or more analyte from said sample, and said mechanism for delivering said sample to said test surface further comprises a mechanism for delivering said extracted sample to said test surface.

38. The method of claim 36, wherein said sample is selected from the group consisting of urine, water, blood, sputum, plasma, serum, aspirates, washes, tissue homogenate, process fluids, throat swabs, vaginal swabs, endocervical swabs, rectal swabs, urethral swabs, nasopharyngeal swabs, and biological fluids.

* * * * *